United States Patent
Pedrño Egea et al.

(10) Patent No.: US 8,759,294 B2
(45) Date of Patent: Jun. 24, 2014

(54) MICROVESICLES DERIVED FROM RECOMBINANT YEAST HAVING HAEMOSTATIC ACTIVITIES AND USES THEREOF

(75) Inventors: Francisco Javier Pedrño Egea, Barcelona (ES); Luis Ignacio Caveda Catasus, Barcelona (ES); Juan Ramón Rodríguez Fernández-Alba, Madrid (ES)

(73) Assignee: Thrombotargets Europe, S.L., Castelldefels (ES)

( * ) Notice: Subject to any disclaimer, the term of this patent is extended or adjusted under 35 U.S.C. 154(b) by 555 days.

(21) Appl. No.: 12/521,492

(22) PCT Filed: Dec. 28, 2007

(86) PCT No.: PCT/EP2007/064644
§ 371 (c)(1),
(2), (4) Date: Jul. 14, 2009

(87) PCT Pub. No.: WO2008/080989
PCT Pub. Date: Jul. 10, 2008

(65) Prior Publication Data
US 2010/0047335 A1    Feb. 25, 2010

(30) Foreign Application Priority Data
Dec. 29, 2006 (EP) .................................. 06380342

(51) Int. Cl.
*A61K 38/36* (2006.01)
*C07K 14/745* (2006.01)

(52) U.S. Cl.
USPC .................... 514/14.3; 514/13.7; 435/69.9

(58) Field of Classification Search
None
See application file for complete search history.

(56) References Cited

U.S. PATENT DOCUMENTS

| | | | |
|---|---|---|---|
| 6,261,803 B1 * | 7/2001 | Zander et al. | 435/69.1 |
| 6,994,988 B1 | 2/2006 | Lawn et al. | |
| 7,084,251 B1 | 8/2006 | Lawn et al. | |
| 8,062,638 B1 | 11/2011 | Saito et al. | |
| 2002/0012699 A1 | 1/2002 | Singh et al. | |

FOREIGN PATENT DOCUMENTS

| | | |
|---|---|---|
| RU | 2002111683 A | 3/2004 |
| WO | 9323074 | 11/1993 |
| WO | 9848283 | 10/1998 |
| WO | 02087594 A1 | 11/2002 |
| WO | 2006004675 A2 | 1/2006 |

OTHER PUBLICATIONS

Austin, A.J., et al. 1998 Protein Expression and Purification 13: 136-142.*
Sergel, T.A., et al. 2000 J Virology 74(11): 5101-5107.*
Yuan, S-M., et al. 1998 Proteins 30: 136-143.*
Muller, Ingrid, et al., Intravascular tissue factor initiates coagulation via circulating microvesicles and platelets, The FASEB Journal express article 10.1096/fj.02-0574fje, 2003, 21 pages.
Waters, Emily K., et al., Restoring full biological activity to the isolated ectodomain of an integral membrane protein, Biochemistry, Mar. 21, 2006, pp. 3769-3774, vol. 45, No. 11.
Brucato, Cheryl L., et al., Expression of recombinant rabbit tissue factor in *Pichia pastoris*, and its application in a prothrombin time reagent, Protein Expression & Purification, 2002, pp. 386-393, vol. 26.
Guha, A., et al., Affinity purification of human tissue factor: interaction of factor VII and tissue factor in detergent micelles, Proceedings of the National Academy of Sciences of the United States of America, Jan. 1986, 83, pp. 299-302.
Ratajczak, J., et al.; "Embryonic stem cell-derived microvesicles reprogram hematopoietic progenitors: evidence for horizontal transfer of mRNA and protein delivery," Leukemia, 2006, pp. 847-856, vol. 20.
Ratajczak, J., et al.; "Membrane-derived microvesicles: important and underappreciated mediators of cell-to-cell communication," Leukemia, 2006, pp. 1487-1495, vol. 20.
Whiteside, TL; "Tumor-derived exosomes or microvesicles: another mechanism of tumor escape from the host immune system?" British Journal of Cancer, 2005, pp. 209-211, vol. 92.
Kedzierski, Lukasz, et al.; "Comparison of the protective efficacy of yeast-derived and *Escherichia coli*-derived recombinant merozoite surface protein 4/5 against lethal challenge by *Plasmodium yoelii*," Vaccine, 2001, pp. 4661-4668, vol. 19.
Huang, Pingbo, et al.; "Functional expression of the cystic fibrosis transmembrane conductance regulator in yeast," Biochimica et Biophysica Acta, 1996, pp. 80-90, vol. 1281.

* cited by examiner

*Primary Examiner* — Marsha Tsay
(74) *Attorney, Agent, or Firm* — Tristan A. Fuierer; Andrew D. Gerschutz; Moore & Van Allen, PLLC

(57) ABSTRACT

Tissue factor-bearing yeast derived microvesicles comprising a yeast membrane and a tissue factor protein, or a fragment thereof, or a tissue factor protein or a fragment thereof fused to another peptide as a fusion protein having pro-coagulant activity are disclosed. Said products can be used as pro-coagulant agents in the treatment of hemorrhages in a subject.

19 Claims, 26 Drawing Sheets
(6 of 26 Drawing Sheet(s) Filed in Color)

Human TF cDNA GenBank #BC011029

```
121  cccacgggcg ccacggaacc cgctcgatct cgccgccaac tggtagadat gjagacccct
     gggtgcccgc ggtgccttgg gcgagctaga gcggcggttg accatctgta cctctgggga 181  gcctggcccc gggtcccgcg ccccgagacc gccgtcgctc ggacgctcct gctcggctgg
     cggaccgggg cccagggcgc ggggctctgg cggcagcgag cctgcgagga cgagccgacc 241  gtcttcgccc aggtggccgg c......... .......... .......... ..........
     cagaagcggg tccaccggcc g......... .......... .......... ..........

301  .......... .......... .......... .......... .......... ..........

361  .......... .......... .......... .......... .......... ..........

421  .......... .......... .......... .......... .......... ..........

481  .......... .......... .......... .......... .......... ..........

541  .......... .......... .......... .......... .......... ..........

601  .......... .......... .......... .......... .......... ..........

661  .......... .......... .......... .......... .......... ..........

721  .......... .......... .......... .......... .......... ..........

781  .......... .......... .......... .......... .......... ..........

841  .......... .......... .......... .......... .......... ..........

901  .......... .......... .......... .......... .......... ..........

961  .......... .......... .......... .......... .......... ..........

1021 .......... .......... .......... .......... agga agcactgttg gagctactgc
     .......... .......... .......... .......... .cct tcgtgacaac ctcgatgacg
```

Figure 3

TAG: Triacylglycerides
ERG: Ergosterol
PE: Phosphatidylethanolamine
CAR: Cardiolipin
PA: Phosphatidic acid
PC: Phosphatydilcholine
PS/PI: Phosphatidylserine/Phosphatidylinositol TLC: Chloroform:Methanol:Water (C:M:W. 345:133:21, v/v/v)

Human TF cDNA GenBank #BC011029

MICROVESICLES DERIVED FROM RECOMBINANT YEAST HAVING HAEMOSTATIC ACTIVITIES AND USES THEREOF

CROSS-REFERENCE TO RELATED APPLICATIONS

This application is filed under the provisions of 35 U.S.C. §371 and claims the priority of International Patent Application No. PCT/EP2007/064644 filed on 28 Dec. 2007 entitled "Microvesicles Derived from Recombinant Yeast Having Haemostatic Activities and Uses Thereof" in the name of Javier Pedreño Egea, et al., which claims priority of European Patent Application No. EP06380342.3 filed on 29 Dec. 2006, both of which are hereby incorporated by reference herein in their entirety.

FIELD OF THE INVENTION

The present invention refers, in general, to the treatment of hemorrhages in a subject with a pro-coagulant agent. More specifically, the invention relates to a tissue factor-bearing yeast-derived microvesicles comprising a yeast membrane and a tissue factor protein, or a fragment thereof, or a tissue factor protein or a fragment thereof fused to another peptide as a fusion protein having pro-coagulant activity, and to its applications as a pro-coagulant agent useful for treating hemorrhages in a subject as well as for promoting angiogenesis and cell migration. The invention further relates to processes for the production of said tissue factor-bearing yeast-derived microvesicle.

BACKGROUND OF THE INVENTION

Hemostasis is the mechanism by means of which living beings respond to a hemorrhage and involves the participation of two processes that become functional immediately after a lesion and remain active for a long period of time. The first of them is known as primary hemostasis and is characterized by the occurrence of vasoconstriction at the vascular lesion site and platelet aggregate formation. The second one is known as secondary hemostasis, being the phase in which the fibrin clot is formed due to the action of the different coagulation cascade proteolytic enzymes.

Several cofactors and proteolytic enzymes participate in the second phase of the blood coagulation process, all referred to as coagulation factors, and it consists of several phases ending with fibrin formation from fibrinogen hydrolysis due to the action of thrombin. Thrombin is previously formed by proteolytic hydrolysis of an apoenzyme, prothrombin. This proteolysis is carried out by the activated coagulation Factor X (FXa), which binds to the surface of the activated platelets and only in the presence of its cofactor, activated coagulation Factor V (FVa), and calcium ions, and is able to hydrolyze prothrombin. Coagulation Factor X (FX) activation can occur in two separate pathways, the intrinsic pathway and the extrinsic pathway.

The intrinsic pathway consists of a series of reactions in which each proenzyme is hydrolyzed, yielding its active protease form. In each step, the recently formed proteolytic enzyme will catalyze activation of the following proenzyme to successively yield the active form.

In the blood coagulation extrinsic pathway, the Tissue Factor (TF), exposed on adventitia cells at the lesion site, binds to circulating coagulation Factor VII/activated coagulation Factor VII (FVII/FVIa) to form the TF::FVIIa complex and, in the presence of calcium, to act as a substrate so that FX activation takes place. The extrinsic pathway is currently considered the most relevant pathway in blood coagulation, and it is accepted that in the event of a hemorrhage produced by a vascular lesion, coagulation is triggered due to extrinsic pathway activation involving the interaction of TF with its ligand, FVII/FVIIa.

TF consists of a protein component (previously referred to as tissue factor apoprotein-III) and a phospholipid. TF specifically binds to FVII/FVIIa and plays a relevant role in the blood coagulation extrinsic pathway. The physiological roles assigned to TF are well known; on the one hand, it is a receptor specific for FVIIa and, once the TF::FVIIa complex has been formed, it acts as a substrate so that FX activation takes place. In fact, after a vascular lesion, TF, which is normally sequestered on the surface of adventitia cells externally surrounding blood vessels, comes into contact and interacts with its ligand, FVII present in blood, to form the TF::FVII complex. Once this complex is formed, FVII autoactivation takes place, yielding its active form (FVIIa).

Glycosylation is an enzyme directed site specific process by which saccharides are added to lipids and proteins. It is believed that this process is involved in stability, folding, and transport; although no evidence of its real function has been described for TF.

It has been broadly accepted that TF is the main element responsible for the quickness with which coagulation is initiated. For coagulation to begin, it is absolutely necessary for FX to be activated and begin prothrombin hydrolysis. The source of this FXa has mainly been attributed to the interaction of FVIIa with its receptor, TF.

Purification of TF has been reported from various tissues such as: human brain, bovine brain; human placenta; ovine brain; and, lung. It is widely accepted that while there are differences in structure of TF protein between species there are no functional differences as measured by in vitro coagulation assays.

It is widely accepted that in order to demonstrate biological activity, TF must be associated with phospholipids in vitro. It has been shown that the removal of the phospholipid component of TF, for example by use of a phospholipase, results in a loss of its biological activity in vitro. Relipidation can restore in vitro TF activity.

While some quantities of "purified" TF protein have been available as obtained from various tissues, the low concentration of TF protein in blood and tissues and the high cost, both economic and of effort, of purifying the protein from tissues makes this a scarce material. Therefore, there is a need to look for an alternative source of TF protein, advantageously lipidated TF protein.

The TF protein has been expressed in various systems using the cloned human cDNA. Thus, over-expression of TF protein in E. coli has been reported (Paborsky et al., Biochemistry 28, 8072 (1989)). Further, U.S. Pat. No. 6,261,803 discloses a process for preparing functional recombinant TF in a prokaryotic host organism. High expression yield of the complete TF protein is achieved in E. coli.

Although heterologous expression of proteins in E. coli presents some advantages, the expression of eukaryotic proteins in said bacteria is associated with a large number of problems, mainly when the protein to be expressed is a glycosylated eukaryotic protein, due to the lack in bacteria of their own glycosylation systems.

An alternative strategy consists, therefore, in expressing a mutated TF protein which lacks the transmembrane domain. This so-called "soluble" TF (or "truncated" TF) accumulates in the cytoplasm of the bacterial cells and can be expressed in relatively large quantities. However, in this system, the TF protein so expressed is usually present in *E. coli* in a quasicrystalline state in the form of so-called inclusion bodies. When this is the case, the inclusion bodies have to be solubilized by using very large quantities of chaotropic agents, and the proteins which have been monomerized in this way have then once again to be refolded, with a great deal of effort and usually with only a low yield, into an active, renatured confirmation. Further, in principle, the soluble TF is not suitable for use in prothrombin time reagents since it lacks the domain for the interaction with phospholipids.

Another approach for over-expressing TF protein is that of using a large number of known and successfully employed expression systems which encode products of gene fusions (e.g. with β-galactosidase, MalE, glutathione transferase, His-tag, etc.). However, these systems are not suitable for expressing biologically active TF. Although expression products can be detected and the level of expression can also be increased when said systems are used, the expression products so obtained are sometimes associated with a complete loss of function, which cannot be restored, either, even using elaborate renaturation methods.

The problems of over-expression of TF protein in *E. coli* can be circumvented by carrying out the expression of said protein in a eukaryotic system. Thus, expression in yeast cells, in insect cell cultures using baculovirus as a vector, or in cultured mammalian cells, e.g., hamster ovary cells, or in human cell lines, is, in principle, suitable. However, these systems suffer from crucial disadvantages, among others; recombinant protein yields are much lower when compared to recombinant *E. coli* production.

Yeast strains combine the advantages of the above distinct host systems. On one hand, they more closely mimic the native physiology of an eukaryotic protein than *E. coli*, and, on the other hand, they are ease of handling, ease of culturing, present much faster growth and much greater economy. Several factors though, affect the expression of proteins in yeast as well. These factors include, but are not confined to:

the choice of the gene regulatory sequences, such as promoters, that control the expression of an heterologous protein; the promoter sequences employed for controlling heterologous expression should typically be "strong", i.e., they should effect very high expression of the protein, and suitably controllable, whereby the expression may at first be efficiently repressed until an optimum biomass of the culture is reached and then quickly switched on to effect protein expression; and an efficient secretion of the expressed heterologous protein; secretion of the expressed protein (extracellular expression) is often preferred over intracellular expression as the latter would first entail breaking open the cell, thus disgorging the entire cellular contents, and then isolating the desired protein from the cesspool of cellular material and debris. Yet efficient secretion of a protein in turn depends on several factors including: (i) the choice of the signal sequences-peptide sequences which are usually the N-terminal regions of naturally secreted proteins, and which direct the protein into the cellular secretory pathway, and, (ii) the specific components of the secretory pathway that interact with signal sequences and effect the secretion of the attached protein.

Stone M. J. et al (Biochem. J. (1995) 310, 605-614) describe the expression of the surface domain of TF (truncated TF) in *Saccharomyces cerevisiae*. For TF purification, cultures were loaded onto an immunoaffinity column conjugated with an anti-TF antibody and the protein is eluted and dialysed. This assay allowed access to milligram quantities of truncated TF.

Brucato C. L. et al. (Protein Expression and Purification 26 (2002), 386-393) describe expression of the mature full-length recombinant rabbit TF protein in *Pichia pastoris*. Purification of TF protein is carried out by immobilized metal-affinity chromatography.

There is so far no known process for preparing large quantities of biologically active, recombinant TF from yeast in high yield. Advantageously, said recombinant TF should be obtained at a high level of activity, preferably, at a level of activity suitable for therapeutical uses. Hence, it is an object of the present invention to generate useful quantities of lipidated TF protein using recombinant techniques. Advantageously, the recombinant TF protein should be useful for therapeutical applications.

SUMMARY OF THE INVENTION

In a first aspect, the invention relates to a tissue factor (TF)-bearing yeast derived microvesicle comprising (i) a yeast membrane, and (ii) a tissue factor (TF) protein or a variant thereof having pro-coagulant activity, wherein a portion of said tissue factor (TF) protein or fragment thereof having pro-coagulant activity is integrated in said membrane.

In further aspects, the invention relates to a composition comprising a TF-bearing yeast derived microvesicle, to a TF-bearing yeast derived microvesicle according as a medicament, to a pharmaceutical composition comprising a TF-bearing yeast derived microvesicle, to a TF-bearing yeast derived microvesicle for the treatment of haemorrhages in a subject and to a TF-bearing yeast derived microvesicle for treating a disease which requires promoting cellular migration and/or angiogenesis in a subject.

In a further aspect, the invention relates to a process for the manufacture of a TF-bearing yeast derived microvesicle having pro-coagulant activity of the invention, which comprises the steps of:

a) subjecting a culture of recombinant yeast cells which express TF protein or a variant thereof having pro-coagulant activity to fermentation under conditions which allow the expression of said TF protein, or fragment thereof having pro-coagulant activity;

b) pelleting the product resulting from the fermentation of step a), to render a fermentation product;

c) subjecting said fermentation product from step b) to homogenization, to render a fermentation homogenate;

d) subjecting said fermentation homogenate from step c) to separation, to render a pellet and a clarified yeast extract (CYE) containing said TF-bearing yeast derived microvesicle having pro-coagulant activity;

e) collecting said clarified yeast extract (CYE) containing said TF-bearing yeast derived microvesicle having pro-coagulant activity; and, optionally, f) if desired, isolating or purifying said TF-bearing yeast derived microvesicles having pro-coagulant activity.

In a further aspect, the invention relates to a process for the preparation of microvesicles comprising a membrane protein of interest from a eukaryotic host cell which comprises the steps of:

a) growing a culture of said eukaryotic host cell under conditions which allow the expression of said membrane protein of interest;

b) subjecting the cell fraction of the culture of a) to homogenization c) subjecting the homogenate obtained from step b) to separation, to render a pellet and a clarified cell extract containing said cell-derived microvesicles containing the membrane protein of interest and d) purifying said cell-derived microvesicles by size partitioning.

In another aspect, the invention relates to a modified tissue factor (TF) lipidated protein selected from the group of:

(i) a truncated tissue factor (TF) lacking all or part of the domain responsible for binding to FVIIa, having procoagulant activity, (ii) a TF protein mutant having pro-coagulant activity in which the domain responsible for binding to FVIIa is not functional and (iii) a TF protein mutant having pro-coagulant activity which carries at least a non-functional N-glycosylation site.

In further aspects, the invention relates to a modified TF lipidated protein according to the invention for use as a medicament, to a pharmaceutical composition comprising a modified TF lipidated protein and a pharmaceutically acceptable vehicle, to a modified TF lipidated protein for the treatment of haemorrhages in a subject and for treating a disease which requires promoting cellular migration and/or angiogenesis in a subject.

In further aspect, the invention relates to a polynucleotide sequence which codes for a truncated tissue factor (TF) lacking all or part of the domain responsible for binding to FVIIa, having pro-coagulant activity, for a TF protein mutant having pro-coagulant activity in which the domain responsible for binding to FVIIa is not functional and for a TF protein mutant having pro-coagulant activity which carries at least a non-functional N-glycosylation site.

The invention also relates to a vector which comprises a polynucleotide sequence of the invention, to a host cell which comprises a polynucleotide of the invention or the vector of the invention, and to an antibody which binds specifically to a modified TF protein of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows the map of the pTT10301 plasmid. A 1,050 bp DNA fragment containing the GPD promoter (pGPD), a unique BamHI site and the PGK terminator (PGKt) was excised from plasmid pG1 after digestion with HindIII and XbaI DNA restriction enzymes. The DNA fragment was isolated by agarose gel electrophoresis and purified with a DNA extraction kit (Qiagen) and cloned into the Yep352 plasmid, previously digested with HindIII and XbaI. The resulting plasmid pTT10301 plasmid was grown in $E.$ $coli$ and purified with the commercial DNA purification JETstar kit (Genomed Gmbh). FIG. 1B shows the restriction endonuclease analysis of the generated pTT10301 plasmid.

FIG. 3 shows the cDNA sequence of the human TF protein (Gene Bank #BC011029). The open reading frame (ORF) is framed as well as the start (ATG) and end (TAA) codons. The cDNA sequence includes the four domains (signal peptide, extracellular domain, transmembrane region and cytoplasmic tail) of the human TF (hTF) protein. The arrows show the annealing location of primers A [upstream primer, encoding the first four amino-acids of mature hTF lacking the signal peptide and containing an initiation codon ATG in frame with TF ORF] and B [downstream primer, with the termination codon in bold], both containing a restriction BamHI site (underlined).

FIG. 4B shows the restriction analysis of the generated pTT10302 plasmid.

FIG. 19 shows the cDNA sequence of the human TF protein (Gene Bank #BC011029). The open reading frame (ORF) is framed as well as the start (ATG) and end (TAA) codons. The cDNA sequence includes the four domains (signal peptide, extracellular domain, transmembrane region and cytoplasmic tail) of the human TF (hTF) protein. The arrows show the annealing location of primers A [upstream primer, encoding the first four amino-acids of mature hTF lacking the signal peptide and containing an initiation codon ATG in frame with TF ORF] and E [downstream primer; histidines coding nucleotides in bold], both containing a restriction BamHI site (underlined).

FIG. 20A shows that the DNA fragment obtained from the PCR reaction was digested with BamHI and cloned into the pTT10301 plasmid, previously digested with BamHI and dephosphorylated. The resulting plasmid pTT10303 was grown in E. coli and purified with the commercial DNA purification JETstar kit (Genomed Gmbh). FIG. 20B shows the restriction analysis of the generated pTT10303.

FIG. 22A shows SDS-PAGE and Coomassie blue staining of extracts from yeast yTT10300 (lane 1), yTT10301expressing rTF (lane 2), or yTT10302 (clone #5) expressing rTF-his-tag (lane 3). Positive control corresponding to 5 ng of a rTF produced in E. coli (lane 4). FIG. 22B is a Western-blot analysis of the same samples shown in FIG. 17A, using the purified mouse anti-human CD142 monoclonal antibody (BD Biosciences Pharmingen). Molecular weight markers in kDa are shown at the left side of the figure.

FIG. 27A shows the schematic representation of a TF-bearing yeast derived microvesicle of the invention comprising a yeast derived membrane (1) and a TF protein (2) (or a fragment thereof having pro-coagulant activity) integrated in said yeast derived membrane (1). The intra-microvesicle space (3) and the extra-microvesicle space (4) are represented. FIGS. 27B and 27C show the basic architecture of a TF-bearing yeast derived microvesicle of the invention. The lipids of the yeast derived membrane lipid bilayer are amphipathic; they have hydrophilic polar heads (5) pointing the extra-microvesicle space (4) and two hydrophobic hydrocarbon tails (6) pointing the intra-microvesicle space (3). In the embodiment shown in FIG. 27B, the N-terminal domain of the TF protein (2), or fragment thereof having pro-coagulant activity, faces the extra-microvesicle space (4). In the embodiment shown in FIG. 27C the N-terminal domain of the TF protein (2), or fragment thereof having pro-coagulant activity, faces the intra-microvesicle space (3).

FIG. 28 shows the cDNA sequence of the human TF protein (Gene Bank #BC011029). The open reading frame (ORF) is framed as well as the start (ATG) and end (TAA) codons. The cDNA sequence includes the four domains (signal peptide, extracellular domain, transmembrane region and cytoplasmic tail) of the human TF (hTF) protein. The arrows show the annealing location of primers F [upstream primer, encoding the first four amino-acids of mature hTF lacking the signal peptide and containing an initiation codon ATG in frame with TF ORF] and E [downstream primer; histidines coding nucleotides in bold], both containing a restriction BamHI site (underlined).

DETAILED DESCRIPTION OF THE INVENTION

Figure 1:
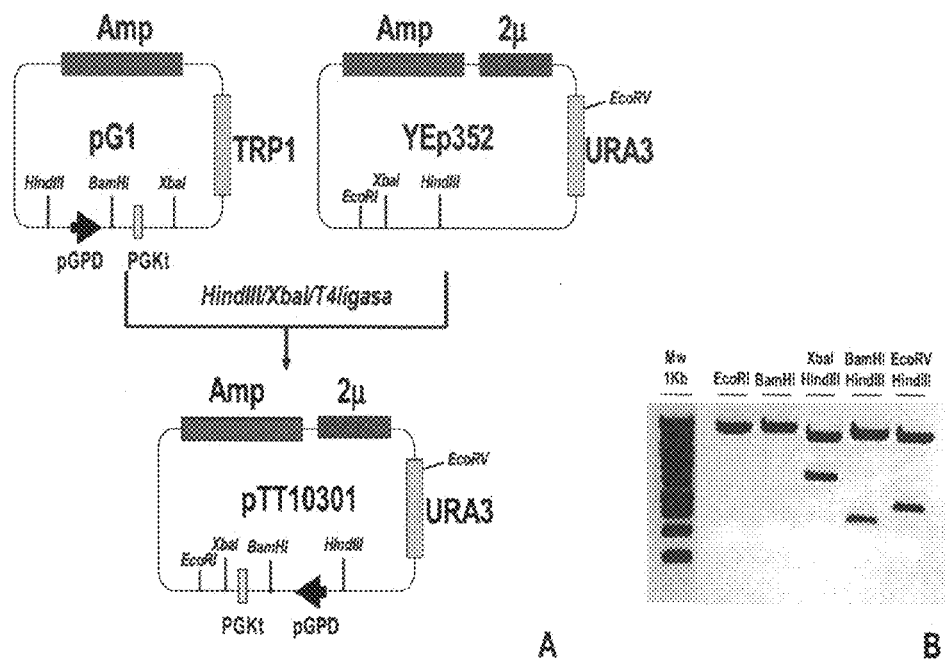
FIG. 1 shows the cloning strategy for the generation of pTT10301.

TF-Bearing Yeast Derived Microvesicle of the Invention

In an aspect, the invention relates to a tissue factor-bearing yeast derived microvesicle, hereinafter referred to as "TF-bearing yeast derived microvesicle of the invention", comprising (i) a yeast membrane, and (ii) a tissue factor (TF) protein or a variant thereof having pro-coagulant activity, wherein a portion of said tissue factor (TF) protein or variant thereof having pro-coagulant activity is integrated in said lipid bilayer. The TF-bearing yeast derived microvesicle of the invention has pro-coagulant activity and, so, it can be used as a medicament for the treatment of hemorrhages in a subject.

As used herein, the term "yeast derived microvesicle" refers to a small and closed compartment, which is substantially composed by membranes, or fragments thereof, from yeast cells. A membrane refers, in general, to an organized layer of a few molecules thick forming the boundary of a cell (i.e., the cell or plasma membrane) or the boundaries of intracellular organelles.

Component (i) of the TF-bearing yeast derived microvesicle of the invention is a yeast membrane which will proceed from the yeast cells used in the production of the TF-bearing yeast derived microvesicle of the invention. Typically a membrane is composed of two oriented lipid layers (i.e., a lipid bilayer) in which proteins can be embedded. A lipid bilayer, which is the basic structure of the membranes of a cell, is usually formed by amphipathic molecules (e.g. phospholipids, fatty acids etc.) in an aqueous environment, each molecule being oriented with the hydrophilic group on the outside of the layer and the hydrophobic group to the interior of the layer. Typically, proteins are embedded in the lipid bilayer; so, the TF-bearing yeast derived microvesicle of the invention contains proteins from yeast cells membranes, which are normally integrated in said yeast cells membranes.

In a particular embodiment, said yeast derived microvesicle derives from yeast cells membranes or fragments thereof, such as, for example, yeast cells plasma membranes or fragments thereof. In another particular embodiment, said yeast derived microvesicle derives from intracellular yeast cells organelles membranes, or fragments thereof, such as nucleus, Golgi apparatus, Endoplasmic reticulum, etc.

Said yeast derived microvesicles will proceed, in general, from the yeast cells used in the production thereof (e.g., after subjecting the yeast fermentation product to an homogenization treatment as shown in the process disclosed in Example 1). Practically any yeast cell can be used for producing said yeast derived microvesicles, advantageously non-flocculent yeast cells, and, preferably, a yeast cell classified as a "Generally Regarded as Safe" (or GRAS) yeast cell by the Federal Drug Administration (FDA) for human consumption, since said GRAS approved substances do not require pre-market approval by the FDA because they are substantially inocuous for animals including human beings. Illustrative, non limitative, examples of yeast cells that can be used in the process for producing the TF-bearing yeast derived microvesicle of the invention are the so-called liquor yeast species which produce alcohol, carbonic acid gas, Baker's yeast, and the like by metabolizing a brewing material liquid. Specifically, preferred yeast cells include yeast cells from *Saccharomyces* sp., etc., for example, *S. cerevisiae* strain T73 ura3⁻, a derivative of *S. cerevisiae* T73 strain, a strain widely used in wine production (Example)) or *Pichia* sp.

Component (ii) of the TF-bearing yeast derived microvesicle of the invention is a tissue factor (TF) protein or a variant thereof having pro-coagulant activity.

As used herein "TF variant" relates to any polypeptide derived from TF by substitution, insertion or addition of one or more amino acids.

In a particular embodiment, said component (ii) of the TF-bearing yeast derived microvesicle of the invention is a TF protein.

The term "tissue factor" or "TF" as used herein includes native or wild-type (wt) TF of any animal species, including human beings, as well as mutants thereof maintaining at least one of the functions of said wt TF, advantageously, a function of the wt TF concerning coagulation.

TF protein is an integral membrane glycoprotein that is widely distributed in the animal kingdom which, as it is naturally found, consists of a proteinaceous component (protein) and a phospholipid. Some glycosylation sites are present in the TF protein for the addition of oligosaccharide side chains to said protein to render a TF protein in a glycosylated form. Depending on the glycosylation degree, different glycosylated forms of TF protein can be available. In this regard, mature TF contains three potential N-linked glycosylation sites of the form Asn-Xaa-Ser/Thr ($Asn^{11}$-$Leu^{12}$-$Thr^{13}$, $Asn^{124}$-$Val^{125}$-$Thr^{126}$ and $Asn^{137}$-$Asn^{138}$-$Thr^{139}$). N-linked glycosylation in yeast typically involves an inner core of about ten mannose residues, linked to the asparagine via two GlcNAc residues, and a branched outer chain of 50-100 mannose residues: Therefore N-linked glycosylation could potentially add as many as 300 mannose residues to TF, an increase in molecular mass in about 60 kDa. In addition, it is also possible that several mannose residues could be attached to various (more than 25) O-linked glycosylation sites. In a particular embodiment, the TF-bearing yeast derived microvesicule of the invention comprises a glycosylated TF protein. As used herein the term "glycosylated" includes any degree of glycosylation.

Figure 27:
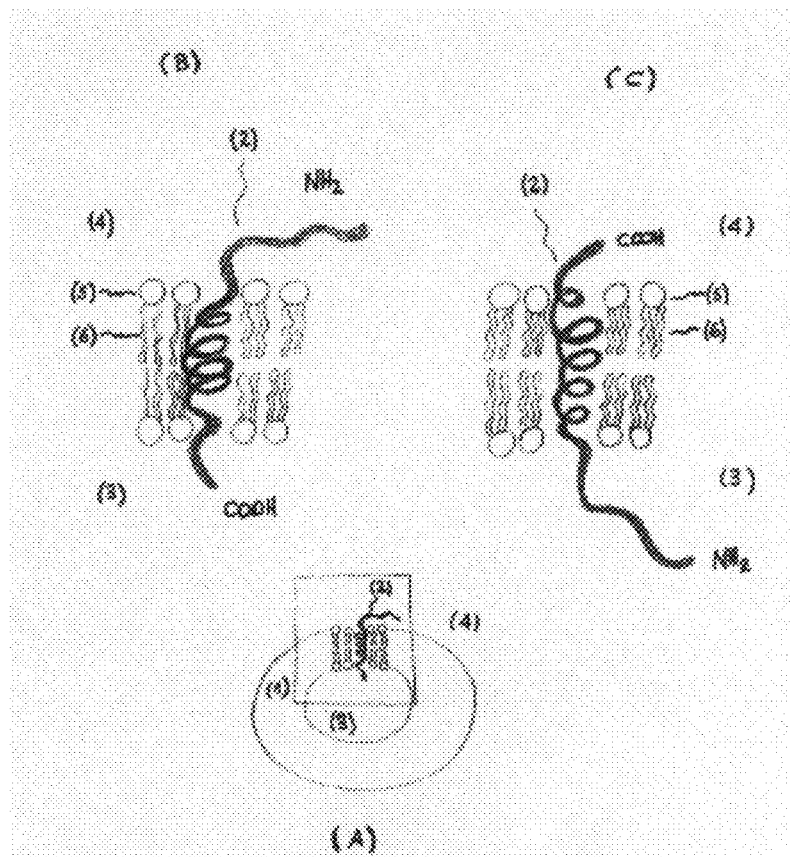
FIG. 27 is a schematic representation of a TF-bearing yeast derived microvesicle of the invention.

A schematic representation of a TF-bearing yeast derived microvesicle of the invention is depicted in FIG. 27.

The TF protein has a domain structure, i.e., it is a protein with independent functional regions. In a particular embodiment, said TF protein is the human TF (hTF) protein. Each one of the domains of the hTF protein has unique structural and functional characteristics: (1) a signal peptide or a region with a 32 amino acid leader sequence that is post-translationally processed when the protein is processed from the immature to the mature form; (2) an N-glycosylated hydrophilic extracellular domain comprising about 219 terminal amino acids; (3) a fragment of about 23 amino acids, mainly hydrophobic, which are believed to be the transmembrane domain amino acids; and (4) the 21-amino acid carboxyl end which are believed to be the amino acids forming part of the protein cytoplasmic fragment. The domain structure of the hTF protein allows the production of, for example, the extracellular domain of the protein or functional fragments thereof. The amino acid sequence of the hTF protein is known and may be consulted in protein data bases such as, for example, NCBI (hTF, Access number: P13726).

In addition, the TF protein may be a member of a fusion protein, said fusion protein containing a first region comprising the TF protein bound to a second region comprising another peptide or protein. Said second region may be bound to the amino-terminus region of said TF protein, or, alternatively said second region may be bound to the carboxyl-terminus region of said TF protein. Both first and second regions may be directly bound each other or may be bound through a linker polypeptide between said first and second regions.

In a particular embodiment, said fusion protein comprises a TF protein and a tag, usually a peptide tag, bound to the C-terminal or N-terminal domain of said TF protein. Said tag is generally a peptide or amino acid sequence which can be used in the isolation or purification of said fusion protein. Thus, said tag is capable of binding to one or more ligands, such as, for example, one or more ligands of an affinity matrix such as a chromatography support or bead with high affinity. An example of said tag is a histidine tag (His-tag or HT), such as a tag comprising 6 residues of histidine (His6 or H6), which can bind to a column of nickel ($Ni^{2+}$) or cobalt ($Co^{2+}$) with high affinity. His-tag, as shown in Examples 2 and 3, has the desirable feature that it can bind its ligands under conditions that are denaturing to most proteins and disruptive to most protein-protein interactions. Thus, it can be used to remove the bait protein tagged with H6 following the disruption of protein-protein interactions with which the bait has participated.

Additional illustrative, non-limitative, examples of tags useful for isolating or purifying a fusion protein include Arg-tag, FLAG-tag, Strep-tag, an epitope capable of being recognized by an antibody, such as c-myc-tag (recognized by an anti-c-myc antibody), SBP-tag, S-tag, calmodulin binding peptide, cellulose binding domain, chitin binding domain, glutathione S-transferase-tag, maltose binding protein, NusA, TrxA, DsbA, Avi-tag, etc. (Terpe K., Appl. Microbiol. Biotechnol. (2003), 60:523-525), an amino acid sequence such as Ala-His-Gly-His-Arg-Pro (SEQ ID NO: 2); Pro-Ile-His-Asp-His-Asp His-Pro-His-Leu-Val-Ile-His-Ser (SEQ ID NO: 3), Gly-Met-Thr-Cys-X-X-Cys (SEQ ID NO: 4); β-galactosidase, etc.

In a particular embodiment, said tag is a His-tag bound to the C-terminal domain of said TF protein. In another embodiment, said tag is a His-tag bound to the N-terminal domain of said TF protein.

Said fusion protein also has pro-coagulant activity. The pro-coagulant activity of said fusion protein can be assayed as previously mentioned, e.g., by any of the coagulation assays mentioned in Example 4, such as by an in vitro coagulation assay in plasma, or by an in vitro coagulation assay in non-anticoagulated whole blood, or by an in vivo assay in a severe hemorrhage animal model or by an in vivo assay in a lethal hemorrhage animal model, such as those assays mentioned in Example 4.

Said fusion protein may be obtained by conventional means, e.g., by means of gene expression of the nucleotide sequence encoding for said fusion protein in a suitable yeast cell. The eventual tag can be used, if desired, for the isolation or purification of said fusion protein.

In another particular embodiment, said component (ii) of the TF-bearing yeast derived microvesicle of the invention is a fragment of TF having pro-coagulant activity.

As used herein, the term "fragment of TF protein having pro-coagulant activity" includes any peptide from TF which, when it is lipidated, has pro-coagulant activity. The pro-coagulant activity of a TF fragment can be easily assayed by any conventional assay, e.g., by any of the coagulation assays mentioned in Example 4. By way of illustration only, the pro-coagulant activity of a TF fragment can be determined by an in vitro coagulation assay in plasma, or by an in vitro coagulation assay in non-anticoagulated whole blood, or by an in vivo assay in a severe hemorrhage animal model or by an in vivo assay in a lethal hemorrhage animal model, such as those assays mentioned in Example 4.

The amino acid sequence of said fragment of TF protein having pro-coagulant activity can be identical to that of the corresponding fragment of the native TF protein, or, alternatively, or it may have insertions, deletions or modifications of one or more amino acids with respect to the native TF protein, provided that the resultant fragment of TF protein has pro-coagulant activity.

In a particular embodiment, the fragment of TF having pro-coagulant activity comprises a mature TF protein. The term "mature TF" as used herein, refers to the TF protein which amino acid sequence lacks the signal peptide. In a preferred embodiment, said mature TF protein comprises the human mature TF protein. Further, in a specific embodiment, said human mature TF protein has the amino acid sequence shown in SEQ ID NO: 1.

In another particular embodiment, the fragment of TF protein having pro-coagulant activity is a TF protein wherein all or part of the domain responsible for binding to FVIIa is missing, and, consequently, the resultant protein is unable to bind to FVIIa. Said fragment of the TF protein having pro-coagulant activity but lacking the domain responsible for binding to FVIIa is sometimes referred to as "truncated TF protein" or "truncated form of TF" in this description. By extension, said "truncated TF protein" may include TF protein mutants having pro-coagulant activity in which the domain responsible for binding to FVIIa is not functional.

In a particular embodiment, said truncated TF protein comprises the interaction domain to Factor X, the transmembrane region and the citoplasmic tail and lacks, partially or totally, the domain responsible for binding to FVIIa. Further, in a specific embodiment, said truncated TF protein is a truncated form of the human TF protein containing the interaction domain to Factor X (aa 174-251), the transmembrane region (aa 252-274), and the cytoplasmic tail (aa 275-295) and an extra histidine tag (Example 3). Inventors have now surprisingly discovered that said truncated form of TF protein, lacking the domain responsible for binding to FVIIa, has pro-coagulant activity (Example 4, Table 3).

The authors of the present invention have surprisingly found that said fragment of TF, lacking all or part of the domain responsible for binding to FVIIa, has pro-coagulant activity. This result was surprising since it is well-known that TF acts in the blood coagulation extrinsic pathway by being exposed on adventitia cells at the lesion site binds to circulating coagulation Factor VII/activated coagulation Factor VII (FVII/FVIIa) to form the TF::FVIIa complex which, in the presence of calcium, act as a substrate so that FX activation takes place. It is accepted that in the event of a hemorrhage produced by a vascular lesion, coagulation is triggered due to extrinsic pathway activation involving the interaction of TF with its ligand, FVII/FVIIa.

In another embodiment, the modified TF contains one or more mutations in the domain responsible for binding to FVIIa which result in that the modified TF is unable to bind to said FVIIa or does it with a substantially reduced affinity. Point mutations in the FVIIa binding domain of TF which are known to abolish binding to said FVIIa are known in the art (e.g. those described by Kelley, R. F. et al., 1995, Biochemistry, 34:10383-10392 whose contents are therefore incorporated by reference in its entirety).

The authors of the present invention have also observed that the procoagulant activity of TF as well as its expression in yeast host cells is increased when said TF carries mutations in the glycosylation sites that prevent the attachment of at least one of the three N-linked glycosyl chains found in the wild-type TF. Thus, in a particular embodiment, the TF-bearing yeast derived microvesicule of the invention comprises a non-glycosylated fragment of TF protein having pro-coagulant activity. As mentioned above, the term "glycosylated" includes any degree of glycosylation. In a preferred embodiment, the TF variant is a polypeptide wherein at least one of the N-glycosylation sites of TF has been modified so as to render it non-functional, i.e. uncapable of serving as acceptor site for the addition of glycoside chains. The N-glycosylation sites in the TF sequence which can modified are those previously mentioned, i.e. the $Asn^{11}$-$Leu^{12}$-$Thr^{13}$ site, the $Asn^{124}$-$Val^{125}$-$Thr^{126}$ site and/or the $Asn^{137}$-$Asn^{138}$-$Thr^{139}$ site. Any modification of the N-glycosylation consensus regions is suitable as long as the addition of the N-linked glycosyl chain is abolished or substantially inhibited. Preferably, the modification is introduced in the Asn residue corresponding to positions 11, 124 and/or 137 in the mature human TF, since this is the residue that serves as acceptor for the attachment of the glycosyl, chain. As used in the present invention "sites corresponding to sites 11, 124 and/or 137 in the mature human TF" relates to the N-glycoylsation sites in other TF orthologs which might appear at a different position in the polypeptide chain but which match with the N-glycosylation sites in the mature human TF when the human and the ortholog sequences are aligned based on sequence similarity. A suitable algorithm for alignment or multiple TF sequences and, thus, for identifying N-glycosylation sites in TF orthologs corresponding to the sites in human mature TF is the PILEUP program which forms part of the GCG Software Package (Genetics Computer Group, Program Manual for the GCG Package, Version 7, Madison, Wis.). PILEUP creates a multiple sequence alignment from a group of related sequences using progressive, pair wise alignments to show relationship and percent sequence identity. It also plots a tree or dendrogram showing the clustering relationships used to create the alignment. PILEUP uses a simplification of the progressive alignment method of Feng and Doolittle, J. Mol. Evol., 35: 351-360 (1987). Preferably, the Asn residues at positions 11; 124 and/or 137 are substituted by Ala. Thus, in a preferred embodiment, the TF variant which forms part of the microvesicles is selected from the group of N11A, N124A, N137A, N11A and N124A, N11A and N137A, N124A and N137A and N11A, N124A and N137A in the human mature TF. In any other TF ortholog, the mutations will take place in the corresponding Asn residues that form the N-linked glycosylation consensus sites.

In addition, as in the case of the TF protein, the fragment of TF protein having pro-coagulant activity used in carrying out this invention may be a member of a fusion protein, said fusion protein containing a first region comprising said TF protein fragment thereof having pro-coagulant activity, bound to a second region comprising another peptide or protein. Said second region may be bound to the amino-terminus region of said TF protein fragment, or, alternatively said second region may be bound to the carboxyl-terminus region of said TF protein fragment. Both first and second regions may be directly bound or bound through a linker polypeptide between said first and second regions.

In a particular embodiment, said fusion protein comprises a fragment of TF protein having pro-coagulant activity and a tag bound to the C-terminal or N-terminal domain of said TF protein fragment. Said tag is generally a peptide or amino acid sequence which can be used in the isolation or purification of said fusion protein. Illustrative, non-limitative examples of tags suitable for the production of this fusion protein include those mentioned previously in connection with the fusion protein wherein the first region was a TF protein. In a particular embodiment, said tag is a His-tag bound to the C-terminal domain of said TF protein or fragment thereof having pro-coagulant activity. In another embodiment, said tag is a His-tag bound to the N-terminal domain of said TF protein or fragment thereof having pro-coagulant activity. This fusion protein also has pro-coagulant activity, the pro-coagulant activity thereof can be assayed as previously mentioned, e.g., by any of the coagulation assays mentioned in Example 4.

According to the invention, a portion of said TF protein or fragment thereof having pro-coagulant activity is integrated in said yeast membrane. Normally, said portion comprises the lipophilic region of said protein or fragment (i.e., the central domain of TF), whereas the hydrophyllic regions thereof (i.e., the amino-terminus region and the carboxyl-terminus region of said TF protein) face the exoplasmic or the endoplasmic side of the membrane. Information concerning the lipophilic and hydrophylic regions of TF protein can be obtained from FIG. 2 which shows a hydropathy plot of the TF protein. Example 1, Section 1.4 shows that said TF protein or fragment thereof having pro-coagulant activity is integrated in the membrane (i.e., it is a membrane associated protein).

In a particular embodiment, the N-terminal domain of the TF protein or of the fragment thereof having pro-coagulant activity faces the exoplasmic side of said membrane, whereas in another particular embodiment the N-terminal domain of said TF protein or fragment having pro-coagulant activity faces the endoplasmic side of said membrane (FIG. 27).

The size of the TF-bearing yeast derived microvesicle of the invention can vary within a relatively broad range, usually, said size is equal to or lower than 1 µm, typically equal to or lower than 0.1 am. In a particular embodiment, the size of the TF-bearing yeast derived microvesicles of the invention ranges from 0.1 to 0.01 µm, as determined by electron microscopy (Example 1, Section 1.6).

Process for Producing TF-Bearing Yeast Derived Microvesicle of the Invention

TF-bearing yeast derived microvesicles of the invention can be obtained, typically, by recombinant techniques. Thus, in other aspect, the invention relates to a process for the manufacture of a TF-bearing yeast derived microvesicle having pro-coagulant activity (i.e., the TF-bearing yeast derived microvesicle of the invention), hereinafter referred to as the "process of the invention", which comprises:
  a) subjecting a culture of recombinant yeast cells which express TF protein or a fragment thereof having pro-coagulant activity to fermentation under conditions which allow the expression of said TF protein, or fragment thereof having pro-coagulant activity;
  b) pelleting the product resulting from the fermentation of step a), to render a fermentation product;
  c) subjecting said fermentation product from step b) to homogenization, to render a fermentation homogenate; and
  d) subjecting said fermentation homogenate from step c) to separation, to render a pellet and a clarified yeast extract (CYE) containing said TF-bearing yeast derived microvesicle having pro-coagulant activity (i.e., the TF-bearing yeast derived microvesicle of the invention);
  e) collecting said clarified yeast extract (CYE) containing said TF-bearing yeast derived microvesicle having pro-coagulant activity; and, optionally,
  f) if desired, isolating or purifying said TF-bearing yeast derived microvesicles having pro-coagulant activity.

Recombinant yeast cells which express TF protein or a fragment thereof having pro-coagulant activity can be obtained by conventional recombinant methods known by the skilled person in the art. Briefly, a yeast cell is transformed with a yeast expression vector comprising the nucleotide sequence coding for TF protein or a fragment thereof having pro-coagulant activity, operatively linked to a yeast-functional promoter.

The cDNA coding for TF protein or a fragment thereof having pro-coagulant activity can be amplified by the polymerase chain reaction (PCR) using a cDNA library as template and the appropriate primers. Example 1 discloses the amplification of the cDNA coding for the mature hTF protein; Example 2 discloses the amplification of the cDNA coding for the mature hTF protein with 18 extra nucleotides (coding for six histidines) at the 3' end; and Example 3 discloses the amplification of the cDNA coding for a truncated form of the hTF protein (TTF), containing the interaction domain to Factor X, the transmembrane region, and the cytoplasmic tail with 18 extra nucleotides (coding for six histidines) at the 3'end.

A "vector", as used herein, refers to a nucleic acid molecule capable of transporting another nucleic acid to which it has been linked. The term "yeast expression vector" as used herein refers to DNA expression constructs, e.g., nucleic acid segments, plasmids, cosmids, phages, viruses or virus particles capable of synthesizing the subject proteins encoded by their respective recombinant genes (i.e., TF protein or a fragment thereof having pro-coagulant activity) carried by the vector in a yeast. Alternatively, nucleic acid segments may also be used to create transgenic yeast cells, using non-directional or homologous recombination, in which the gene or genes of interest are stably integrated into the yeast genome. Normally, the yeast expression vector comprises the nucleotide sequence coding for TF or a fragment thereof having pro-coagulant activity operatively linked to a promoter which is functional in yeast cells (i.e., a yeast-functional promoter).

Vectors for use with the invention are, for example, vectors capable of autonomous replication and/or expression of nucleic acids to which they are linked in yeast cells. In the present specification, the terms "plasmid" and "vector" are used interchangeably as the plasmid is the most commonly used form of a vector. Moreover, the invention is intended to include such other forms of expression vectors that serve equivalent functions and which become known in the art subsequently hereto. Said yeast expression vector may be a yeast episomal expression vector or a yeast integrative expression vector, and they can be obtained by conventional techniques known for the skilled person in the art.

Thus, in an embodiment, said yeast expression vector is a yeast episomal expression vector. The term "yeast episomal expression vector" as used herein refers to an expression vector that is maintained as an extra-chromosomal DNA molecule in the yeast cytoplasm. In a particular embodiment, said yeast episomal expression vector, in addition to the nucleotide sequence coding for TF protein or a fragment thereof having pro-coagulant activity operatively linked to a yeast-functional promoter, further comprises: (i) a yeast selection gene; (ii) a yeast replication origin; (iii) a bacterial selection gene; and (iv) a yeast transcription termination signal. Advantageously, said yeast episomal expression vector further comprises a unique restriction site for cloning the selected gene (TF protein or a fragment thereof having pro-coagulant activity) under the control of the yeast-functional promoter and followed by the yeast transcription termination signal.

Practically any yeast-functional promoter, yeast selection gene, yeast replication origin, bacterial selection gene, yeast transcription termination signal, and restriction site for cloning, can be used in the manufacture of said yeast episomal expression vector; nevertheless, in a particular embodiment the glyceraldehyde-3-phosphate dehydrogenase promoter (pGPD) is used as the yeast-functional promoter, in another particular embodiment, the URA3 gene (URA3) is used as yeast selection gene; in another particular embodiment, the yeast 2 microns (2µ) replication origin is used as the yeast replication origin; in another particular embodiment, the ampicillin resistance gene (Amp) is used as the bacterial selection gene; and in another particular embodiment, the transcription termination signal of the phosphoglycerate kinase (PGKt) is used as the specific yeast transcription termination, signal. Thus, in a specific embodiment (Examples 1-3), the yeast episomal expression vector comprises (i) the URA3 gene; (ii) the Amp gene for selecting and propagating the vector in *E. coli*; (iii) the yeast 2µ replication origin; (iv) the pGPD; (v) the specific yeast transcription termination signal of PGKt; and (vi) a unique BamHI restriction site that allows cloning of selected genes under the control of the pGPD, and followed by the PGKt sequence.

In other embodiment, said yeast expression vector is a yeast integrative expression vector. The term "yeast integrative expression vector" as used herein refers to a vector which is capable of integrating into the yeast genome. In a particular embodiment, said yeast integrative expression vector comprises: (i) a bacterial selection gene; and (ii) an expression cassette inserted in a yeast selection gene, said expression cassette further comprising a yeast-functional promoter, a yeast transcription termination signal and a unique restriction site for cloning the selected gene (TF protein or a fragment thereof having pro-coagulant activity).

Practically any bacterial selection gene, expression cassette inserted in a yeast selection gene, yeast-functional promoter, yeast transcription termination signal, and unique restriction site for cloning the selected gene, can be used in the manufacture of said yeast integrative expression vector; nevertheless, in a particular embodiment, the ampicillin resistance gene (Amp) is used as the bacterial selection gene; in another particular embodiment, the expression cassette pGPD-BamHI-PGKt inserted in the central region of the URA3 gene is used as expression cassette containing a yeast-functional promoter (pGDP), a yeast transcription termination signal (PGKt), and unique restriction site (BamHI) or cloning the selected gene in the central region of the URA3 gene.

Virtually any yeast cell susceptible of being transformed with said yeast expression vector comprising the nucleotide sequence coding for TF protein or a fragment thereof having pro-coagulant activity, operatively linked to a yeast-functional promoter, can be used in the present invention. Transformation of yeast cells with said yeast expression vector can be carried out by conventional means known by the skilled person in the art (Sambrook et al., 2001, Molecular Cloning: A Laboratory Manual).

In a preferred embodiment, said yeast is a non-flocculent yeast (i.e., yeasts cells which when they are dispersed in a fermentation process do not flocculate (aggregate)). Advantageously, said yeast cell is a GRAS yeast cell. Illustrative, non limitative, examples of yeast cells that can be used in the process of the invention are the so-called liquor yeast species (yeasts used for making a liquor) which produce alcohol, carbonic acid gas, baker's yeast, and the like by metabolizing a brewing material liquid. Specifically, preferred ones are selected from *S. cerevisiae*. Examples of such liquor yeast include beer yeast cells, wine yeast cells, and sake yeast cells. In a preferred embodiment of the invention, the yeast cell is a wine yeast cell, such as *S. cerevisae* T73 ura3⁻ (Examples 1-3).

Once the yeast cell is transformed, the next step consists in subjecting a culture of recombinant yeast cells which express TF protein or a fragment thereof having pro-coagulant activity to fermentation under conditions which allow the expression of said TF protein, or fragment thereof having pro-coagulant activity. In a particular embodiment, said yeast cell is grown in an adequate media wherein said yeast cell can express the desired heterologous product (TF protein or fragment thereof having pro-coagulant activity). Appropriate culture media for growing yeast cells are well known for those skilled in the art and will select from the most appropriate ones in view of the yeast cells to be cultured. Any material for making a fermentation product may be used as long as it is suitable for fermentation caused by the non-agglutinative yeast cells employed, and known materials can be used at will. For example, malts, fruit juices, sugar liquids, cereal saccharified liquids, and the like are normally used alone or in combination as appropriate in the making of liquors. Also, appropriate nutrients and the like may be added thereto when necessary.

Fermentation conditions are not different from known conditions in essence and can be fixed by the skilled person in the art. In a particular embodiment, fermentation is followed by controlling the evolution of the main parameters throughout the fermentation process and it is stopped when the oxygen pressure ($PO_2$) reaches a stationary state.

The fermentation product resulting from the fermentation step a) is then pelleted by conventional methods, such as by centrifugation, and resuspended in a suitable lysis buffer prior to subjecting said product to homogenization. Yeasts can be homogenized by conventional methods, for example, by high pressure in a homogenizer to render a fermentation homogenate.

Figure 11:
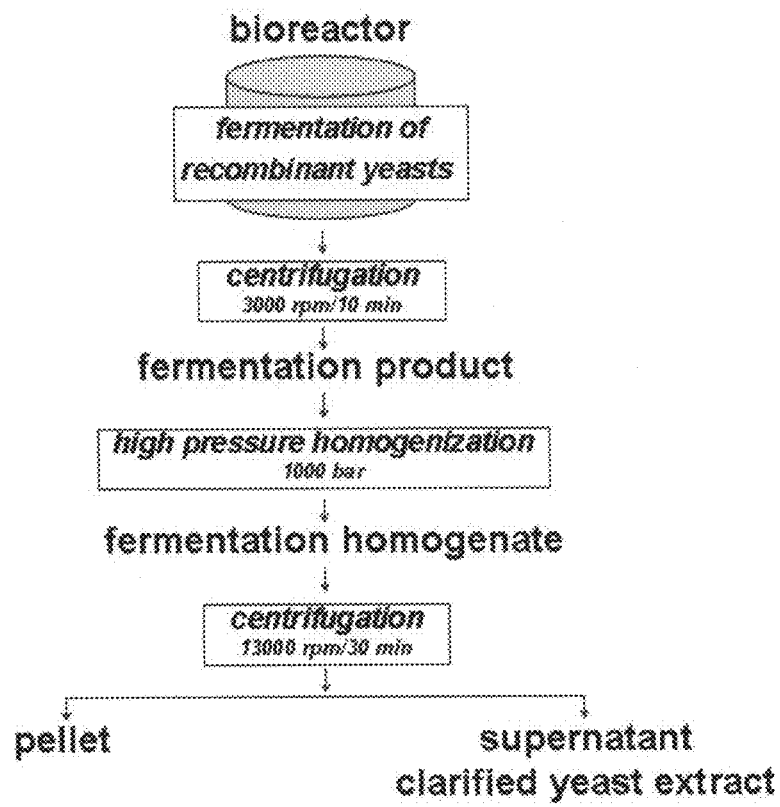
FIG. 11 is a diagram representing the general scheme of the fermentation process for producing CYE-TF.

The fermentation homogenate is then subjected to separation by conventional methods, such as by centrifugation, to render a pellet and a clarified yeast extract (CYE) containing said TF-bearing yeast derived microvesicles having pro-coagulant activity (i.e., the TF-bearing yeast derived microvesicle of the invention) which can be collected separately. A general scheme of the process of the invention is shown in FIG. 11.

The presence of TF protein or a fragment thereof having pro-coagulant activity can be determined by conventional methods, such as, by Western-blot analysis by using a specific anti-TF protein monoclonal antibody (mAb). Further, the pro-coagulant activity of the CYE can be determined by any conventional assay, such as by any of the coagulation assays mentioned in Example 4, e.g., typically by an in vitro coagulation assay in plasma or in non-anticoagulated whole blood, etc.

Further examination of CYE samples by immunoelectron microscopy showed the presence of yeast derived microvesicles labeled by anti-TF mAb on the surface of said microvesicles. Said microvesicles, which comprise TF protein or a fragment thereof having pro-coagulant activity, have also pro-coagulant activity and correspond to the TF-bearing yeast derived microvesicles of the invention.

Optionally, if desired, said TF-bearing yeast derived microvesicles having pro-coagulant activity previously obtained according to the process of the invention can be concentrated, isolated or purified by conventional methods known by the skilled person in the art. By way of illustration, affinity chromatography purification of proteins containing a peptide tag (e.g., a His-tag, etc.), either at the C- or N-terminus, is a well standardized method used to obtain highly purified preparations of a large number of proteins. As any chromatographic method, said method can be easily scaled-up. Alternative purification procedures such as immunoaffinity chromatography could be performed, although it would require the availability of well standardized stocks of specific anti-TF mono or polyclonal antibodies, especially for a scaled-up production.

Thus, the isolation and purification method will depend, among other things, on the nature of the TF protein or fragment thereof having pro-coagulant activity, i.e., if it is a fusion protein having a tag for binding to one or more ligands of an affinity matrix such as a chromatography support or bead with high affinity (e.g., a His-tag, etc.), or an epitope capable of being recognized by an antibody, such as c-myc-tag (recognized by an anti-c-myc antibody), etc.

Figure 23:
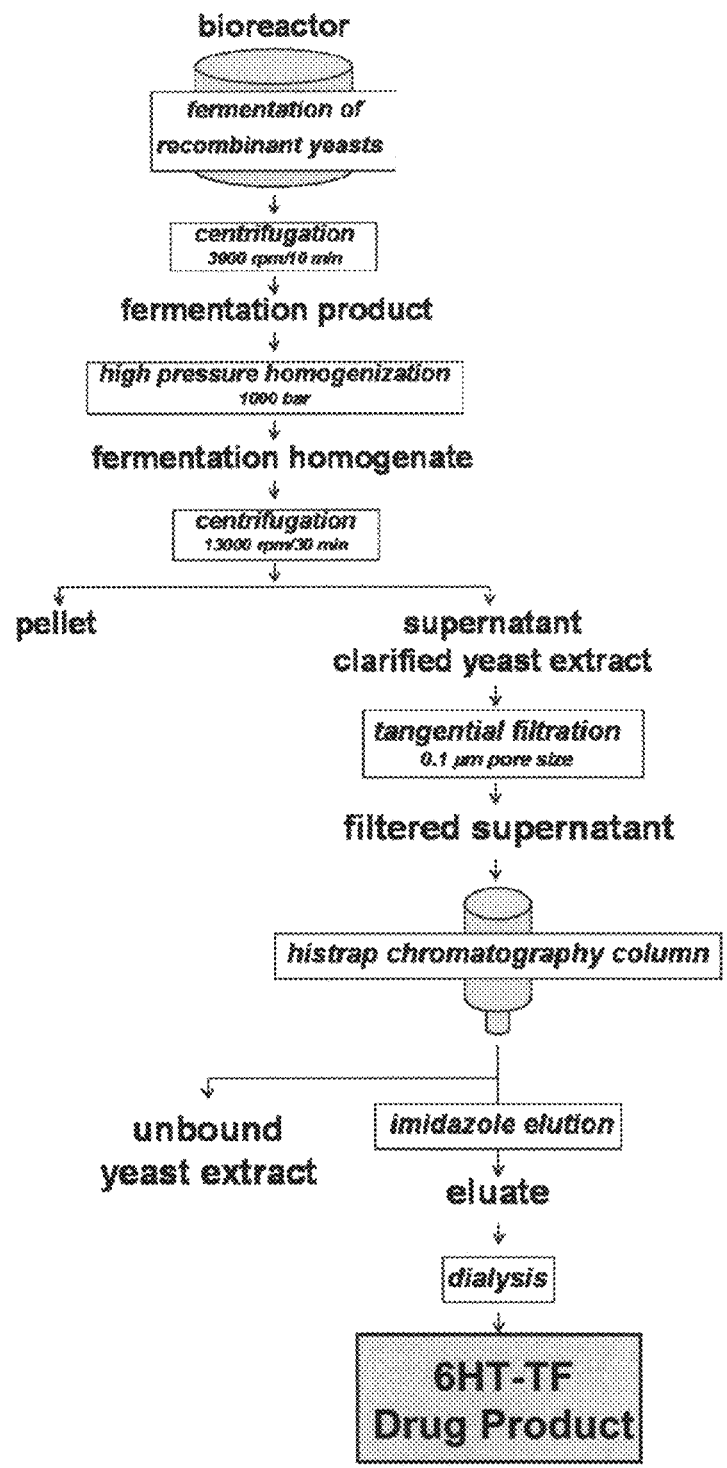
FIG. 23 schematically shows the process for 6HT-TF purification.

FIG. 23 schematically shows a method for purifying yeast derived microvesicles bearing a recombinant TF protein (or a fragment thereof having pro-coagulant activity) in the form of a fusion protein fused to an His-tag [i.e., (TF-His-tag protein)-bearing yeast derived microvesicles or "6HT-TF Drug Product" as mentioned in FIG. 23]. Briefly, a clarified yeast extract (CYE) obtained according to the process previously disclosed, containing (TF-his-tag protein)-bearing yeast derived microvesicles, is filtered (e.g., through a 0.2 μm pore size filter by tangential flow filtration) before being loaded over an appropriate affinity column (e.g., HiTrap® affinity column); then, after applying the sample, the flow-through is recovered (unbound material), and the column is subjected to several washes and, after the last wash, the (TF-His-tag protein)-bearing yeast derived microvesicles are eluted by adding to the column an appropriate buffer (e.g., a buffer containing imidazol) and the elution fractions are collected and dialyzed to render isolated or purified (TF-his-tag protein)-bearing yeast derived microvesicles.

Also, in another embodiment, the TF-bearing yeast derived microvesicles of the invention can be purified by an ÄKTA prime equipment. The ÄKTA prime is an automated liquid chromatographic system from General Electric Healthcare that can be used for the development of standard purification protocols that could be easily scaled-up for large productions. Method for the Purification of Microvesicles Comprising a Membrane Protein of Interest from a Eukaryotic Host The authors of the present invention have also observed that the vesicles present in the clarified extract derived from cells expressing TF can be further enriched using size partitioning. Without wishing to be bound by any theory, it is believed that the size partitioning using a membrane having a defined pore size allows the elimination of other components of the cell extract which are detrimental to the procoagulant activity of the protein. It is believed that the method developed by the inventors is generally applicable to the purification of any membrane protein in a eukaryotic host wherein said membrane. Thus, in another aspect, the invention relates to a process for the manufacture of a preparation of microvesicles comprising a membrane protein of interest which comprises the steps of:

(a) growing a culture of a eukaryotic host cell under conditions which allow the expression of said membrane protein of interest;
(b) subjecting the cells of the culture of (a) to homogenization,
(c) subjecting the homogenate from step (b) to separation, to render a pellet and a clarified cell extract containing said cell-derived microvesicles containing the membrane protein of interest;
(d) purifying said cell-derived microvesicles by size partitioning.

Step (a): Growing a Culture of a Eukaryotic Host Cell

The eukaryotic hosts than can be used in the context of the present invention include any cell which can be cultivated in the laboratory or in a production plant but, more preferably, a cell that can be genetically manipulated so as to allow expression within the cell of a membrane protein of interest. Hosts that can be used in the present invention include yeast (e.g., *Saccharomyces, Pichia*), insect cells, plant cells or mammalian cell systems (e.g., COS, CHO, BHK, 293,3T3).

The eukaryotic hosts used can either express their protein as part of the normal proteome or may have been modified by introducing an exogenous nucleic acid that codes for the membrane protein of interest. In both cases, the cells need to be cultured under conditions that allow expression of the membrane protein of interest. If the membrane protein of interest is encoded by a nucleic acid, this nucleic acid may be placed in a vector under the control of a promoter. Examples of well known promoters suitable for carrying out the invention include constitutive promoters such as those found in some eukaryotic viruses (polyoma virus, adenovirus, SV40, CMV, avian sarcoma virus, hepatitis B virus, metalothionein gen promoter, herpes simplex virus thymidine kinase promoter, retroviral LTR regions, immunoglobulin promoter, actin promoter, EF-1 alpha promoter as well as inducible promoters wherein expression of the downstream gene requires addition of a substance of an exogenous signal to the culture such as the tetracycline promoter, NFKappaB/UV light, Cre/lox, heat shock promoters, regulatable RNA polymerase II promoters described in WO/2006/135436 as well as tissue-specific promoters, such as the PSA promoter described in WO2006012221.

The cells are cultured using any suitable culture media. The skilled person will appreciate that the culture media has to be chosen depending on the type of host cell to be used. However, a wide variety of media for each cell type are available to the skilled person as described in Sambrook, J. et al. (Molecular Cloning: A Laboratory Manual. 2nd, ed., Cold Spring Harbor Laboratory, Cold Spring Harbor Laboratory Press, Cold Spring Harbor, N.Y. (1989)) and Ausubel et al. (Current Protocols in Molecular Biology, eds. Ausubel et al, John Wiley & Sons (1992)).

Practically any membrane protein can be expressed and purified according to the method of the invention. If the protein of interest is a membrane protein, then the protein can be expressed as such because it will be targeted to the membrane system of the host cell provided that it contains a signal sequence. Membrane proteins that can be expressed using the method of the invention include receptors, transporters such as estrogen receptors, amino acid transporters, androgen receptors, pituitary receptors, transferrin receptors, progesterone receptors, and glucose transporters. It is also possible to express soluble proteins using the method of the invention if these soluble proteins are fused to a signal sequence at the N-terminus and to a transmembrane domain at the C-terminus. In this way, the fusion protein will be inserted into the membranes of the host cell and purified in the microvesicles. In a preferred embodiment, the membrane protein of interest is rTF, a fragment thereof or an N-glycosylation mutant thereof as described above.

Step (b): Homogenization

In step (b), the cells of the culture are homogenized so as to yield an homogenate. The cells need to be separated from the culture medium using any technique available to the skilled person (centrifugation, sedimentation, filtration and the like). Once the cells are isolated, these are subjected to homogenization so as to break the cell walls and plasma membranes and to release the intracellular contents to the buffer wherein the homogenization is carried out. Rupture of the cells is carried out using any suitable method known in the art such as high pressure, nitrogen cavitation, osmotic shock using a hypotonic buffer, treatment with ultrasounds, mechanical homogeisation, enzymolytic tissue disruption methods, sonification. The homogenization is carried out in the absence of any detergent. Preferably, the homogenization is carried out by high pressure.

Step (c): Separation of Homogenate

The homogenate is then fractionated by conventional means in order separate unbroken cells and large aggregates from the contents released from the cells. Preferably, the fractionation is carried out by centrifugation at 13000×g. The supernatant obtained after the centrifugation is a clarified cell extract which comprises the soluble material as well as different microvesicle populations of different size which result from the fragmentation of the cellular membrane system.

Step (d): Size Partitioning Purification

The clarified cell extract obtained in step (c) is then fractionated based on the size of the microvesicles forming said extract so as to select those having a specific diameter size. The authors of the present invention have found that size partitioning purification techniques may be used to provide a microvesicle preparation of sufficient purity that may be therapeutically administered without additional purification steps such as chromatography and other methods previously considered necessary. Without intending to be bound by any particular theory of the invention it is believed that the steps of processing the clarified cell extracts through a size partitioning fractionation results in a product with a reduced load of contaminants. Moreover, the contaminants are of a size and nature that they may be readily separated from the microvesicle by a simple size partitioning purification step.

Membrane filtration is a well known technique in the art of bioprocessing. A membrane is defined as a structure having lateral dimensions much greater than its thickness, through which mass transfer may occur under a variety of driving forces. While many filters may be considered membranes, filters also include materials whose lateral dimensions are not usually 100 times greater than their depth and whose separation function is primarily by capture of species or particles through their depth. The most common parameters used to characterize membranes fall in three general categories. These are transport properties, pore (geometric) characteristics, and surface (or predominantly chemical) properties. Nevertheless, the transport properties depend significantly upon the pore and surface characteristics. While membrane separation can be slower and a lower volume process than other separation processes, its effectiveness makes it a method that can be used for retrieving small amounts of valuable products.

Membrane filter systems may be designed in a variety of manners to have different filtration properties. Design criteria include: operation in dead-end (with or without stirring) or cross flow mode; full or partial recovery of the feed mixture; application of an external transmembrane pressure via pumping, inert gas blanket, or evacuation of the permeate side of the device; and the use of flat sheets (either singly or multi-ply), hollow fiber bundle, or tubular membranes. Size partitioning separation methods utilize a size partitioning membrane which may be a dialysis or other similar membrane as would be known to those of ordinary skill in the art. Suitable dialysis membrane materials useful in the size partitioning membrane filtration of the invention include those commercially available such as those produced from polyethersulphone, polycarbonate, nylon, polypropylene, and the like. Suppliers of these dialysis membrane materials include Akzo-Nobel, Millipore, Inc., Poretics, Inc., and Pall Corp., by way of example.

In a preferred embodiment, the membrane-based size fractionation is tangential flow filtration (TFF), also known as "cross-flow filtration. Tangential flow filtration is a pressure driven separation process wherein fluid is pumped tangentially long the surface of a membrane. An applied pressure serves to force a portion of the fluid including contaminants through the membrane to the filtrate size. Particulates and macromolecules that are too large to pass through the membrane pores are retained on the upstream side. In contrast to normal flow filtration (NFF) techniques in which the retained components build up on the surface of the membrane, tangential flow filtration sweeps the retained components along by the flow of the fluid.

TFF is classified based on the size of components being separated. A membrane pore size rating is typically given as a micron value and indicates that particles larger than the rating will be retained by the membrane. A nominal molecular weight limit (NMWL), on the other hand, is an indication that most dissolved macromolecules with molecular weights higher than the NMWL and some with molecular weights lower than the NMWL will be retained by the membrane. A component's shape, its ability to deform, and its interaction with other components in the solution all affect retention. Different membrane manufacturers use different criteria to assign the NMWL ratings to a family of membranes but those of ordinary skill would be able to determine the appropriate rating empirically.

Ultrafiltration is one of the most widely used forms of TFF and is used to separate proteins from buffer components for buffer exchange, desalting, or concentration but may also be used for filtration of the clarified cell extracts of the invention. Typical pore sizes for microvesicle filtration range up to 0.2 to 0.1 microns. In a preferred embodiment, the TFF contains a first membrane having a pore sizes of 0.2 microns and a second membrane having a pore size of 0.1 microns so that the space between membranes accumulates microvesicles having a diameter between 0.2 and 0.1 microns.

In TFF unit operation, a pump is used to generate flow of the feed stream through the channel between two membrane surfaces. During each pass of fluid over the surface of the membrane, the applied pressure forces a portion of the fluid through the membrane and into the filtrate stream. The result is a gradient in the feedstock concentration from the bulk conditions at the center of the channel to the more concentrated wall conditions at the membrane surface. There is also a concentration gradient along the length of the feed channel from the inlet to the outlet (retentate) at progressively more fluid passes to the filtrate side. The flow of feedstock along the length of the membrane causes a pressure drop from the feed to the retentate end of the channel. The flow on the filtrate side of the membrane is typically low and there is little restriction, so the pressure along the length of the membrane on the filtrate side is approximately constant.

Membranes may be fabricated from various materials offering alternatives in flushing characteristics and chemical compatibility. Suitable materials include cellulose, polyethersulfone and other materials known to those of skill in the art. In certain embodiments polyethersulfone is used. Typical polyethersulfone membranes tend to adsorb protein as well as other biological components, leading to membrane fouling and lowered flux. Some membranes are hydrophilically modified to be more resistant to fouling such as Biomax (Millipore).

Those of skill in the art would recognize that various types of TFF modules would be useful in practice of the invention. Useful TFF modules include but are not limited to flat plate modules (also known as cassettes), spiral wound modules, and hollow fiber modules.

For any given module, key process parameters may then be readily optimized by those of ordinary skill. Such parameters include cross flow rate, transmembrane pressure (TMP), filtrate control, membrane area, and diafiltration design. Cross flow rate depends upon which module is selected. In general, a higher cross flow rate gives higher flux at equal TMP and increases the sweeping action across the membrane and reduces the concentration gradient towards the membrane surface. Many TFF applications apply a cross flow and pressure set point and the filtrate flows uncontrolled and unrestricted out of the module. This is the simplest type of operation but in some circumstances it might be desired to use some type of filtrate control beyond that achieved by simply adjusting the pressure with the retentate valve. Membrane area is selected after determining the process flow and the total volume to be processed and is also dependent upon process time.

The concentration may typically be performed by centrifugation at 2000-4500 g, such as between 2500-4000 g, or between 2750-3500 g, or between 3000-3500 g, such as at 3000 g or 3100 g or 3200 g or 3300 g or 3400 g or 3500 g.

Typically the centrifugation may be run for several hours, e.g. for more than one hour, such as for 1-10 hours.

To minimize any negative effects on the stability of the polypeptide of interest the centrifugation may in particular be performed at a temperature in the range of 2-200 C, such as in the range of 3-15 Degrees Centigrade or in the range of 3-10° C. or in the range of 3-6 Degrees Centigrade Preferred buffers for use in the TFF are phosphate buffer, HEPES buffer or TRIS buffer. However, the buffer in certain embodiments has a concentration of 5 mM to 15 mM, including concentrations of at least 5 mM, 6 mM, 7 mM, 8 mM, 9 mM, 10 mM, 11 mM, 12 mM, 13 mM, 14 mM and 15 mM, and further including mM concentrations therebetween. In certain embodiments, the buffer has a pH of between about 7.2 to 7.5. Thus in one embodiment the buffer has a pH of 7.2, 7.3, 7.4 or 7.5 or fractional pH values there between. In another embodiment, the buffer exchange buffer further comprises 0.10 M to 0.20 M NaCl and 3.5% to 4.5% sucrose.

In a preferred embodiment, the microvesicle preparation obtained after the size fractionation step is further applied to a second purification step which allows the separation of the microvesicles having the highest protein amount/activity from any other product present in the sample.

In one embodiment, said second purification step is carried out by a second size fractionation step. In another embodiment, the second purification step can be carried out by affinity chromatography. If the microvesicles contain TF, then the affinity chromatography is carried out using a compound which shows affinity for TF (e.g. an antibody). If the microvesicles contain a fusion protein comprising TF and a tag, the affinity chromatography can be carried out by using a ligand that shows affinity towards said tag. Preferably, the tag is a hexahistidine tag, in which case the affinity chromatography is carried out using a metal affinity column.

Once the microvesicle preparation has been purified, the eluate of the fractionation step is then tested for the presence of the protein of interest and those fractions containing the highest amount of protein or the highest activity are then pooled and used directly. The elution profile of the column can be tested for the presence of the protein, using any available means known in the art to detect the presence of a given protein (ELISA, Western blot, RIA and the like) or can be tested for the presence of the activity of the protein of interest. The skilled person will appreciate that the activity test will depend on the protein which is being purified. In a preferred embodiment, the protein of interest is TF and the activity which can be detected to identify those fractions containing the vesicles comprising said protein is the procoagulant activity as explained in example 5.

Therapeutical Uses of the TF-Bearing Yeast Derived Microvesicles of the Invention Different assays have shown that the TF-bearing yeast derived microvesicles of the invention show pro-coagulant activity. Effectively, Example 4 includes:

a) in vitro assays demonstrating that the TF-bearing yeast derived microvesicles of the invention cause fibrin clot formation and blood coagulation in both healthy and patient conditions; namely, said assays show that TF-bearing yeast derived microvesicles of the invention are able to coagulate:

plasma from healthy subjects (coagulation assays in plasma);

plasma deficients in FVIII, in FIX or in FXI (coagulation assays in plasma);

plasma from acquired platelet deficiency (coagulation assays in Thrombocytopenic plasma);

plasma from FXI deficient plasma in the presence of an anti-FVII antibody (coagulation assays in plasma);

blood from healthy subjects (coagulation assays in non-anticoagulated whole blood); and blood from Hemophilic patients (coagulation assays in non-anticoagulated whole blood);

b) in vivo assays demonstrating that the TF-bearing yeast derived microvesicule of the invention is an agent useful for topical antihemorrhagic treatment in severe hemorrhage models (by applying directly on the blood vessel previously sectioned); namely, said assays show that said TF-bearing yeast derived microvesicle is useful as a topical haemostatic agent in non-treated and heparin treated experimental animals.

c) in vivo assays demonstrating that the TF-bearing yeast derived microvesicule of the invention is an agent useful for topical antihemorrhagic treatment in lethal hemorrhage models (by applying directly on the blood vessel previously sectioned); namely, said assays show that said TF-bearing yeast derived microvesicle is useful as a topical haemostatic agent in a lethal hemorrhage animal model by proximal section of FVIII deficient mice tails.

These results clearly show that TF-bearing yeast derived microvesicle of the invention is a pro-coagulant or antihemorrhagic agent useful for topical treatment of hemorrhages in a subject.

Thus, the TF-bearing yeast derived microvesicle of the invention can be used as a medicament, namely, as a pro-coagulant agent, or as an antihemorrhagic agent, particularly, as an antihemorrhagic agent for topical application, in the treatment of haemorrhages in a subject.

Therefore, in another aspect, the invention relates to the TF-bearing yeast derived microvesicle of the invention as a medicament. In a particular embodiment, the invention relates to the TF-bearing yeast derived microvesicle of the invention as a topical medicament with pro-coagulant (anti-hemorragic) activity suitable for treating haemorrhages in a subject.

Although the TF-bearing yeast derived microvesicle of the invention could be applied topically for treating the hemorrhage in a subject, i.e., without mixing it with a pharmaceutically acceptable vehicle, since the components of the clarified yeast extract (CYE) comprising said TF-bearing yeast derived microvesicles obtained according to the process of the invention, are substantially innocuous for a subject, in general, for administration to a subject, the TF-bearing yeast derived microvesicle of the invention will be formulated in a pharmaceutical administration form suitable for its administration, preferably, for its topical administration for topical (local) treatment of hemorrhaging.

Thus, in another aspect, the invention relates to a pharmaceutical composition, hereinafter referred to as the pharmaceutical composition of the invention, comprising a TF-bearing yeast derived microvesicle of the invention and a pharmaceutically acceptable vehicle, carrier or excipient. Said pharmaceutical composition is then formulated in a pharmaceutical administration form suitable for its administration to a subject.

Then, for its administration to a subject, the TF-bearing yeast derived microvesicles of the invention will be formulated in a pharmaceutical administration form, preferably a pharmaceutical administration form suitable for its topical administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in galenic pharmacy treatises. A review of the different pharmaceutical administration forms of drugs in general, and of their preparation processes, can be found in the book entitled "Tratado de Farmacia Galénica" ("*Galenic Pharmacy Treatise*"), by C. Faulí i Trillo, $1^{st}$ Edition, 1993, Luzán 5, S. A. of Ediciones.

Although different pharmaceutical administration forms of TF-bearing yeast derived microvesicles of the invention could be used, administering said product topically is most advantageous in practice; therefore said TF-bearing yeast derived microvesicles of the invention will be formulated in a pharmaceutical form suitable for its topical administration. Illustrative, non-limiting examples of said pharmaceutical forms include aerosols, solutions, suspensions, emulsions, gels, salves, creams, dressings, patches, ointments, mouthwashes, etc. To that end the pharmaceutical composition of the invention will include the pharmaceutically acceptable vehicles, carriers and/or excipients required for preparing the pharmaceutical administration form of TF-bearing yeast derived microvesicles of the invention for topical administration.

Therefore, in a particular embodiment, the pharmaceutical composition of the invention is a pharmaceutical composition for the topical administration of TF-bearing yeast derived microvesicles of the invention comprising said product and a pharmaceutically acceptable vehicle, carrier or excipient suitable for the topical administration of said TF-bearing yeast derived microvesicles of the invention. Illustrative, non-limitative, examples of pharmaceutically acceptable vehicles, carriers or excipients suitable for the topical administration of said TF-bearing yeast derived microvesicles can be found in galenic pharmacy treatises.

In a particular embodiment, the pharmaceutical composition of the invention comprises TF-bearing yeast microvesicles comprising human TF protein, or a fragment thereof having pro-coagulant activity, such as, for example, mature human TF or a truncated human TF (i.e., a human TF protein wherein all or part of the domain responsible for binding to FVIIa is missing or a human TF protein mutant having pro-coagulant activity in which the domain responsible for binding to FVIIa is not functional).

TF-bearing yeast derived microvesicles of the invention will be present in the pharmaceutical composition of the invention in a therapeutically effective amount. Said amount may vary within a wide range, for example, between about 1.0 pg of active protein/ml and 1.0 mg of active protein/ml, preferably between 0.05 µg of active protein/ml and 10 µg of active protein/ml, and even more preferably between about 0.1 µg of active protein/ml and 2.0 µg of active protein/ml.

The TF-bearing yeast derived microvesicle of the invention dose to be administered to the subject may vary within a very broad range, for example, between about 1.0 pg of active protein/ml and 1.0 mg of active protein/ml, preferably between 0.05 µg of active protein/ml and 10 µg of active protein/ml, and even more preferably between about 0.1 µg of active protein/ml and 2.0 µg of active protein/ml. The TF-bearing yeast derived microvesicle of the invention dose to be administered will depend on several factors, including among them the features of the TF protein or fragment thereof having pro-coagulant activity used, such as for example, its activity and biological half life, concentration of the TF protein or fragment thereof having pro-coagulant activity in the formulation, the clinical condition of the subject or patient, the hemorrhagic disorder to be treated, etc. For this reason the doses mentioned herein must be considered only as guides for a person skilled in the art, and this person must adjust the doses according to the previously mentioned variables. Nevertheless, the pharmaceutical composition of the invention can be administered one or more times a day for preventive or therapeutic purposes.

The pharmaceutical composition of the invention can be used together with other additional drugs useful in the prevention and/or treatment of a hemorrhagic diathesis (e.g., coagulation factors, human plasma, etc.) to provide a combination therapy. Said additional drugs can be part of the same pharmaceutical composition or, alternatively, they can be provided in the form of a separate composition for their simultaneous or successive (sequential in time) administration with respect to the administration of the pharmaceutical composition of the invention.

The pharmaceutical composition of the invention can be also placed on a support. Therefore, in another aspect, the invention relates to a product comprising the pharmaceutical composition of the invention and a support. The term "support", as used herein, refers to a substrate of suitable material allowing depositing the pharmaceutical composition of the invention thereon, its being carried and its release at the desired site, for example, in the site where the pharmaceutical composition of the invention exercises its therapeutic effect. Said support can be a solid support or a non-solid support, for example, a liquid support or a gaseous support. Illustrative, non-limiting examples of solid supports include dressings, band-aids, compresses, plasters, etc. Illustrative, non-limiting examples of liquid supports include gels, sprays, mouthwashes, etc. Illustrative, non-limiting examples of gaseous supports include air, propellants, etc.

In a particular embodiment, the pharmaceutical composition of the invention comprises TF-bearing yeast microvesicles comprising human TF protein, or a fragment thereof having pro-coagulant activity, such as, for example, mature human TF or a truncated human TF (i.e., a human TF protein wherein all or part of the domain responsible for binding to FVIIa is missing or a human TF protein mutant having pro-coagulant activity in which the domain responsible for binding to FVIIa is not functional).

This product comprising the pharmaceutical composition of the invention deposited on a support can be obtained by conventional methods, for example, by mixing the pharmaceutical composition of the invention and the support. The interaction between the pharmaceutical composition of the invention and the support can be a physical or chemical interaction, depending on the nature of the components of the pharmaceutical composition of the invention and on the support used.

In other aspect, the invention relates to the use of the TF-bearing yeast derived microvesicle of the invention in the manufacture of a medicament for the treatment of hemorrhages in a subject, in particular, for the topical treatment of hemorrhages in a healthy subject or in a subject with a hemorrhagic diathesis.

The term "topical treatment", as used herein, refers to the application of the treatment directly at the site where it is required, for example, in discontinuous sections of skin (cuts, etc.) and vascular tissue (ruptured vessels, etc.) in venous and arterial hemorrhage due to open wounds, surgery, etc. and in mucocutaneous and microvascular haemorrhages.

According to this invention and as shown in Example 4, the TF-bearing yeast derived microvesicles of the invention can act as a pro-coagulant or antihemorrhagic agent, and, consequently, said product can be used to treat or correct hemorrhagic disorders, particularly those hemorrhagic disorders associated with hemorrhagic diathesis.

The term "hemorrhagic diathesis" refers to the process causing a hemostasic disorder and which as a result gives rise to the occurrence of a hemorrhagic syndrome which may occasionally occur with extended and excessive bleeding. Hemorrhagic diathesis may be caused by a congenital or acquired coagulopathy and/or by a congenital and acquired platelet disorder.

The term "coagulopathy" refers to a coagulation factor disorder. This disorder may be due to a specific coagulation factor deficiency or deficit, the consequence of which will be the occurrence of a hemorrhagic syndrome, or due to a coagulation factor disorder. The coagulopathy may generally be a congenital coagulopathy or an acquired coagulopathy.

As illustrative, non-limiting examples of congenital coagulopathies, deficiencies of coagulation factors selected from coagulation Factor V (FV), coagulation Factor VII (FVII), coagulation Factor VIII (FVIII), the deficit or deficiency of which causes hemophilia A, coagulation Factor IX (FIX) the deficit or deficiency of which causes hemophilia B, coagulation Factor X (FX), coagulation Factor XI (FXI) the deficit or deficiency of which causes hemophilia C, coagulation Factor XII (FXII), coagulation Factor XIII (FXIII) and their combinations, can be mentioned.

Acquired coagulopathies may have different origins. Illustrative examples include coagulation factor synthesis deficiencies in severe hepatic failure, anticoagulant therapy (such as heparin, low molecular weight heparins, warfarin, coumarin derivatives, dicoumarins, etc.). An alternative mechanism is based on an exaggerated consumption of coagulation factors such that they are not available to form the clot in a bleeding lesion. This mechanism occurs in the disseminated intravascular coagulation syndrome or coagulopathy due to consumption occurring in multiple illnesses such as in severe sepsis damaging the microcirculation endothelium activating platelets and coagulation factors with the formation of multiple microthrombi; in blood invasion by TF such as placental release; in the retention of a dead fetus; in multiple traumas with the crushing of tissues; in poisonous snake bites, etc. In vasculitis, parietal and endothelial damage releases coagulation activators. The consumption of coagulation factors is worsened by lysis of the fibrin of numerous microthrombi due to the action of plasmin with PDF release, which are antiplatelets and anticoagulants.

The term "platelet disorder" refers to a disorder both in the number and in functional ability of platelets, the result of which is the occurrence of a hemorrhagic syndrome. Said platelet disorder may be congenital or acquired.

In a particular embodiment, said platelet disorder is a congenital platelet disorder. Illustrative, non-limiting examples of congenital platelet disorders include Glanzmann's disease, Bernard Soulier disease, Bolin-Jamieson syndrome, Wiskott-Aldrich syndrome, Paris-Trousseau-Jacobsen syndrome, X chromosome thrombocytopenia, Gray platelet syndrome, Sebastian syndrome and Fanconi anemia.

In another particular embodiment, said platelet disorder is an acquired platelet disorder. Illustrative, non-limiting examples of acquired platelet disorders include myeloproliferative disorders, such as thrombocythemia, polycythemia, chronic myelocytic leukemia, etc.; there are functional platelet disorders in myeloid metaplasia with increased bleeding time, glass bead retention defects, platelet aggregation defect, abnormal release, and platelet factor III defect. Functional platelet defects have been found in dysproteinemias in scurvy and in congenital heart disease and cirrhosis.

The terms "acquired coagulopathy" and "acquired platelet disorder" refer to the origin of disorder, which may be iatrogenic or secondary to other disease.

The term "subject" as used herein includes any member of an animal species, including the human species; by way of an illustrative, non-limiting example, said subject can be a mammal, such as a primate, a domestic animal, a rodent, etc., said subject is preferably a man or woman of any age and race. In a particular embodiment, said subject is a human being with no history of hemostasis disorders, such as an individual having no coagulopathies or platelet disorders. In another particular embodiment, said subject is a human being having a history of hemostasis disorders, such as an individual having hemorrhagic diathesis, for example, a coagulopathy, such as a congenital or acquired coagulopathy, or a platelet disorder, such as a congenital or acquired platelet disorder.

Therefore, in a particular embodiment, the invention relates to the use of TF-bearing yeast derived microvesicles of the invention in the manufacture of a medicament for the topical treatment of hemorrhages in a human being with no history of hemostasis disorders. In another particular embodiment the invention relates to the use of TF-bearing yeast derived microvesicules of the invention in the manufacture of a medicament for the topical treatment of hemorrhaging in a human being having a hemorrhagic diathesis.

As mentioned above, for topical administration to the subject, the TF-bearing yeast derived microvesicules of the invention will be formulated in a pharmaceutical form suitable for its topical administration for topical (local) treatment of hemorrhages in a subject. Illustrative, non-limiting examples of said pharmaceutical forms include aerosols, solutions, suspensions, emulsions, gels, salves, creams, dressings, patches, ointments, mouthwashes, etc. To that end, the pharmaceutical composition comprising TF-bearing yeast derived microvesicules of the invention will include the pharmaceutically acceptable vehicles, carriers and excipients required for preparing the chosen pharmaceutical administration form. Information concerning the pharmaceutical composition (pharmaceutical administration form, doses, amount of active component, etc.) has been already mentioned in connection with the pharmaceutical composition of the invention.

TF has also been reported to induce angiogenesis and increase production of VEGF (Ollivier et al., 2000, Arterioscler. Thromb. Vase. Biol., 20:1374-1381; Chen et al., 2000, Thromb. Haemost., 86:334-345 y Watanabe et al., 1999, Thromb. Res., 96:183-189). Thus, in another aspect, the invention relates to the yeast-derived microvesicles of the invention for the treatment of diseases wherein an increased angiogenesis or an increased cell-migration is required.

Diseases associated with a decreased angiogenesis and which could benefit from the treatment of the angiogenesis-promoting compositions of the invention include coronary artery disease e.g. ischemic myocardium, myocardial infarction, ischemic cardiomyopathy or peripheral arterial disease, such as chronic limb ischemia claudication (skeletal muscle) or rest pain/ischemic ulceration/gangrene. Promoting angiogenesis is required as well in ischemic stroke/neuropathy, such as brain/nerve tissue, for example, ischemic pneumbra around stroke/infarct. Alternatively, the proangiogenic affect of the compositions of the invention may be used to promote healing and/or endothelialization of intravascular luminal surfaces for example, to promote endothelialization of unstable/ulcerated atherosclerotic plaque, for example in coronary/carotid arteries, or on de-endothelialized luminal surfaces such as those found following an endarterectomy, for example within the carotid artery, thrombectomy (either/or arterial/venous), angioplasty, such as balloon, laser, or cryogenic angioplasty, an atherectomy, or following thrombolysis, by administering a composition that includes a nitric oxide agent. The proangiogenic compositions of the invention may also be useful in resolution of acute or chronic arterial and/or venous thrombosis, for example revascularization and/or neovascularization and/or recanalization. In another embodiment, the compositions of the invention promote development of neocapillary beds for gene therapy applications, organ regeneration applications, and for bioartificial hybrid organs (e.g. pancreas, kidney, lung, liver) placement as well as promotion and/or enhancement of wound healing and/or for promoting granulation tissue, for example, for chronic wounds such as ischemic, diabetic, neuropathic, venous statis based wounds.

TF has been reported to promote cell migration (Ott et al., 2005, Circulation, 111:349-355 and WO0105353). Thus, in another aspect, the invention relates to the compositions comprising TF of the invention for the promoting cell migration in patients in need thereof. It will be appreciated that different diseases can be treated with the compositions of the invention depending on the depending on the cell type whose migration is stimulated. For instance, patients which suffer a lesion in a body lumen such as a blood vessel, artery, coronary artery, vein, esophageal lumen, and urethra require a stimulation of the migration of endothelial cells; patients suffering lesions in the central nervous system as a result of both ischemic and hemorrhagic stroke, and from traumatic injury will require an stimulation of the migration of neural cells to the site of the lesion; patients suffering from ulcers which can be chronic and resistant to treatment in, for example, diabetic and elderly patients, e.g. leg ulcers and bed sores, corneal wounds, burns, abrasions, surgical incisions, donor graft sites, and lesions caused by infectious agents). Other medical conditions that can be treated are chronic conditions (such as chronic venous ulcer, diabetic ulcer, compression ulcer, pressure sores, and ulcers or sores of the mucosal surface), skin and epithelial surface lesions caused by a persistent inflammatory condition or infection, or by a genetic defect (such as keloid formation and coagulation abnormalities) will benefit from an stimulation of a migration of epithelial cells needed to repopulate the damaged tissue.

Composition Comprising TF-Bearing Yeast Derived Microvesicles of the Invention

In other aspect, the invention relates to a composition, hereinafter referred to as the "composition of the invention", comprising TF-bearing yeast derived microvesicles of the invention and a vehicle.

Practically, any vehicle which does not adversely affect the TF-bearing yeast derived microvesicles of the invention can be used in said composition of the invention.

In an embodiment, said vehicle is a substantially liquid medium, such as the medium surrounding the TF-bearing yeast derived microvesicles of the invention obtained by working the process of the invention. Therefore, in a particular embodiment, the composition of the invention comprises the clarified yeast extract obtained in the working of the process of the invention.

Truncated TF Lacking all or Part of the Domain Responsible for Binding to FVIIa

As mentioned above, inventors have surprisingly found that a truncated TF protein, being unable to bind to FVIIa, has pro-coagulant activity. As it can be seen in Example 4, inventors have shown that said truncated form of the TF protein has pro-coagulant activity in a coagulation assay in plasma.

Thus, in another aspect, the present invention refers to a truncated TF lacking all or part of the domain responsible for binding to FVIIa, hereinafter referred to as "truncated TF lacking FVIIa binding domain of the invention", wherein all or part of the domain responsible for binding to FVIIa is missing, and, consequently, it is unable to bind to FVIIa, but has pro-coagulant activity. By extension, said "truncated TF lacking FVIIa binding domain of the invention" includes TF protein mutants having pro-coagulant activity in which the domain responsible for binding to FVIIa is not functional due to mutations.

The truncated TF lacking FVIIa binding domain of the invention may be obtained by conventional means, e.g., by means of gene expression of the nucleotide sequence encoding for said protein in a suitable expression system (yeast, bacteria, eukaryotic cells, insect cells, etc.).

In order to determine whether the truncated TF lacking FVIIa binding domain of the invention is capable of binding to FVIIa, binding assays as the one described in the international publication WO00/04148 can be used. In addition, the pro-coagulant activity of the truncated TF lacking FVIIa binding domain of the invention can be assayed as previously mentioned, e.g., by any of the coagulation assays mentioned in Example 4, such as by an in vitro coagulation assay in plasma, or by an in vitro coagulation assay in non-anticoagulated whole blood, or by an in vivo assay in a severe hemorrhage animal model or by an in vivo assay in a lethal hemorrhage animal model, such as those assays mentioned in Example 4.

In a particular embodiment, said truncated TF lacking FVIIa binding domain of the invention comprises the interaction domain to Factor X, the transmembrane region and the cytoplasmic tail and lacks, partially or totally, the domain responsible for binding to FVIIa. Further, in a specific embodiment, said truncated TF lacking FVIIa binding domain of the invention is a truncated form of the human TF protein containing the interaction domain to Factor X (aa 174-251), the transmembrane region (aa 252-274), and the cytoplasmic tail (aa 275-295) and an extra histidine tag (Example 3). Inventors have now surprisingly discovered that said truncated form of TF protein, lacking the domain responsible for binding to FVIIa, has pro-coagulant activity (Example 4, Table 3).

In another particular embodiment, the TF is modified by one or more point mutations in the FVIIa-binding domain so that said domain is no longer capable of binding FVIIa. Point mutations in the FVIIa binding domain of TF which are known to abolish binding to said FVIIa are known in the art (e.g. those described by Kelley, R. F. et al., 1995, Biochemistry, 34:10383-10392 whose contents are therefore incorporated by reference in its entirety).

It has been surprising to observe that said fragment of TF, lacking all or part of the domain responsible for binding to FVIIa, has pro-coagulant activity since, as it is well-known, in the blood coagulation extrinsic pathway, TF binds to circulating FVII/FVIIa to form the TF::FVIIa complex and, in the presence of calcium, to act as a substrate so that FX activation takes place. It is accepted that in the event of a hemorrhage produced by a vascular lesion, coagulation is triggered due to extrinsic pathway activation involving the interaction of TF with its ligand, FVII/FVIIa.

The truncated TF lacking FVIIa binding domain of the invention may be glycosylated or not. Thus, in a particular embodiment, the truncated TF lacking FVIIa binding domain of the invention is not glycosylated, whereas in another particular embodiment, said truncated TF lacking FVIIa binding domain of the invention is glycosylated. As mentioned above, the term "glycosylated" includes any degree of glycosylation.

TF Mutants Carrying One or More Non-Functional Glycosylation Sites

As mentioned above, the authors of the present invention have also observed that the procoagulant activity of TF as well as its expression in yeast host cells is increased when said TF carries mutations in the glycosylation sites that prevent the attachment of at least one of the three N-linked glycosyl chains found in the wild-type TF. Thus, in a particular embodiment, the TF-bearing yeast derived microvesicule of the invention comprises a non-glycosylated fragment of TF protein having pro-coagulant activity. As mentioned above, the term "glycosylated" includes any degree of glycosylation. In a preferred embodiment, the TF variant is a polypeptide wherein at least one of the N-glycosylation sites of TF has been modified so as to render it non-functional, i.e. uncapable of serving as acceptor site for the addition of glycoside chains. The N-glycosylation sites in the TF sequence which can modified are those previously mentioned, i.e. the $Asn^{11}$-$Leu^{12}$-$Thr^{13}$ site, the $Asn^{124}$-$Val^{125}$-$Thr^{126}$ site and/or the $Asn^{137}$-$Asn^{138}$-$Thr^{139}$ site. Any modification of the N-glycosylation consensus regions is suitable as long as the addition of the N-linked glycosyl chain is abolished or substantially inhibited. Preferably, the modification is introduced in the Asn residue corresponding to positions 11, 124 and/or 137 in the mature human TF, since this is the residue that serves as acceptor for the attachment of the glycosyl chain. As used in the present invention "sites corresponding to sites 11, 124 and/or 137 in the mature human TF" relates to the N-glycoylsation sites in other TF orthologs which might appear at a different position in the polypeptide chain but which match with the N-glycosylation sites in the mature human TF when the human and the ortholog sequences are aligned based on sequence similarity. A suitable algorithm for alignment or multiple TF sequences and, thus, for identifying N-glycosylation sites in TF orthologs corresponding to the sites in human mature TF is the PILEUP program which forms part of the GCG Software Package (Genetics Computer Group, Program Manual for the GCG Package, Version 7, Madison, Wis.). PILEUP creates a multiple sequence alignment from a group of related sequences using progressive, pair wise alignments to show relationship and percent sequence identity. It also plots a tree or dendrogram showing the clustering relationships used to create the alignment. PILEUP uses a simplification of the progressive alignment method of Feng and Doolittle, J. Mol. Evol., 35: 351-360 (1987). Preferably, the Asn residues at positions 11, 124 and/or 137 are substituted by Ala. Thus, in a preferred embodiment, the TF variant which forms part of the microvesicles is selected from the group of N11A, N124A, N137A, N11A and N124A, N11A and N137A, N124A and N137A and N11A, N124A and N137A in the human mature TF. In any other TF ortholog, the mutations will take place in the corresponding Asn residues that form the N-linked glycosylation consensus sites.

The truncated TF lacking FVIIa binding domain, the mutant TF carrying a non-functional FVIIa-binding domain and the TF mutants carrying one or more non-functional N-glycosylation sites of the invention may be a member of a fusion protein, said fusion protein containing a first region comprising said truncated TF lacking FVIIa binding domain, said mutant TF carrying a non-functional FVIIa-binding domain and said TF mutants carrying one or more non-functional N-glycosylation sites of the invention bound to a second region comprising another peptide or protein. Said second region may be bound to the amino-terminus region of said truncated TF lacking FVIIa binding domain, said mutant TF carrying a non-functional FVIIa-binding domain and said TF mutants carrying one or more non-functional N-glycosylation sites of the invention, or, alternatively said second region may be bound to the carboxyl-terminus region of said truncated TF lacking FVIIa binding domain, said mutant TF carrying a non-functional FVIIa-binding domain and said TF mutants carrying one or more non-functional N-glycosylation site of the invention. Both first and second regions may be directly bound or bound through a linker polypeptide between said first and second regions.

In a particular embodiment, said fusion protein comprises a truncated TF lacking FVIIa binding domain, a mutant TF carrying a non-functional FVIIa-binding domain or a TF mutant carrying one or more non-functional N-glycosylation site and a tag, usually a peptide tag, bound to the C-terminal or N-terminal domain of said truncated TF lacking FVIIa binding domain of the invention. Said tag is generally a peptide or amino acid sequence which can be used in the isolation or purification of said fusion protein. Illustrative, non-limitative, examples of said tags have been previously mentioned. In a particular embodiment, said tag is a His-tag bound to the C-terminal domain of said TF protein. In another embodiment, said tag is a His-tag bound to the N-terminal domain of said TF protein.

Said fusion protein may be obtained by conventional means, e.g., by means of gene expression of the nucleotide sequence encoding for said fusion protein in a suitable yeast cell. The eventual tag can be used, if desired, for the isolation or purification of said fusion protein.

The truncated TF lacking FVIIa binding domain, the mutant TF carrying a non-functional FVIIa-binding domain and the TF mutants carrying one or more non-functional N-glycosylation site can be used as a medicament, for example, as a pro-coagulant agent in the treatment of haemorrhages in a subject.

Therefore, in another aspect, the invention relates to said truncated TF lacking FVIIa binding domain, said mutant TF carrying a non-functional FVIIa-binding domain and said TF mutants carrying one or more non-functional N-glycosylation site as a medicament. In a particular embodiment, the invention relates to said truncated TF lacking FVIIa binding domain, said mutant TF carrying a non-functional FVIIa-binding domain and said TF mutants carrying one or more non-functional N-glycosylation site as a medicament with pro-coagulant activity suitable for treating haemorrhages in a subject.

Further, in another aspect, the invention relates to a pharmaceutical composition comprising a truncated TF lacking the FVIIa binding domain, a mutant TF carrying a non-functional FVIIa-binding domain or a TF mutant carrying one or more non-functional N-glycosylation site and a pharmaceutically acceptable vehicle. In a particular embodiment, said pharmaceutical composition is a pharmaceutical composition for the topical administration of a truncated TF lacking FVIIa binding domain, a mutant TF carrying a non-functional FVIIa-binding domain or a TF mutant carrying one or more non-functional N-glycosylation site and a pharmaceutically acceptable carrier suitable for the topical administration of said truncated TF lacking FVIIa binding domain of the invention or the mutant TF carrying one or more non-functional N-glycosylation sites.

In another aspect, the invention relates to a truncated TF lacking FVIIa binding domain, a mutant TF carrying a non-functional FVIIa-binding domain and a TF mutants carrying one or more non-functional N-glycosylation site for the treatment of a disease which requires promoting cellular migration and/or angiogenesis in a subject. In another aspect, the invention relates to a truncated TF lacking FVIIa binding domain, a mutant TF carrying a non-functional FVIIa-binding domain or a TF mutant carrying one or more non-functional N-glycosylation site for the promoting angiogenesis or for promoting cellular migration in a subject in need thereof.

In general, for administration to a subject, the truncated TF lacking FVIIa binding domain, the mutant TF carrying a non-functional FVIIa-binding domain or the TF mutants carrying one or more non-functional N-glycosylation site will be formulated in a pharmaceutical form suitable for its topical administration for topical (local) treatment of hemorrhaging. Illustrative, non-limiting examples of said pharmaceutical forms include aerosols, solutions, suspensions, emulsions, gels, salves, creams, dressings, patches, ointments, mouthwashes, etc. To that end, the pharmaceutical composition comprising the truncated TF lacking FVIIa binding domain of the invention will include the pharmaceutically acceptable carriers and excipients required for preparing the chosen pharmaceutical administration form. Therefore, in a particular embodiment, this pharmaceutical composition of the invention comprises, in addition to the truncated TF protein of the invention, a pharmaceutically acceptable vehicle as can be found in galenic pharmacy treatises.

The truncated TF lacking the FVIIa binding domain of the invention, the mutant TF carrying a non-functional FVIIa-binding domain of the invention and said TF mutants carrying one or more non-functional N-glycosylation site of the invention will be present in this pharmaceutical composition in a therapeutically effective amount. Said amount may vary within a wide range, for example, between about 1.0 pg of active protein/ml and 1.0 mg of active protein/ml, preferably between 0.05 µg of active protein/ml and 10 µg of active protein/ml, and even more preferably between about 0.1 µg of active protein/ml and 2.0 µg of active protein/ml.

In another aspect, the invention relates to a polynucleotide sequence (hereinafter referred to as "the polynucleotide of the invention") which codes for said truncated TF lacking FVIIa binding domain, said mutant TF carrying a non-functional FVIIa-binding domain and said TF mutants carrying one or more non-functional N-glycosylation site.

In another aspect, the invention relates to a vector (hereinafter referred to as "the vector of the invention") which comprises a polynucleotide sequence of the invention. Suitable vectors for use in the present invention include prokaryotic expression vectors such as pUC18, pUC19, Bluescript and their derivatives mp18, mp19, pBR322, pMB9, ColE1, pCR1, RP4, phages and shuttle vector such as pSA3 and pAT28, yeast expression vectors such as 2 micro plasmids, integrative plasmids, YEP vectors, centromeric plasmids and the like, plant expression vectors such as pIBI, pEarleyGate, pAVA, pCAMBIA, pGSA, pGWB, pMDC, pMY, pORE vectors and the like, insect cell expression vectors such as pAC and pVL vectors, eukaryotic expression vectors either based in viral vectors (adenovirus, adeno-associated viruses, retroviruses and lentivirus) as well as non viral vectors such as pcDNA3, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1.

In another aspect, the invention relates to a host cell (hereinafter referred to as "the host cell of the invention") which comprises a polynucleotide of the invention or the vector of the invention. Cells that can be used for the purposes of the invention are preferably eukaryotic cells, more preferably a vertebrate or invertebrate cell, insect cells or fungal cells, even more preferably the vertebrate cell is a *Xenopus* cell, a cell isolated from a zebra fish or a mammalian cell. Preferably, the mammalian cell is a cell from a established cell line such as CHO, VERO, BHK, HeLa, COS, MDCK 293, 3T3, WI38 and the like, an embryonic stem cell, an adult stem cell or a somatic cell.

In another aspect, the invention relates to an antibody which binds specifically to a truncated TF lacking FVIIa binding domain, to a mutant TF carrying a non-functional FVIIa-binding domain or to TF mutants carrying one or more non-functional N-glycosylation site of the invention. Suitable antibodies for use in the present invention include "intact" antibodies which comprise an antigen-binding variable region as well as a light chain constant domain (CL) and heavy chain constant domains, CH1, CH2 and CH3, "Fab" fragments resulting from the papain digestion of an intact antibody and which comprise a single antigen-binding site and a CL and a CH1 region, "F(ab')2" fragments resulting from pepsin digestion of an intact antibody and which contain two antigen-binding sites, "Fab" fragments contain the constant domain of the light chain and the first constant domain (CH1) of the heavy chain and has one antigen-binding site only. Fab' fragments differ from Fab fragments by the addition of a few residues at the carboxy terminus of the heavy chain CH 1 domain including one or more cysteines from the antibody hinge region, "Fv" is the minimum antibody fragment which contains a complete antigen-recognition and antigen-binding site, single-chain FV or "scFv" antibody fragments which comprise the VL and VH domains of antibody, wherein these domains are present in a single polypeptide chain, diabodies" comprise a heavy chain variable domain (VH) connected to a light chain variable domain (VL) on the same polypeptide chain (VH-VL) connected by a peptide linker that is too short to allow pairing between the two domains on the same chain and "bispecific antibodies" (BAbs) are single, divalent antibodies (or immunotherapeutically effective fragments thereof) which have two differently specific antigen binding sites.

The following examples illustrate the invention and should not be considered as a limitation thereof.

EXAMPLES

Examples 1-3 disclose the production in yeasts of a pro-coagulant product based on the expression of (i) mature human TF protein, optionally in the form of a fusion protein fused to a His-tag (Example 3), of (ii) a truncated form of human TF protein fused to a His-tag (Example 4) and of (iii) N-glycosylation mutants of human TF protein (example 5). Said pro-coagulant products, all together, are generically named in Example 6, for simplicity, microvesiculated tissue factor, microvesiculated TF or mTF. Example 2 teaches the purification of the microvesiculated TF.

Example 6 discloses some in vitro assays performed for the purpose of evaluating the capacity of said mTF to cause fibrin clot in healthy and hemophilic subjects at different concentrations as well as some in vivo assays performed for the purpose of evaluating the capacity of said mTF to treat haemorrhages in severe and lethal haemorrhage models.

Example 1

Production of a Pro-Coagulant Product Based on the Expression of the Full-Length TF Protein in Yeast (CYE-TF)

1.1. Yeast Expression Vector

For recombinant TF expression, a yeast episomal vector (pTT-10301) was generated from plasmids pG1 (ATCC #37305) and Yep352 (ATCC #37673) following the cloning strategy depicted in FIG. 1. Plasmid pTT-10301 contains the following elements:
  i) the URA3 gene that allows selection of recombinant yeast in the absence of uracil in the growing media,
  ii) the ampicillin resistance gene (Amp) for selection and propagation of the plasmid vector in E. coli,
  iii) the yeast 2 microns (2μ) replication origin, that allows the episomal replication of the vector in yeast,
  iv) the glyceraldehyde-3-phosphate dehydrogenase (GPD) promoter, that controls the transcription of genes placed downstream,
  v) the specific yeast transcription termination signal of the phosphoglycerate kinase (PGK), and
  vi) a unique BamHI restriction site that allows cloning of selected genes under the control of the GPD promoter (pGPD), and followed by the PGK stop sequence (PGKt).

FIG. 1A shows the map of the plasmid vector pTT10301. Restriction endonuclease analysis to confirm the right organization of all elements within the plasmid is shown in FIG. 1B.

E. coli strain DH5α (Stratagene) was used for plasmid amplification. Bacteria cells harbouring plasmid pT710301 were grown at 37° C. in Luria Broth Ampicilin (LBA) medium (1% tryptone, 1% NaCl, 0.5% yeast extract, 50 mg of ampicillin per ml). Glycerol stocks of recombinant bacterial cultures containing pTT-10301 plasmid were kept at −80° C.

1.2. Recombinant Gene

Figure 2:
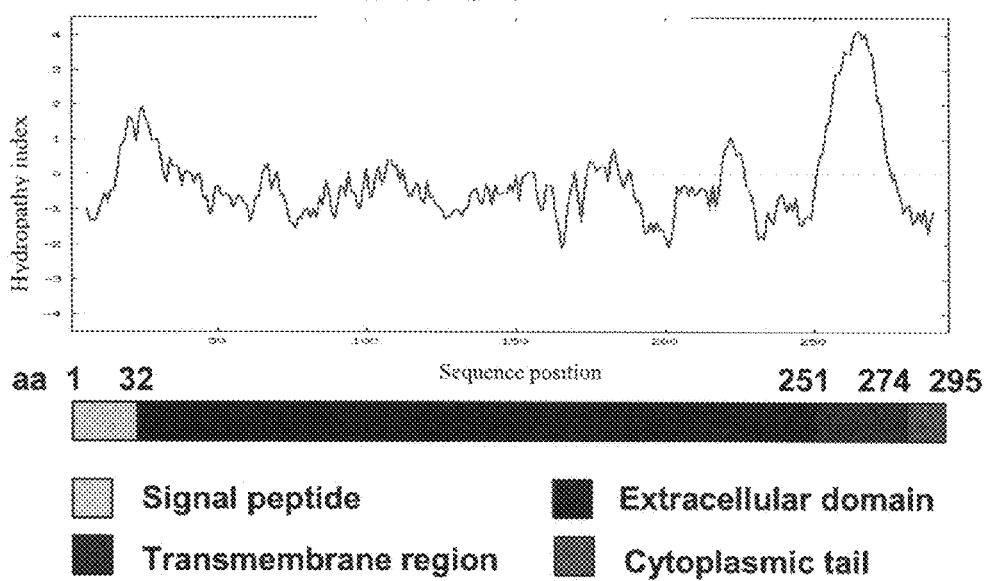
FIG. 2 shows a hydropathy plot of human TF protein. The four domains of the protein (leader sequence, extracellular, transmembrane and cytoplasmic domains) are represented.

Tissue factor (TF) is a 295-amino acid (aa) protein with a 32-aa leader sequence. The mature protein can be divided into three domains: an extracellular domain (aa 33-251), a transmembrane region (aa 252-274), and a cytoplasmic tail (aa 275-295). FIG. 2 shows the hydropathy plot of the human TF (hTF) protein.

The cDNA coding for the mature hTF protein (aa 33-295) was amplified as a 816-bp fragment by polymerase chain reaction (PCR). For this PCR reaction a human placenta cDNA library (Marathon-Ready cDNA, Clontech Laboratories, Inc.) was used as template, and oligonucleotides A and B, annealing respectively at 5' or 3' end of human TF gene, were used as primers.

FIG. 3 shows the annealing sequence of primers A and B within the hTF DNA sequence [SEQ ID NO: 5] (gene bank accession # BC011029). Primer A encodes the first four amino-acids of mature hTF lacking the signal peptide and containing an initiation codon ATG in frame with hTF ORF.

PCR conditions were as follows: 35 cycles of PCR (94° C., 30 s; 45° C. 30 s; 72° C. 1 minute) and a final extension step of 7 minutes at 72° C. Afterwards, the PCR product was purified (Qiagen DNA purification system).

1.3. Generation of rTF Plasmid Expression Vector

Figure 4:
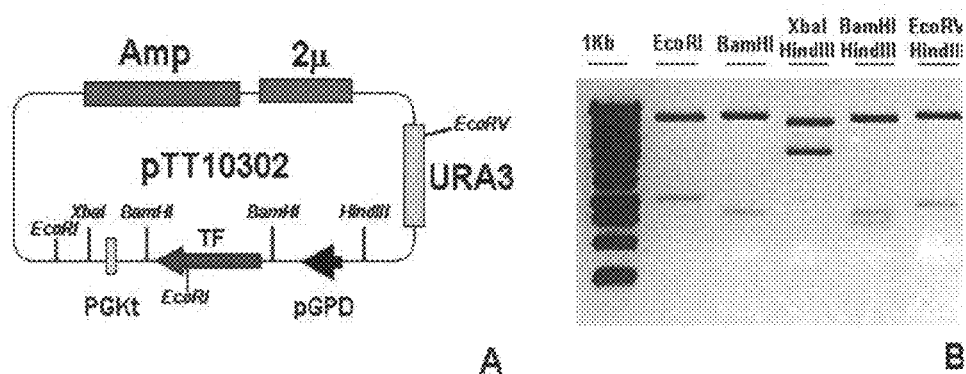
FIG. 4 shows a schematic representation of the cloning strategy for generating pTT10302 plasmid (FIG. 4A). The DNA fragment obtained from the PCR reaction was digested with BamHI and cloned into the pTT10301 plasmid, previously digested with BamHI and dephosphorylated. The resulting plasmid (pTT10302) was grown in $E.$ $coli$ and purified with the commercial DNA purification JETstar kit (Genomed Gmbh).

The PCR-amplified DNA fragment obtained as mentioned in Section 1.2 was digested with BamHI to remove the ends, ethanol precipitated, and cloned into the pTT10301 vector previously digested with BamHI. After endonuclease restriction analysis of several clones, a plasmid containing the recombinant mature hTF (hereinafter referred to as rTF) gene in the correct orientation with respect to the GDP promoter (pGDP), named pTT10302, was selected (FIG. 4).

The DNA sequence of the rTF contained in plasmid pTT10302 was 100% identical to the published sequence (Gene Bank #BC011029). The DNA sequence of the rTF coding DNA was performed in an automatic sequencer (ABI prism 370, Applied Biosystems) using primers A and B and Big Dye Terminator reagents. DH5α E. coli cells carrying the pTT10302 plasmid were grown overnight at 37° C. in LBA medium and used to prepare glycerol stocks, that were kept at −80° C.

1.4. Expression of rTF by Recombinant Yeast

To generate recombinant yeast expressing recombinant mature human tissue factor (rTF), the expression vector pTT10302 was used to transform T73 ura3⁻ yeast cells.

T73 ura3⁻ is a derivative of the very well characterized S. cerevisiae T73 strain, that is widely used in wine production. T73 is a diploid strain selected in the region of Alicante, Spain (Colección Española de Cultivos Tipo, access number # CECT1894), and it is worldwide commercialized for food industry by Lallemand Inc. (Montreal, Quebec, Canada). Strain T73 ura3⁻ is a T73 derivative in which both copies of the URA3 gene have been disrupted (J. Agric. Food Chem. 1998. 46, 1689-1693). T73 ura3⁻ is a stable phenotypically URA- and food-safe yeast strain that allows the generation of T73 recombinant yeast using plasmid vectors carrying the URA3 selectable marker gene.

To generate working stocks, T73 ura3⁻ cells were grown in a Petri dish and a single colony was isolated and grown at 30° C. in YPD medium (1% yeast extract, 2% bacteriological peptone, 2% glucose) until reaching a density of $10^7$ cells/ml. Then, yeast cells were pelleted by centrifugation, resuspended in 15% glycerol in minimal selective medium (yeast extract nitrogen base and complete synthetic medium without uracil; YNB CSM-URA) and frozen in aliquots at −80° C. until their use. Three randomly chosen aliquots were thawed and checked for the absence of bacterial contamination. First, a fresh T73 ura3⁻ aliquot was thawed and cells were made susceptible to acquire the plasmid vector according to the LiAc/SS-DNA/PEG protocol (Methods in Enzymology 1994. 350:87-96). A similar strategy was followed to generate control recombinant yeast harboring the empty plasmid pTT 10301.

Recombinant yeast clones were selected by their ability of growing in media lacking uracil. Eight independent clones transformed with pTT10302 were isolated and cultured overnight in medium without uracil. These recombinant yeast cultures, named as yTT10301, were pelleted and homogenized using glass beads. Similarly, independent clones from yeast transformed with pTT10301 (named as yTT10300) were also subjected to the same procedure.

Figure 5:
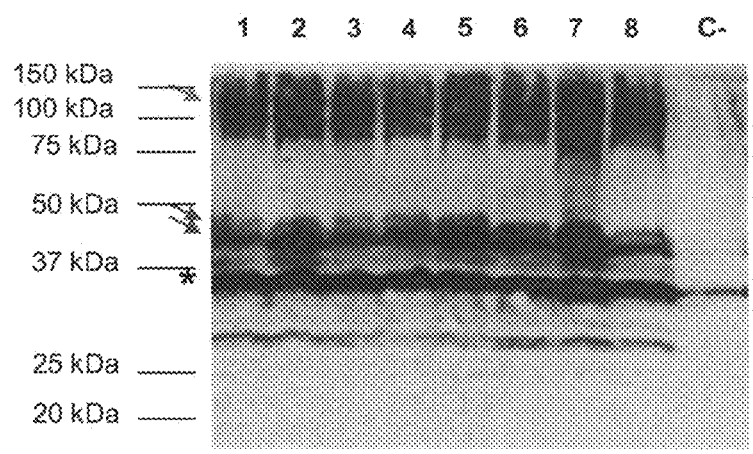
FIG. 5 shows the expression of rTF in different recombinant yeast clones. Western-blot analysis of the extracts from yeast transformed with the empty plasmid pTT10301 (C—) and with the expression vector containing the recombinant mature hTF protein, pTT10302 (lanes 1-8), were carried out by using the purified mouse anti-human CD142 monoclonal antibody (BID Biosciences Pharmingen). Molecular weight markers in kDa are shown at the left side of the Figure.

Proteins from different clones of both types of recombinant yeasts were separated by SDS-PAGE and transferred to a nitrocellulose membrane that was subjected to Western-blot analysis. As shown in FIG. 5, all selected clones from yTT10301 cultures (clones 1 to 8) expressed several polypeptides that were recognized by the anti-human TF specific monoclonal antibody (mAb) CD142 (BD Biosciences Pharmingen). However, none of the yTT10300 clones showed immunoreactive polypeptides with the specific anti-human TF mAb (lane C, in FIG. 5, corresponds to one of these clones).

As shown in FIG. 5, the molecular size of the main immunoreactive product in yTT10301 (lanes 1 to 8) was about 35 kDa (denoted with an asterisk). Other products with molecular masses of 44 and 46 kDa (denoted with arrows), and a large aggregate ranging from 70 to 115 kDa in size (arrow) could also be observed. Polypeptides with molecular weights lower than 35 kDa likely correspond to rTF degradation products.

Figure 6:
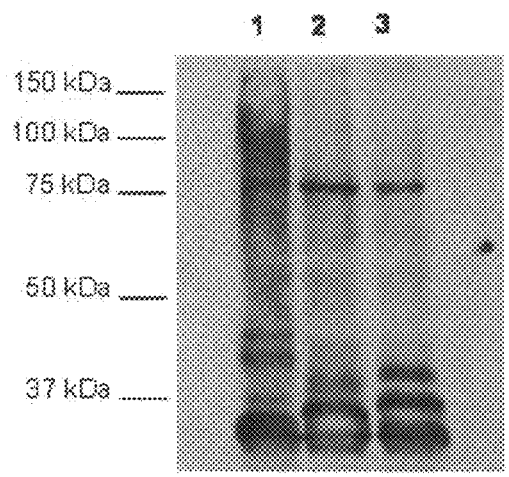
FIG. 6 shows the results of a Western blot after endoglycosylase treatment of yTT10301 extracts. Thus, extracts from rTF-expressing yeast (yTT10301) were treated with 500 units of endoglycosylase H (Endo H)(lane 2) or N-Glycosydase F (PNGase F) (lane 3) for 1 hour at 37° C., following the manufacturer instructions. These samples and the untreated extract (lane 1) were analysed by Western-blot with the anti-human TF mAb. Molecular weight markers in kDa are shown at the left side of the figure.

The appearance of several TF related products showing different electrophoretic mobilities could be due to either protein aggregation, different degrees of glycosylation or both. To investigate these possibilities, extracts from yTT10301 (clone #7) were treated with the endoglycosylases Endo H and PNGase F. As shown in FIG. 6, after incubation with either Endo H (lane 2) or PNGase F (lane 3) the larger aggregate (75 to 150 kDa) disappeared while a 75 kDa product was clearly seen (compare lane 1 with lanes 2 and 3). In addition, the 44 and 46 kDa protein bands also disappeared with both treatments. In samples treated with Endo H (lane 2) the 44 and 46 kDa products seem to give rise to a product of about 36 kDa. PNGase F treatment resulted in the appearance of two bands of 37 and 39 kDa (lane 3). On the other hand, the 35 kDa product remained unchanged after treatment with these glycosylases. Thus, it appears that the 35 kDa product corresponds to unglycosylated rTF protein and the 75 kDa product that can be recognized after endoglycosylase treatment may represent a dimer of the non-glycosylated protein. The large aggregate observed in untreated samples could correspond to the same dimer but with different degrees of glycosylation. Similarly, the 44 and 46 kDa proteins seem to correspond to the 35 kDa protein with different glycosylation patterns.

The predicted molecular weight of hTF lacking the signal peptide determined according to the amino acid sequence is 29.8 kDa. The discrepancy between the predicted and observed molecular mass could be due to anomalous migration of the protein in SDS-PAGE due to the presence of a stretch of hydrophobic amino acids.

Figure 7:
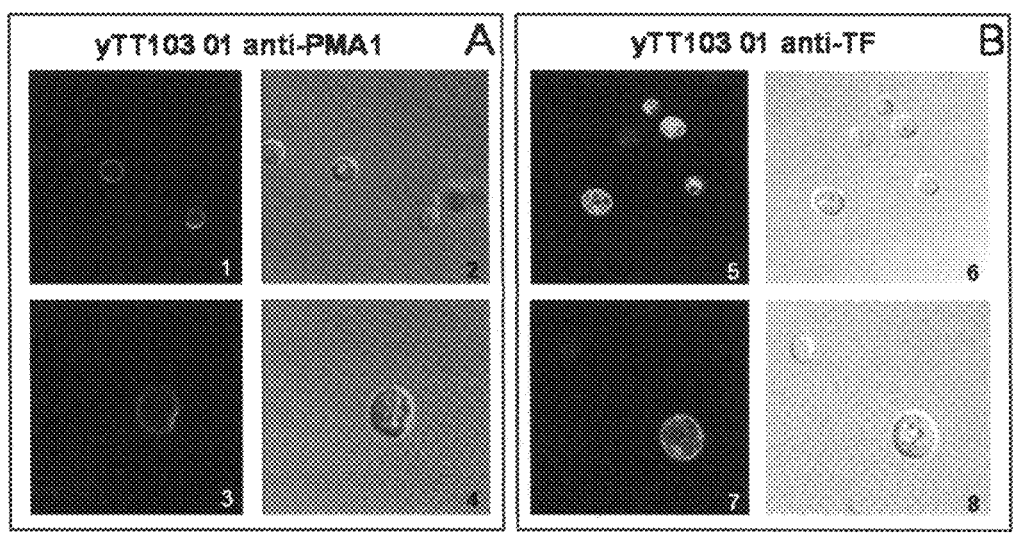
FIG. 7 are confocal laser microscope photographs showing expression of rTF by yTT10301 recombinant yeast. Spheroplasts from recombinant yeast expressing rTF were fixed with 4% paraformaldehyde and incubated with a mAb against a yeast ATPase (FIG. 7A) or with an anti-human TF mAb (FIG. 7B). After incubation with a fluorescein-conjugated secondary goat anti-mouse antibody, cells were observed by confocal microscopy (1, 3, 5 and 7) or by phase contrast (2, 4, 6 and 8). Images were taken in a BIO-RAD Radiance 2000 confocal laser microscope.
Figure 8:
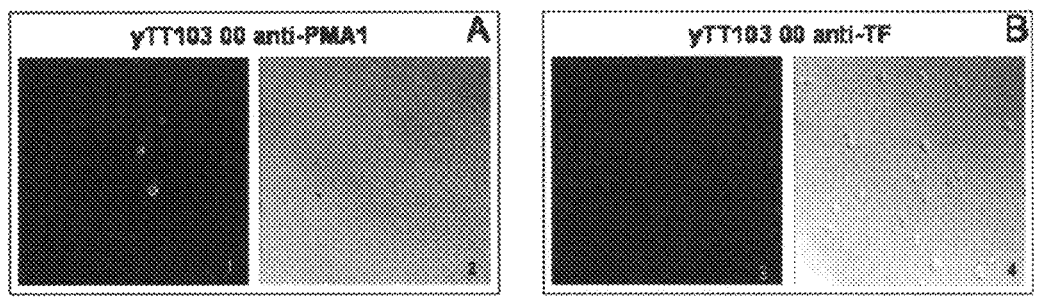
FIG. 8 are confocal laser microscope photographs showing that expression of rTF by recombinant yeast depends on the presence of the pTT10302 plasmid. Spheroplasts from recombinant yeast (yTT10300) harbouring the empty expression plasmid pTT10301 were fixed with 4% paraformaldehyde and incubated with a mAb against a yeast ATPase (FIG. 8A) or with an anti-humanTF mAb (FIG. 8B). After incubation with a fluorescein-conjugated secondary goat anti-mouse antibody, cells were observed by confocal microscopy (1 and 3) or by phase contrast (2 and 4). Images were taken in a BIO-RAD Radiance 2000 confocal laser microscope.

Additionally, expression of rTF by yTT10301 was analyzed by lasser scanning confocal microscopy. For these studies, spheroplasts (i.e., a yeast lacking cell wall produced by enzymatic treatment) from non-expressing (yTT10300), and rTF-expressing (yTT10301, clone #7) recombinant yeasts were fixed and incubated with either the anti-human TF mAb or with a mAb against a yeast membrane ATPase. As shown in FIG. 7, the anti-ATPase mAb specifically labelled only the surface of the spheroplasts (FIG. 7A, pictures 1 and 3). However, the anti-human TF mAb showed a signal distributed all over the cell, indicating the presence of rTF not only on the plasma membrane, but also inside the cell, probably associated with internal membranous cell compartments (FIG. 7B, pictures 5 and 7). On the other hand, as shown in FIG. 8, in yeast cells harbouring an empty plasmid (yTT10300) the anti-ATPase mAb gave also a specific signal on the cell surface (FIG. 8A, picture 1), but, as expected, labelling with the anti-human TF antibody was not detectable (FIG. 8B, picture 3).

Figure 9:
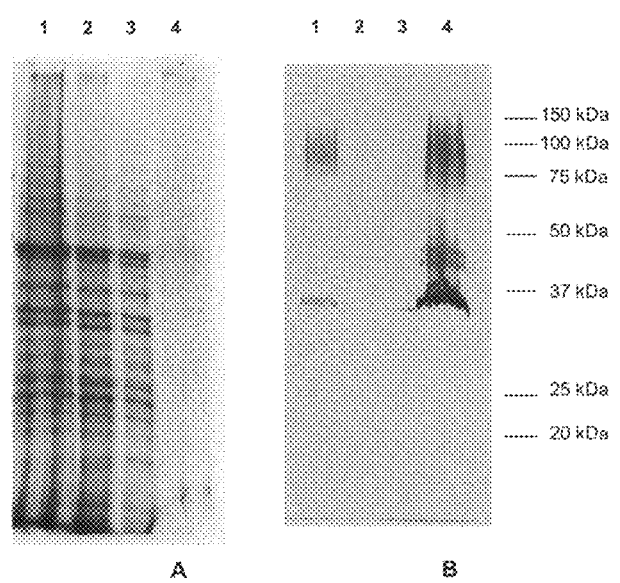
FIG. 9 shows that rTF is associated to yeast membranes. An extract from yTT10301 was treated with Triton X114 and after centrifugation the aqueous phase and the detergent pellet were taken separately. The aqueous phase was treated again with Triton X114 (1% final concentration), and two phases were separated as before. The second detergent pellet was mixed with the first one. The whole extract (lane 1), the first (lane 2), the second (lane 3) aqueous phases, and the detergent phase (lane 4) were analyzed by SDS-PAGE and Coomassie staining (FIG. 9A) or by Western-blot reacted with a mAb against human TF (FIG. 9B).

To confirm that the rTF was a membrane associated protein, yTT10301 yeast cells were treated with lysis buffer containing the detergent Triton X-114 (to a final concentration of 1%). After 1 hour incubation at 4° C. the lysate was applied over 6% sucrose cushion, warmed at 30° C. for 3 min and centrifuged at 300×g for 3 min to separate the upper aqueous phase from the lower detergent phase. The aqueous phase was collected and the detergent pellet was kept on ice. After taking a small aliquot for subsequent analysis, the aqueous phase was subjected to a second round of Triton X-114 extraction. After a new phase separation, a second aqueous phase was collected and the new detergent pellet was added to the previous one. The mixture of both detergent pellets and the two aqueous phases were analyzed by SDS-PAGE and Coomassie-blue staining (FIG. 9A), and by Western-blot with the anti-human TF mAb (FIG. 9B). As shown in FIG. 9B, the characteristic rTF derived products were exclusively observed in the detergent phase (lane 4), and not in any of the two aqueous phases (lanes 2 and 3). In the Coomassie stained gel we can see that most proteins from yeast extracts remained in the aqueous phase (lanes 2 and 3). This result clearly shows that rTF expressed by yTT10301 is membrane associated.

1.5. Fermentation Process

To test the production of yTT10301 yeast extracts at pre-industrial level, inventors performed fermentations in a 2 liter bioreactor (Biostat B-2L. BRAUN). The operating conditions and culture medium were:

Operating conditions: T: 30° C.; Stirring speed: 250-300 rpm; pH: 4.5; Air flow: 6 L/m.

Culture medium: CSM-URA:0.78 g/L; YNB: 6.7 g/L; Sucrose: 20 g/L

Figure 10:
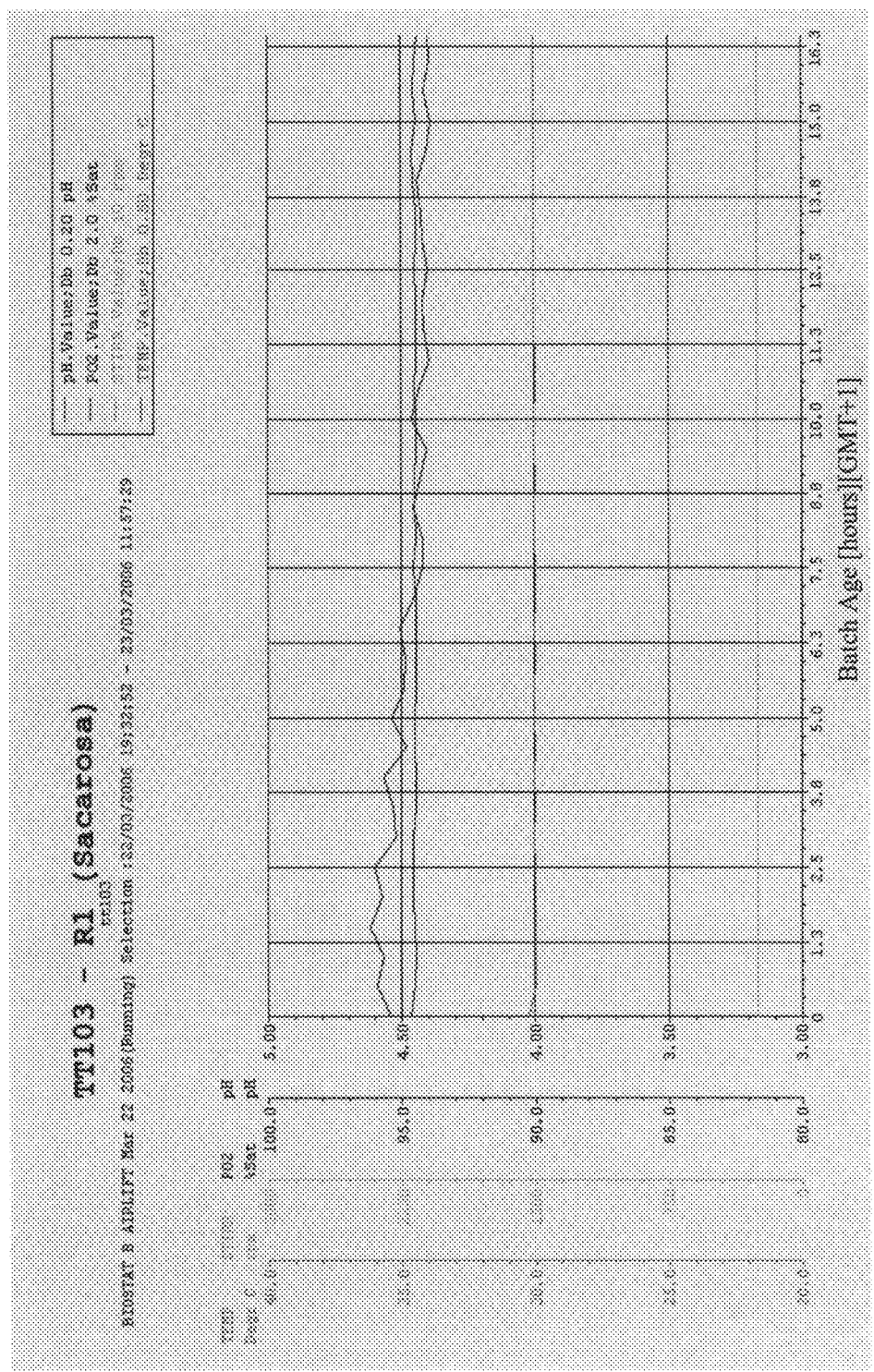
FIG. 10 is a graph showing the evolution of the main parameters throughout the fermentation process. A change in the oxygen pressure ($PO_2$), which is the only uncontrolled parameter, reflects the changes in oxygen requirements undergone by cells during the process. Fermentation was stopped when $PO_2$ reached a stationary state (18 hours).

The graph in FIG. 10 shows the evolution of the main parameters throughout the fermentation process. A change in the oxygen pressure ($PO_2$), which is the only uncontrolled parameter, reflects the changes in oxygen requirements undergone by cells during the process. Fermentation was stopped when $PO_2$ reached a stationary state (denoted with an arrow) (18 h).

The product resulting from the fermentation was pelleted by centrifugation at 3,000 rpm (1,200×g) for 10 min and resuspended in 200 ml of lysis buffer (25 mM PIPES (pH 7.8), 50 mM NaCl). Yeasts were homogenized by high pressure (1,000 bar ($10^8$ Pa)) (homogenizer NIRO SOAVIS. Panda 2K), and the homogenate centrifuged at 13,000 rpm (13,000× g) for 30 min at 4° C., and pellet (50 ml) and the clarified yeast extract (CYE) supernatant (150 ml) were collected separately. The general scheme of the procedure is represented in FIG. 11.

Figure 12:
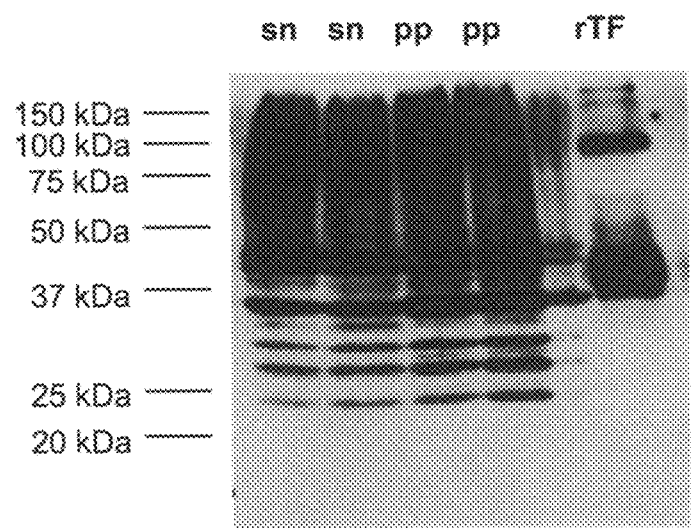
FIG. 12 shows the results of a Western-blot analysis to determine the presence of TF in preparations obtained from the first fermentation test. Each lane corresponds to 5 µl of either supernatant (sn) or pellet (pp) obtained by the procedure described in FIG. 11. Protein samples were analyzed by Western-blot using a specific mAb against human TF. The positive control (rTF) is a commercial recombinant TF (10 ng) produced in E. coli (American Diagnostica, Inc.). Molecular weight markers, in kDa are shown at the left side of the figure.

Protein concentration in both preparations was quantified by the standard colorimetric BCA assay (Pierce), and the presence of rTF was determined by Western-blot analysis. The results of these assays showed that concentration of total protein was similar for both samples (pellet: 3.8 mg/ml and CYE: 3.9 mg/ml), and, accordingly, the amount of rTF detected by Western-blot was also equivalent in the CYE and in pellet as shown in FIG. 12.

The pro-coagulant activity, determined as described in EXAMPLE 4, in the CYE and the pellet was also similar when both samples were analyzed on the same day of preparation (1,400 ng/ml of active rTF), but rTF stability was much lower in pellet extracts (1,500 vs 199 ng/ml) at day $4^{th}$ after preparation probably due to the presence of proteases in this fraction. Thus, the CYE fraction was selected for subsequent drug product preparations.

1.6. Electron Microscopy

Figure 13:
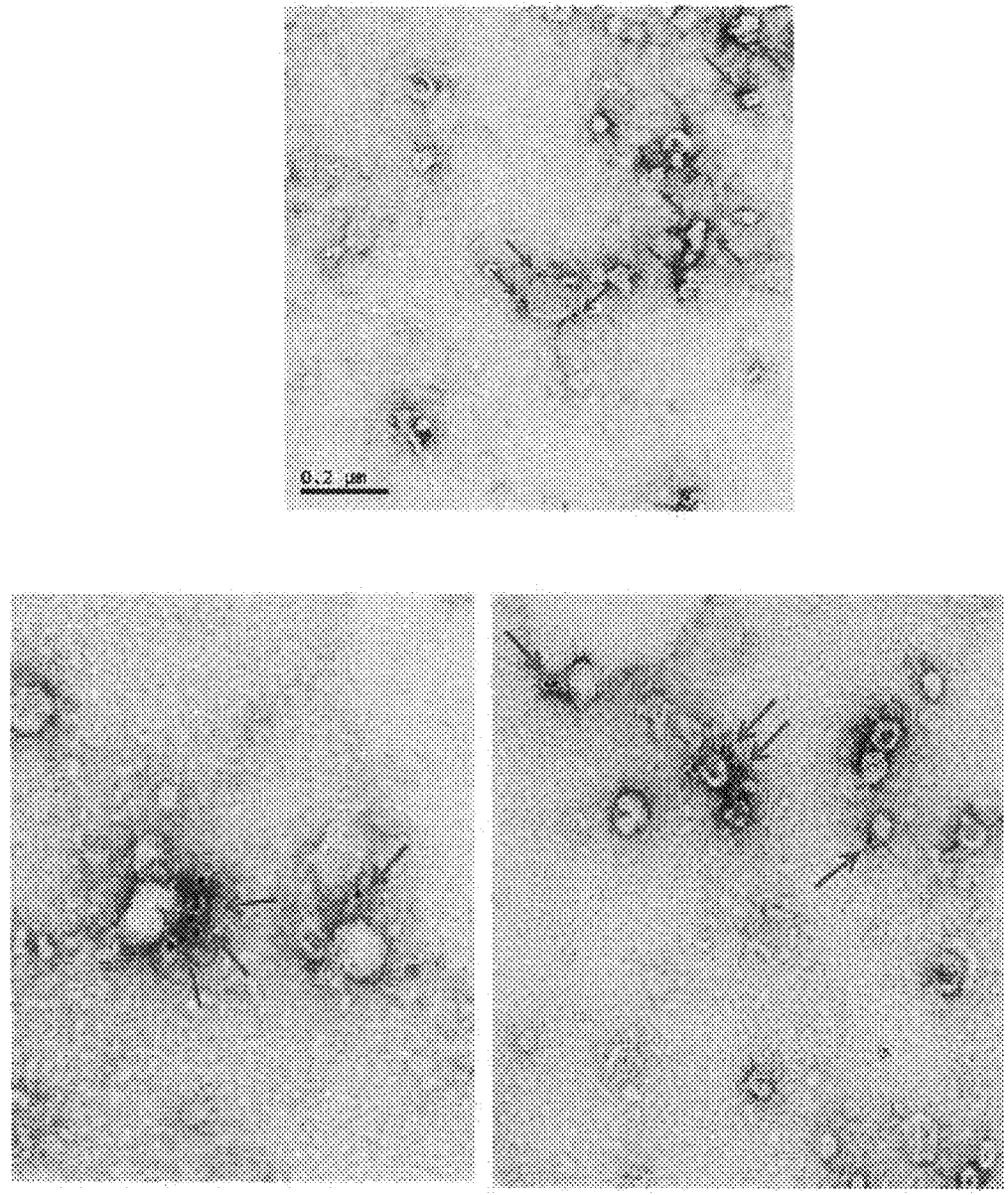
FIG. 13 shows electron microscopy pictures of CYE-TF samples. CYE-TF product was adsorbed to carbon-coated copper grids previously treated by a glow discharge. The grid was incubated with PBS containing 3% bovine serum albumin (BSA) for 1 hour previously to incubation with the specific mAb against hTF or with an unrelated antibody. Grids were extensively washed with PBS and incubated with gold-conjugated rabbit anti-mouse IgG secondary antibody. Grids were washed and samples were negatively stained by treatment with 1% uranyl acetate. The images were obtained in a JEOL 1200 EXII electron microscope. Arrows indicate the position of colloidal gold particles.

To better characterize the CYE product, immunoelectron microscopy analysis was performed. The examination of CYE samples by electron microscopy (EM) showed the presence of a large number of yeast-derived vesicles of different sizes (ranging from 0.1 to 0.01 μm). About 5-10% of these vesicles were labeled by the anti-human TF mAb as observed by the presence of gold particles in their periphery (denoted with arrows) (FIG. 13). On the other hand, in the control grids that were incubated with an unrelated mAb very few gold particles were observed, and they were not associated to vesicles (not shown).

It is well established that optimal blood-clotting activity requires the association of TF to lipids (Thromb. Haemost. 2001; 86: 66-74), and since non-expressing TF yeast extracts from yTT10300 did not exhibit any pro-coagulant activity, these results indicated that the pro-coagulant activity of the CYE would reside on the lipidated rTF resulting from the association of rTF to yeast-derived membranous microvesicles, hereinafter referred to as CYE-TF (i.e. a fraction of CYE, having pro-coagulante activity, containing rTF in association with yeast-derived membranous microvesicles).

Example 2

Production of a Pro-Coagulant Product Enriched in Microvesicles Containing the Full-Length TF (mTF)

2.1 Purification Process

Figure 14:
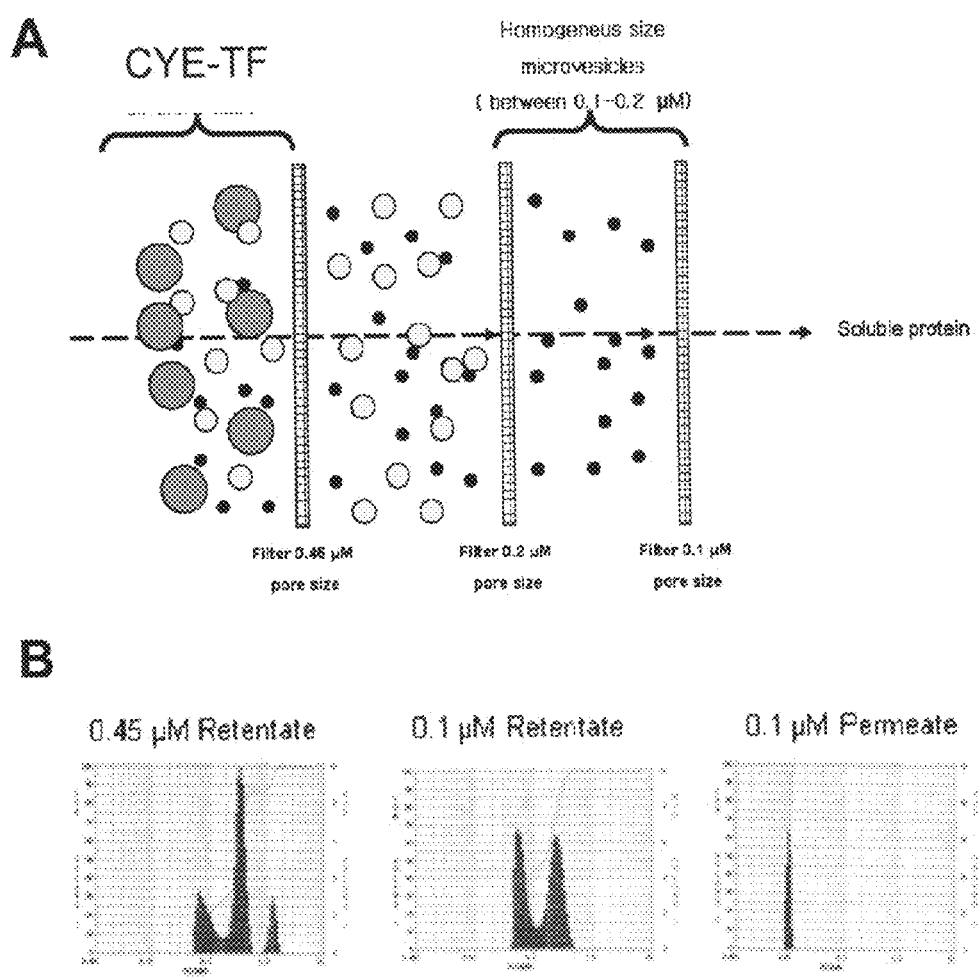
FIG. 14 shows a scheme of the clarification procedure of CYE-TF by Tangential Flow Filration.—A) The CYE-TF was subjected to a tangential flow filtration (TFF) in a Crossflow Filtration System (Sartorius sartoflow Slice 200 Benchtop). CYE-TF was sequentially filtered through 0.45 µm, 0.2 µm and 0.1 µm membranes (Sartorius, polysulfone). The membranes were previously equilibrated with Phosphate Buffer (20 mM sodium phosphate pH 7.4, 500 mM NaCl). The material remaining retained after filtration through the 0.2 µm and before 0.10 µm membranes was recovered and used as starting material for the successive purification steps. B) Dinamic light scattering was used to determine the size distribution of microvesicles.

A clarified yeast extract containing rTF (hereinafter referred to as CYE-TF) obtained from yTT10301 was prepared following the procedure previously described (Example 1, Sections 1.1 to 1.5). The CYE-TF was subjected to successive steps of tangential flow filtration in a Crossflow Filtration System (Sartorius sartoflow Slice 200 Benchtop) using filters with a gradual reduction on the pore size (0.45 µm, 0.2 µm and 0.1 µm membranes (Sartorius, polysulfone). A diagram of the procedure followed is depicted in FIG. 14A.

Figure 15:
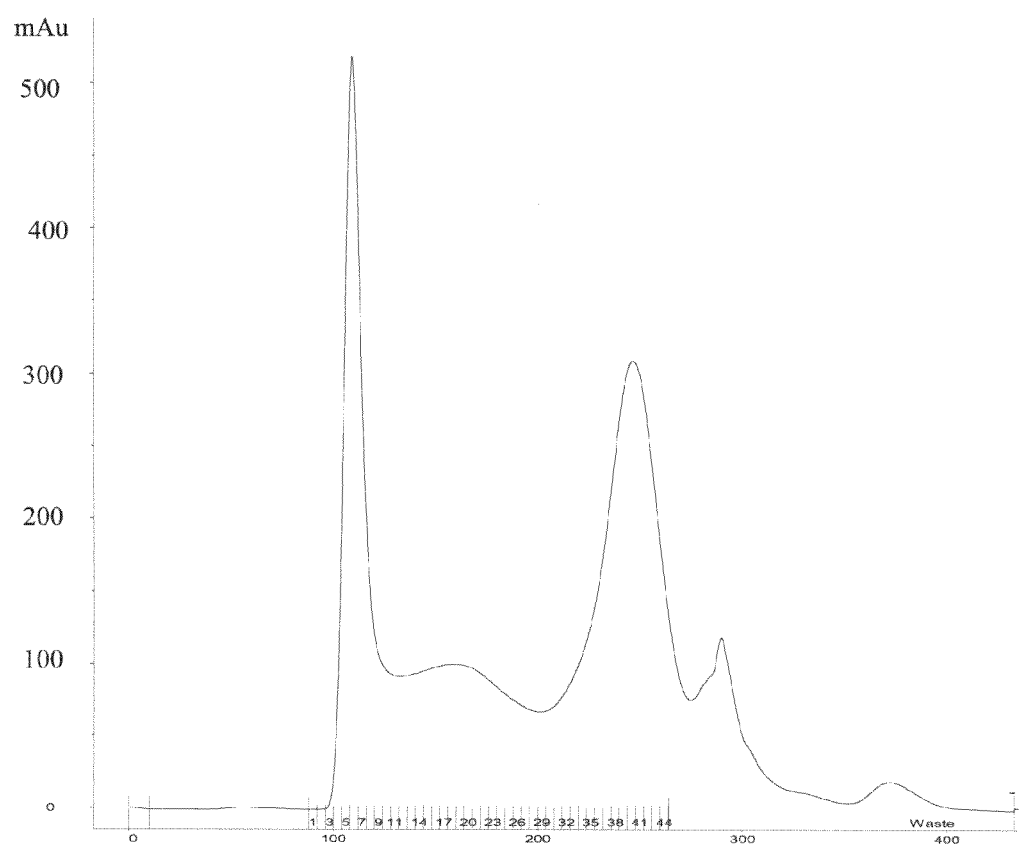
FIG. 15 shows a size-exclusion chromatography profile of the CYE-TF product carried out in a Sephacryl S-500 column. Elution was performed at 4° C. with Phosphate Buffer and 4 mL-fractions were collected at flow rate of 1 mL/min. Protein elution was monitored by measuring the optical density at 280 nm.

To purify the microvesicles containing rTF (mTF) 10 mL of filtered CYE-TF extract, corresponding to microvesicles of 0.1 to 0.2 µM in size (0.1 µM retentate), were loaded on a size-exclusion chromatography column (Sephacryl S500 column—HR (60 cm-26 mm, 320 mL—General Electric) previously equilibrated with Phosphate Buffer and coupled to an AKTA-FPLC system. Elution was performed at a flow rate of 1 mL/min using the same buffer, and 42 fractions of 4 mL each were collected. The elution pattern was monitored by measuring the absorbance of the fractions at 280 nm. The chromatographyc profiles obtained in different purification trials were similar. The graph in FIG. 15 shows a representative chromatographic profile.

Figure 16:
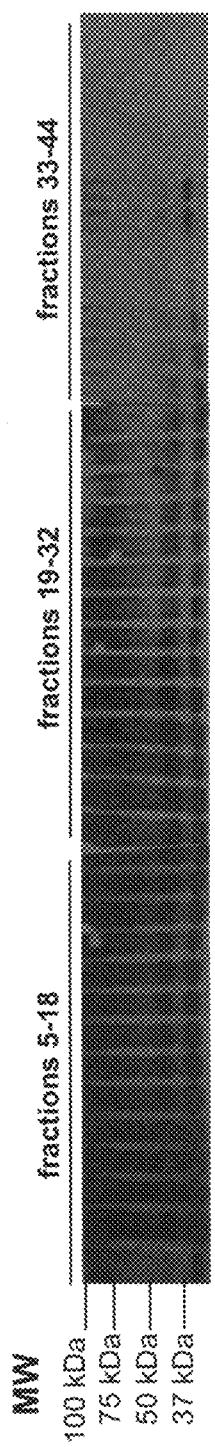
FIG. 16 shows a Western-blot assay to detect rTF. 15 µL of each fraction were electrophoresed on 12.5%-SDS-PAGE Tris-Glycine gel. After electrophoresis proteins were transferred to nitrocellulose membranes. The membranes were then incubated with an antiTF commercial mouse monoclonal antibody (American Diagnostica) for 1 hour. The membranes were then incubated with rabbit anti-mouse IgG antibodies, followed by incubation with horseradish peroxidase-conjugated goat anti-rabbit IgG antibodies. Immunoreactive proteins were detected by chemiluminescence using ECL Advanced Western blotting kits (GE Healthcare).

Aliquots from each fraction were analyzed by westernblot, and by activity assay to identify those fractions containing pro-coagulant activity. FIG. 16 shows that fractions 5-25 that accumulate mTF as observed by western-blot, were also the fractions where activity was concentrated (Table 1).

TABLE 1 mTF pro-coagulant activity in fractions 5-42 obtained after size-exclusion purification

| Fraction | activity ngTF/mL |
|---|---|
| F.5 | 169 |
| F.6 | 236 |
| F.7 | 353 |
| F.8 | 298 |
| F.9 | 261 |
| F.10 | 246 |
| F.11 | 197 |
| F.12 | 237 |
| F.13 | 239 |
| F.14 | 261 |
| F.15 | 241 |

TABLE 1-continued mTF pro-coagulant activity in fractions 5-42 obtained after size-exclusion purification

| Fraction | activity ngTF/mL |
|---|---|
| F.16 | 125 |
| F.17 | 269 |
| F.18 | 312 |
| F.19 | 263 |
| F.20 | 265 |
| F.21 | 282 |
| F.22 | 248 |
| F.23 | 171 |
| F.24 | 146 |
| F.25 | 106 |
| F.23 | 171 |
| F.24 | 146 |
| F.25 | 106 |
| F.26 | 32 |
| F.27 | 3 |
| F.28 | 0 |
| F.29 | 0 |
| F.30 | 0 |
| F.31 | 0 |
| F.32 | 0 |
| F.33 | 0 |
| F.34 | 0 |
| F.35 | 0 |
| F.36 | 0 |
| F.37 | 0 |
| F.38 | 0 |
| F.39 | 0 |
| F.40 | 0 |
| F.41 | 0 |
| F.42 | 0 |
| F.43 | 0 |

Figure 17:
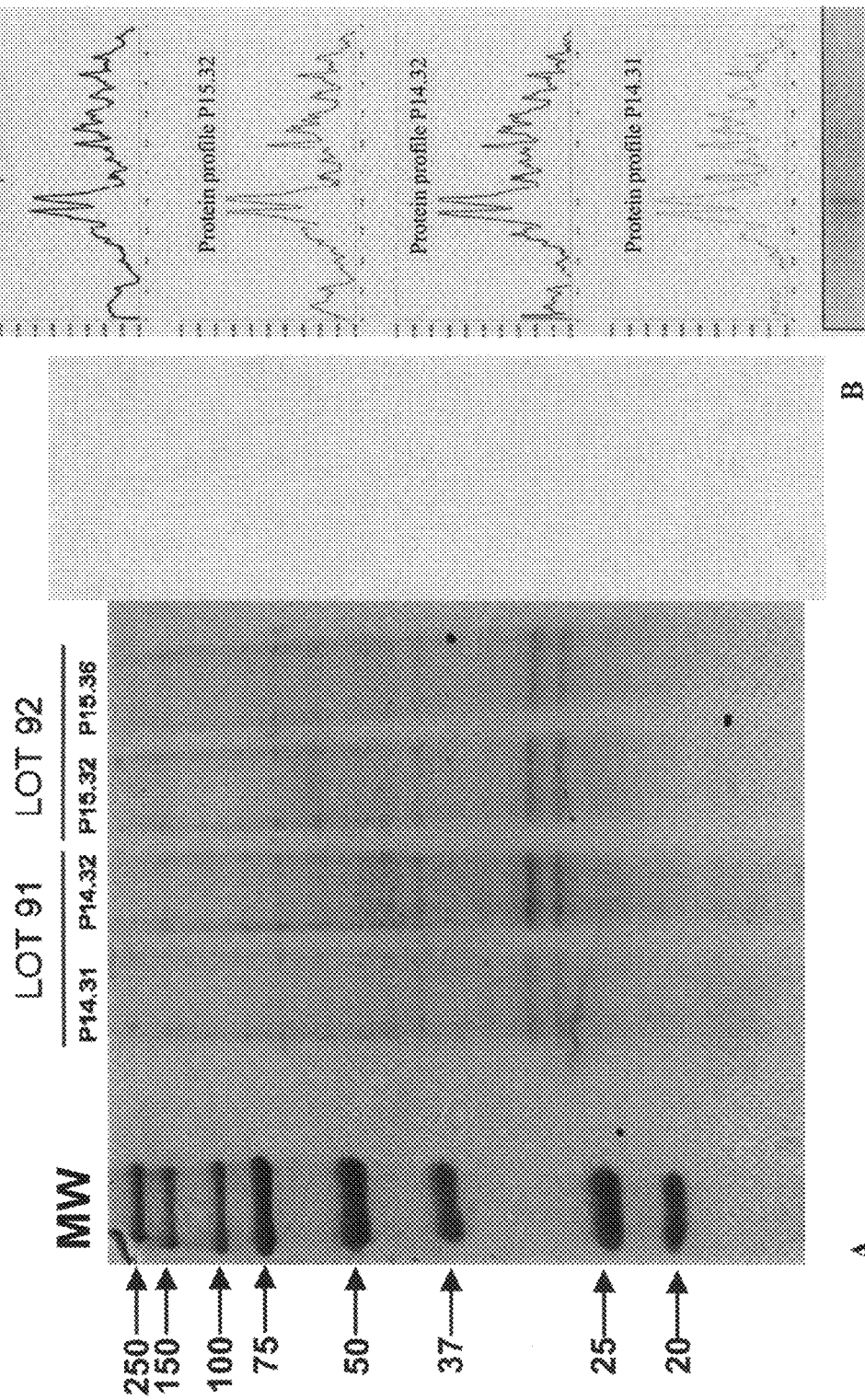
FIG. 17 shows a protein profile of different lots of microvesicles containing rTF purified by size-exclusion chromatography. A) Proteins from four different lots of purified microvesicles containing rTF (as indicated on the top of the figure) were fractionated by SDS-PAGE, and the gel was stained with coomassie blue. Molecuñlra weight markers are shown at the left side of the figure. B) Densitometry analysis of the different protein bands in each lot performed after scanning of the stained gel.

Finally, to concentrate activity, fractions 5 to 43 from each purification process were pooled and subjected again to TFF through a 0.1 µm filter. By these means it is possible to obtain reproducible lots (14.31, 14.32, 15.32, 15.36) of biologically active mTF, as shown in Table 2, and these lots all show a similar protein profile (FIG. 17).

TABLE 2

Comparison of the total protein content and the pro-coagulant activity between lots

| | Total Protein µg/mL | Active Protein ng/mL |
|---|---|---|
| mTF Pool 14.31 | 346 | 709 |
| mTF Pool 14.32 | 283 | 659 |
| mTF Pool 15.32 | 271 | 745 |
| mTF Pool 15.36 | 342 | 718 |

2.2. Biochemical Characterization of rTF-Containing Microvesicles Purified by Size-Exclusion Chromatography 2.2.1. Protein Content The microvesicles where rTF is inserted contain in addition to rTF other integral membrane proteins derived from the yeast host cell. The protein content of different lots of purified mTF was analyzed by SDS-PAGE and Coomassie blue staining (FIG. 17A). Visual comparison of the stained gel indicates that the protein profile of different lots was almost identical. To perform a more accurate comparative analysis, the gel was scanned and each lane of the gel was subjected to densitometry and a plot showing the peaks corresponding to the different protein bands, and the relative intensity of each protein, was obtained from each lot. The protein profiles of the four lots shown in FIG. 17 (panel B) were extremely similar.

2.2.2. Lipid Content

The lipid content of the purified mTF was analyzed by thin layer chromatography following the procedure described by Hara and Radin (Anal. Biochem. 1978, 90: 420-426) with some modifications (Rodriguez-Sureda y Peinado-Onsurbe, 2005, Anal. Biochem. 343: 277-282). Basically, 120 mg of lyophilized product into a glass tube was dissolved into 1 mL of a mixture of hexane and isopropanol (3:2, v:v). The vial, protected for the light to avoid lipid oxidation, was maintained into an orbital shaker for 24 h. At this time, 0.3 mL of sodium sulphate (0.47 M) was added. To facilitate the phase separation, the sample was centrifuged. The upper phase (hexane) contains apolar lipids while the polar ones as phospholipids are found close to the interphase. The upper phase was transferred to a different vial and was evaporated using Nitrogen-gas to avoid lipid oxidation. The dry extract containing lipids was dissolved in chloroform (0.2 mL). The TLC was carried out on a silica gel plate using as a mobile phase Chloroform:Methanol and water (C:M:W, 345:133:21, v:v:v). In parallel to the samples, lipid standards were analyzed under the same conditions. Once the samples were run on the plates, lipids were visualized by addition of iodine vapours. The identification of the different lipid components in the samples was done by comparing their mobility with that of the standards.

Figure 18:
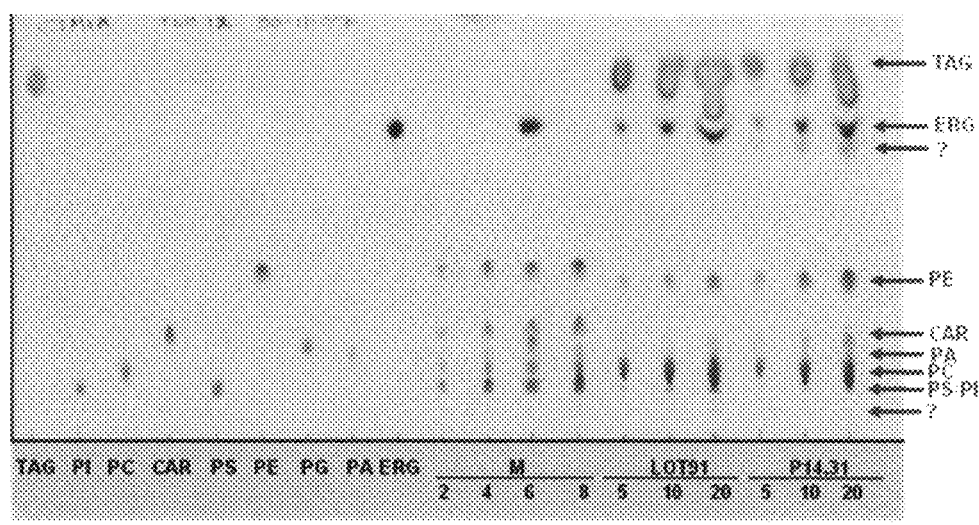
FIG. 18 shows a Thin Layer Chromatography (TLC) analysis. PA: phosphatidic acid (Sigma), PS: Phosphatidylserine (Fluka), PG: Phosphatidylglycerol (Sigma), CAR: Cardiolipin (Sigma), ERG: Ergosterol (Fluka), PE: Phosphatidyl ethanolamine (Sigma), PI: Phosphatidylinosytol (Sigma), PC: Phosphatydilcolina (Sigma), TAG: Triacylclycerides (Sigma).

By this technique it could be determined that both, the CYE-TF (lot 91) at different concentrations 5, 10 and 20 µg/ml) as well as the purified product contain (lot 14.31 at 5, 10 and 20 µg/ml) a complex lipid content, including triacylglycerides, ergosterol, phosphatidylethanoamine, cardiolipin, phosphatidic acid, phophatidylcholine, phosphatidylserine/phosphatidylinositol (FIG. 18). The lipid profile of the rTF-containing microvesicles differs from the profile derived from relipidized rTF obtained by incorporation of rTF into synthetic liposomes following the procedures described by, among others, Waters, E. K. and Morrisey, J. H. (Biochemistry, 2006, 45:3769-3774), Brucato, C. et al (Protein Expression and Purification, 1998, 26:386-393), WO9848283, and Guha, A. et al (Proc. Natl. Acad. Sic. USA, 1986, 83:299-302). Whereas the synthetic liposomes described in all these documents comprise essentially a combination of phosphatidylcholine and phosphatidylserine, or phosphatidylcholine, phosphatidylserine and phosphatidylethanolamine, the yeast-derived microvesicles purified according to the present invention comprise additional components such as ergosterol and cardiolipin which are not found in the rTF-containing liposomes.

Example 3

Production of a Pro-Coagulant Product Based on the Expression of the Full-Length TF His-tag Modified Protein in Yeast (6HT-TF)

3.1. Production of rTF Containing a 6Xhis-Tag at the Carboxyl Terminus

Affinity chromatography purification of proteins containing a histidine tag (his-tag), either at the C or N terminus, is a well standardized method that has been extensively used to obtain highly purified preparations of a large number of proteins. As any chromatographic method, the procedure can be easily scaled-up. For this reason, a rTF containing a 6xhis-tag at the carboxyl terminus has been produced.

3.2. Generation of rTF-his-Tag Plasmid Expression Vector

Figure 19:
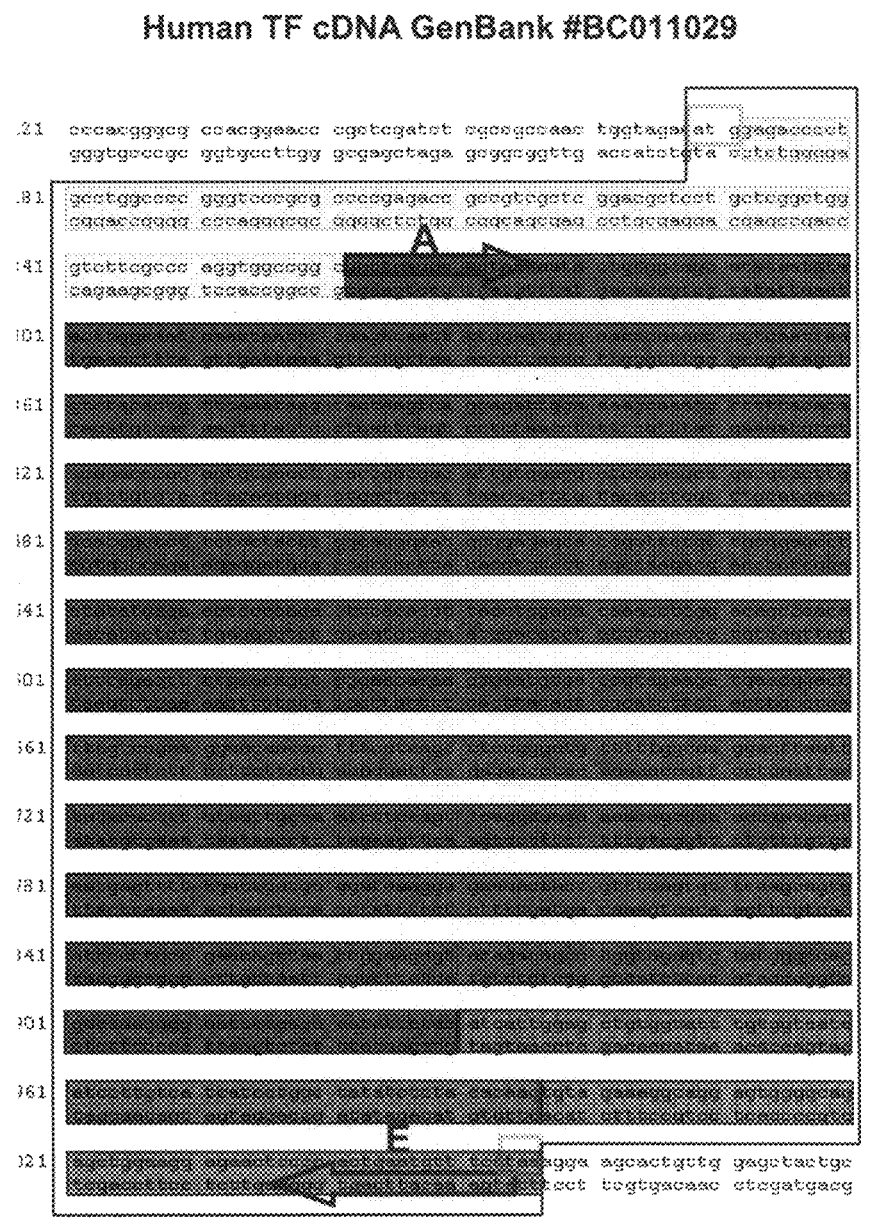

The cDNA coding for the mature hTF protein (aa 33-295) with 18 extra nucleotides (coding for six histidines) at the 3' end, was amplified as a 842-bp fragment by PCR. For this reaction, a similar strategy to that described in Example 1 (Sections 1.2 and 1.3) was followed. Thus, a human placenta cDNA library (Marathon-Ready cDNA, Clontech Laboratories, Inc.) was used as template, and oligonucleotides A and E were used as primers. In oligonucleotide E the termination codon (TAA) of the hTF DNA sequence was substituted by a nucleotide sequence coding for 6 histidines residues followed by a new termination codon (TAG). FIG. 19 shows the location of primers A and E in the hTF DNA sequence (Gene Bank accession # BC011029).

After 35 PCR cycles (94° C., 30 s, 45° C. 30 s, 72° C. 1 min) and a final extension step of 7 min at 72° C., a DNA product with the expected size was purified (Qiagen DNA purification system).

Figure 20:
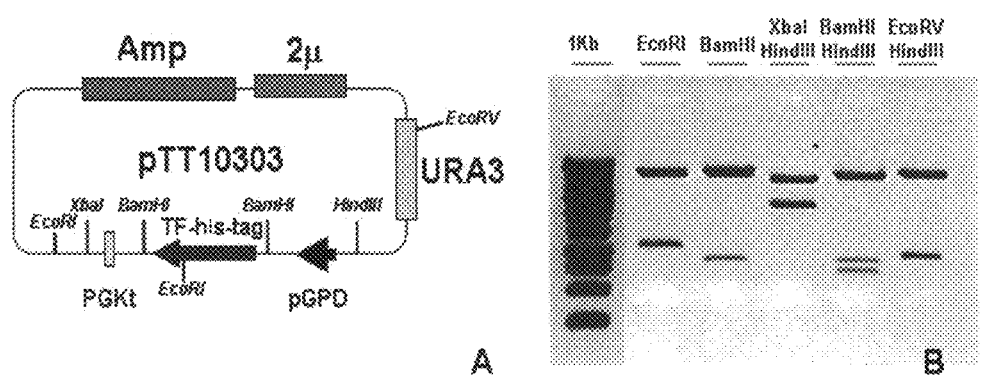
FIG. 20 shows the cloning strategy for the generation of pTT10303.

The DNA fragment amplified by PCR was digested with BamHI to remove the ends, ethanol precipitated, and cloned into pTT10301 vector previously digested with BamHI. After endonuclease restriction analysis of several clones, the plasmid pTT10303, containing the recombinant hTF-his-tag gene in the right orientation with respect to the GDP promoter (pGDP) was selected (FIG. 20).

Inventors further confirmed that the DNA sequence of the recombinant hTF-his-tag cloned into pTT10301 was 100% identical to the previously published hTF DNA sequence (Gene Bank #BC011029) and that it contained the expected 18 extra nucleotides at the 3' end. DNA sequence analysis of the recombinant hTF-his-tag was performed in an automatic sequencer (ABI prism 370, Applied Biosystems) using primers A and E and Big Dye Terminator reagents. DH5α cells carrying the pTT10303 plasmid were grown overnight at 37° C. in LBA medium and used to prepare glycerol stocks.

3.3. Expression of rTF-his-tag

Figure 21:
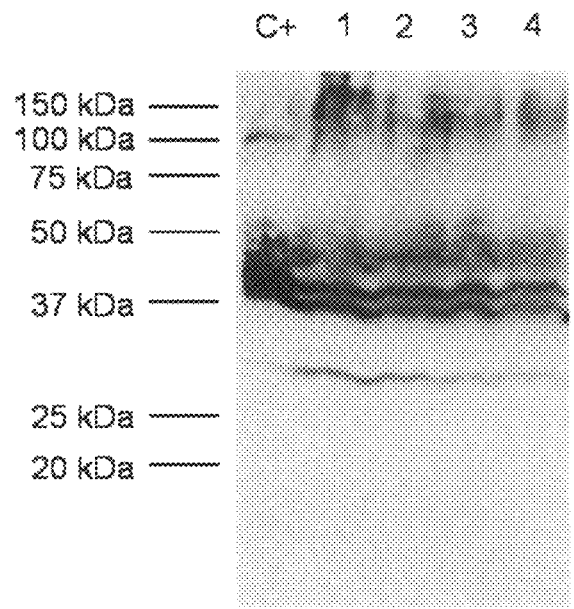
FIG. 21 shows the results of a Western blot analysis of the expression of rTF-his-tag. Western-blot analysis of extracts from cultures of recombinant yeast yTT10302 (lanes 1-4, corresponding to clones 2 to 5) and rTF produced in E. coli (C+). Blot was reacted with the purified mouse anti-human CD142 monoclonal antibody (BD Biosciences Pharmingen). Molecular weight markers in kDa are shown at the left side of the figure.
Figure 22:
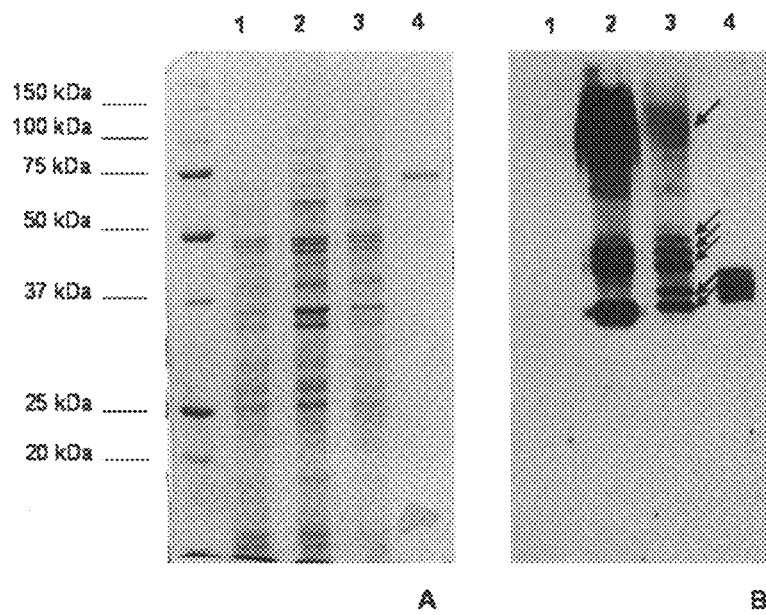
FIG. 22 shows also the results of the expression of rTF-his-tag.

To generate recombinant yeast expressing recombinant mature hTF-his-tag (rTF-his-tag), the expression vector pTT10303 was used to transform T73 ura3⁻ yeast cells as described in Example 1 (Section 1.4). Recombinant yeast clones (named as yTT10302) were selected by their ability of growing in media lacking uracil. Five independent clones of yTT10302 were isolated and cultured overnight in media without uracil. Western-blot analysis showed that all selected clones expressed polypeptides recognized by the anti-human TF mAb (FIG. 21). FIG. 22 shows the rTF-his-tag expression pattern of a selected clone (yTT10302 clone #5) in comparison with extracts from yTT10300 and yTT10301 recombinant yeasts. As it is shown, the molecular sizes of the anti-TF immunoreactive products expressed by yTT10302 were about 36, 38, 45, 47 and 49 kDa (denoted with arrows), while other aggregates of large molecular weight (about 100 to 115 kDa) could also be observed (arrow). As in the case of yTT10301 yeast extracts, these differences in mobility corresponded to different degrees of glycosylation of rTF as it is shown in FIG. 20.

3.4. Purification of rTF-his-Tag by Chromatography 3.4.1. Purification Process

For rTF-his-tag purification, inventors started from clarified extracts containing rTF-his-tag (hereinafter referred to as CYE-6HT-TF) obtained from yTT10302 following the procedure previously described (Example 1, Section 1.5). Said CYE-6HT-TF was filtered through a 0.2 µm pore size filter by tangential flow filtration before being loaded over a 5 ml HiTrap® affinity column (Pharmacia Biotech), that was previously washed with water and equilibrated with start buffer (20 mM phosphate buffer, 500 mM NaCl, pH 7.4). After applying the sample, the flow-through was recovered (unbound material), and the column was subjected to three washes: the first one with 40 ml of start buffer (20 mM phosphate buffer, 500 mM NaCl, pH 7.4); the second wash was with 40 ml of start buffer containing 10 mM imidazol; and the third one with 40 ml of start buffer supplemented with 100 mM imidazol. After the last wash, the microvesiculated rTF-his-tag protein named as 6HT-TF, was eluted by adding to the column 25 ml of start buffer containing 1 M imidazol, and elution fractions (fractions #1, #2, #3, and #4) of 2.5 ml were collected. A general scheme of the process is depicted in FIG. 23.

Figure 24:
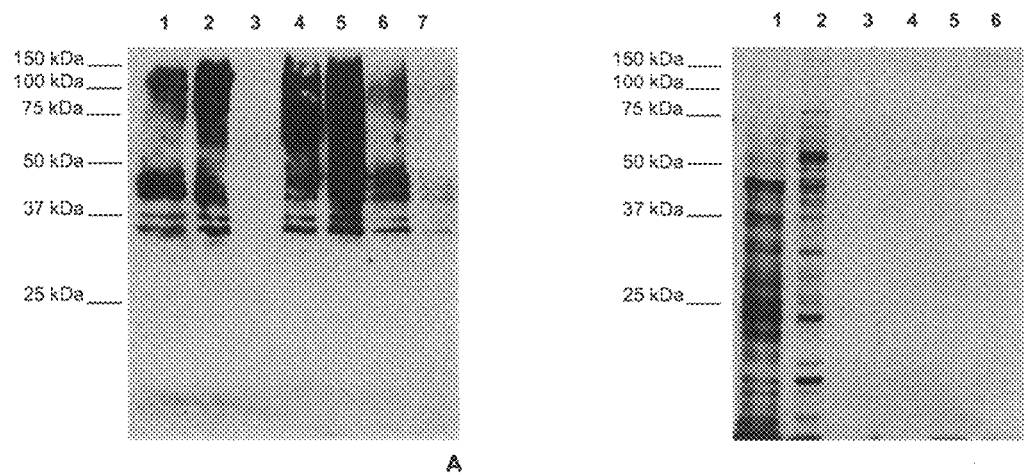
FIG. 24 shows the results of the 6HT-TF purification by affinity chromatography. CYE-6HT-TF was used as starting material. The extract was filtered trough a 0.2 µm pore size filter by tangential filtration and was applied to a 5 ml commercial metal chelate affinity chromatography column (Hi-Trap®, Pharmacia Biotech). The column was subjected to three consecutive washes with start buffer (20 mM phosphate buffer, 500 mM NaCl, pH 7.4) without imidazole, with 10 mM imidazole and with 100 mM imidazol respectively. 6HT-TF was eluted with the same buffer containing 1 M imidazol. 2,5 ml elution fractions (lanes 4 to 7, corresponding respectively to fractions #1, #2, #3, and #4) were collected and dialyzed against 20 mM phosphate buffer, 50 mM NaCl, pH 7.4. The starting filtered yeast extract (lane 1), the unbound material (lane 2), the last wash with starting buffer containing 100 mM and the first four elution fractions were analyzed by SDS-PAGE and Western-blot (FIG. 24A) or silver staining (FIG. 24B). Molecular weight markers in kDa are indicated at the left side of the figure.

These fractions were dialyzed in dialysis buffer (20 mM phosphate buffer, 50 mM NaCl, pH 7.4), and the starting extract, unbound material, last wash before elution and the dialyzed four elution fractions were analyzed by SDS-PAGE and silver staining or by Western-blot. As shown in the Western-blot in FIG. 24A, after binding to the column 6HT-TF, the product can be successfully recovered mainly in the first three elution fractions (lanes 4-6). Noteworthy, when proteins from the same samples were visualized by silver staining of the gel (FIG. 24B), protein bands could only be observed in the lanes corresponding to the starting yeast extract (lane 1) and to the unbound material (lane 2), but not in the eluted fractions (lanes 4-7). In addition, the amount of total protein in these samples was under the detection limit of the standard BCA reagent (20 µg/ml).

These results, together with the result of the Western-blot, clearly demonstrated that highly purified 6HT-TF product could be obtained by this affinity chromatography procedure. Most important, the dialyzed elution fractions #1-3 maintained the pro-coagulant activity, determined as described in EXAMPLE 4, and strikingly, fraction #1 showed essentially the same pro-coagulant activity as the starting extract CYE-6HT-TF. As expected, the fraction containing less amount of immunoreactive rTF protein (fraction #4, lane 7) did not show any pro-coagulant activity.

The differences between total protein concentration vs. activity in these two samples can be summarized as follows

|  | Concentration of total protein (mg/ml) | Concentration of rTF (ng/ml) |
|---|---|---|
| CYE-6HT-TF | 6.2 | 275 |
| fraction #1 6HT-TF | ND* | 252 |

ND*: not detectable by a standard colorimetric assay (BCA) (detection limit 20 µg/ml)

3.4.2. Analytical Methods

Figure 25:
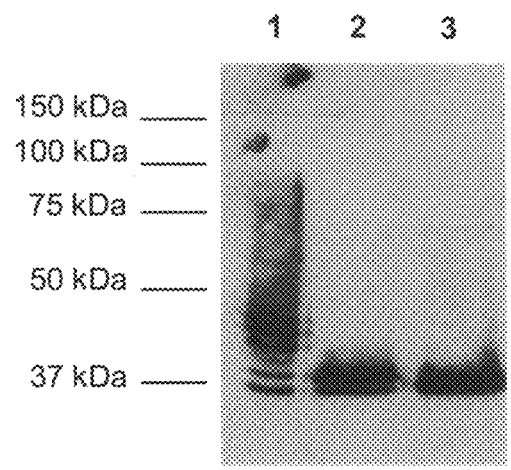
FIG. 25 shows the results of a Western blot analysis of the purified 6HT-TF after endoglycosylase treatment. Purified fraction of 6HT-TF was treated with 500 units of PNGase F (lane 2) or Endo H (lane 3) following the manufacturer instructions. These samples and the untreated eluate (lane 1) were analyzed by Western blot with an anti-human TF mAb. Molecular weigh markers in kDa are shown at the left side of the figure.

As shown in the Western-blot of FIG. 19 the 6HT-TF product in the eluted fractions consisted, like in the whole yeast extract, of several protein bands varying in size that were likely originated by differential glycosylation of the rTF-his-tag protein. To study this possibility, the eluted fraction #1 was subjected to endoglycosylase treatment. Briefly, extracts from rTF-expressing yeast (yTT10301) treated with 500 units (U) of endoglycosydase H (Endo H) or N-glycosydase F (PNGase F) for 1 h at 37° C. were further analysed by Western-blot with the anti-human TF mAb. FIG. 25 shows that after treatment with either PNGase F (lane 2) or Endo H (lane 3) the 45, 47 and 49 kDa protein bands disappeared with both treatments. After PNGase F incubation only two polypeptides were observed, the 36 and the 38 kDa that was augmented most likely due to the deglycosylation of the 45, 47 and the 49 kDa products (compare lanes 1 and 2). Treatment with Endo H gave rise to a unique immunoreactive product of 36 kDa (lane 3), that should corresponded to the unglycosylated rTF-his-tag protein.

Figure 26:
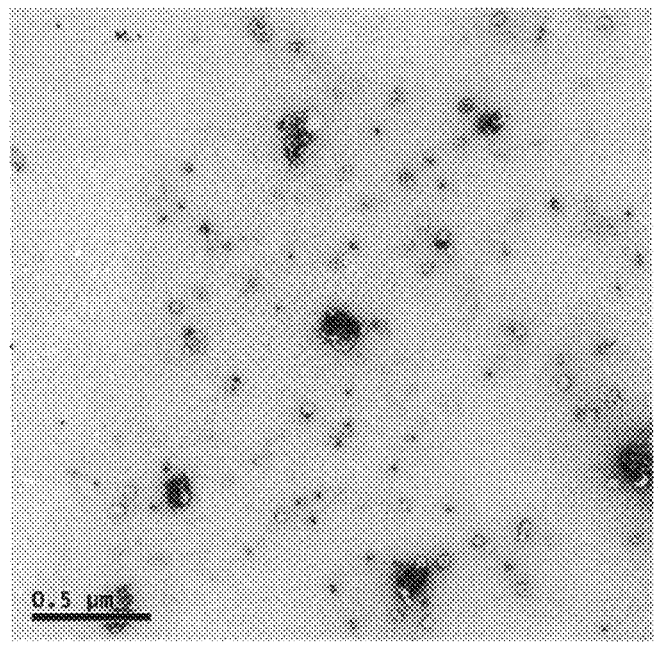
FIG. 26 shows the results of an immunoelectronmicroscopy of purified 6HT-TF by affinity chromatography. The first elution fraction was adsorbed to colloidon-coated copper grids. The grid was treated for immunogold labeling with anti-TF monoclonal antibody.

In addition, purified 6HT-TF was analyzed by EM after being subjected to immunostaining with anti-human TF mAb as described in Example 1 (Section 1.6). As shown in FIG. 26, a large number of gold particles, most of which were associated to small vesicles of regular size, can be observed. In a similar sample from non-rTF expressing yeast, analyzed in parallel, the number of gold particles was extremely reduced (not shown). This result indicates that the affinity chromatography procedure used to purify the 6HT-TF product allows the recovery of biologically active 6HT-TF which is associated to yeast-derived membrane microvesicles.

Example 4

Production of a Pro-Coagulant Product Based on the Expression of a Truncated Form of the hTF Protein in Yeasts (CYE-TTF)

Figure 28:
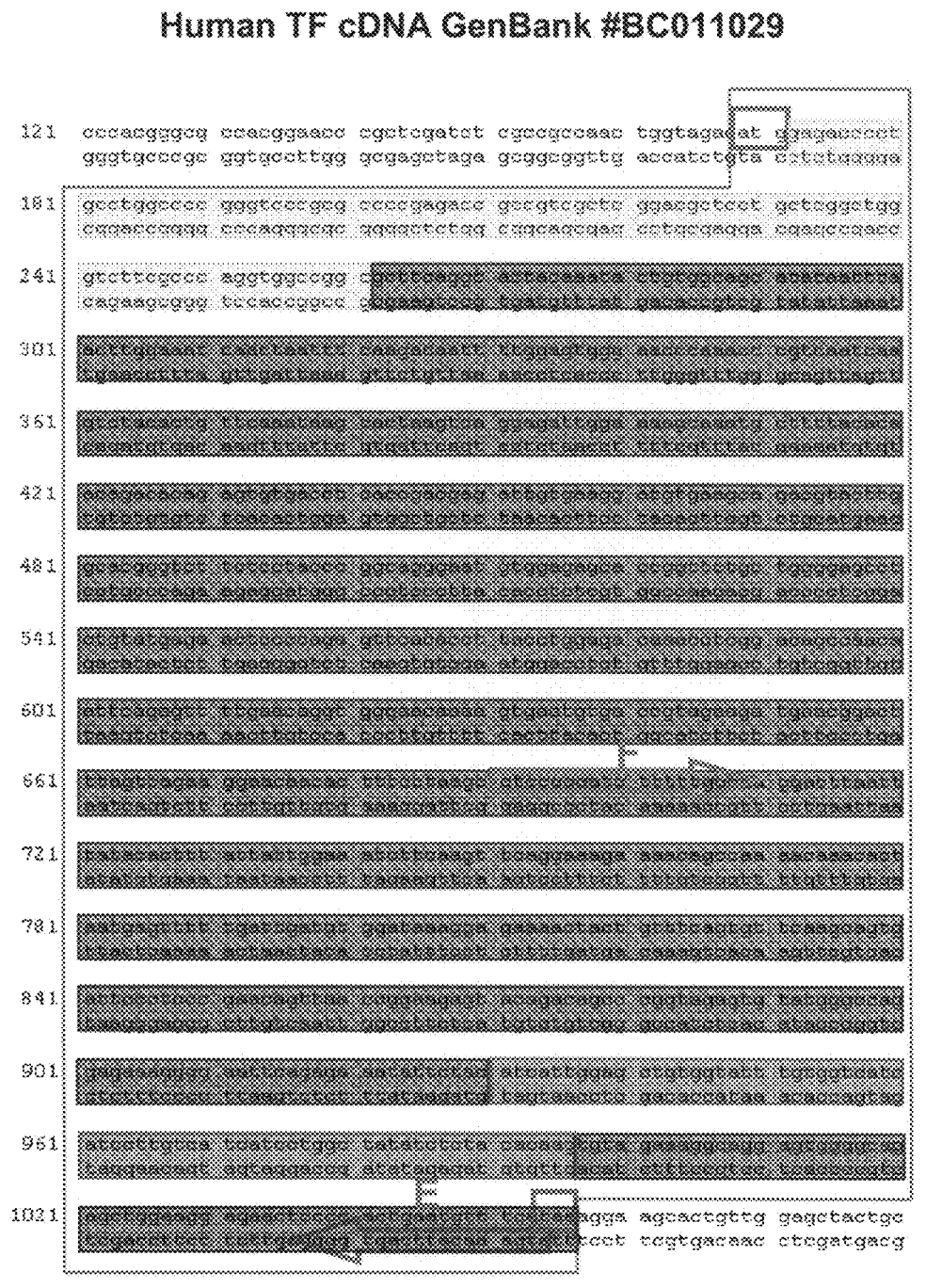

4.1. Generation of the Truncated TF-his-tag (TTF-his-tag) Plasmid Expression Vector The cDNA coding for a truncated form of the hTF protein (TTF), containing the interaction domain to Factor X (aa 174-251), the transmembrane region (aa 252-274), and the cytoplasmic tail (aa 275-295) with 18 extra nucleotides (coding for six histidines) at the 3' end, was amplified as a 398 bp fragment by PCR. A similar strategy to that described in Example 1 (Sections 1.2 and 1.3) was followed. Thus, a human placenta cDNA library (Marathon-Ready cDNA, Clontech Laboratories, Inc.) was used as template, and oligonucleotides F and E were used as primers. In oligonucleotide E, the termination codon (TAA) of the hTF DNA sequence was substituted by a nucleotide sequence coding for 6 histidines residues followed by a new termination codon (TAG). FIG. 28 shows the location of primers F and E in the hTF DNA sequence (Gene Bank accession # BC011029).

After 35 PCR cycles (94° C., 30 s, 45° C. 30 s, 72° C. 1 min) and a final extension step of 7 min at 72° C., a DNA product with the expected size was purified (Qiagen DNA purification system).

Figure 29:
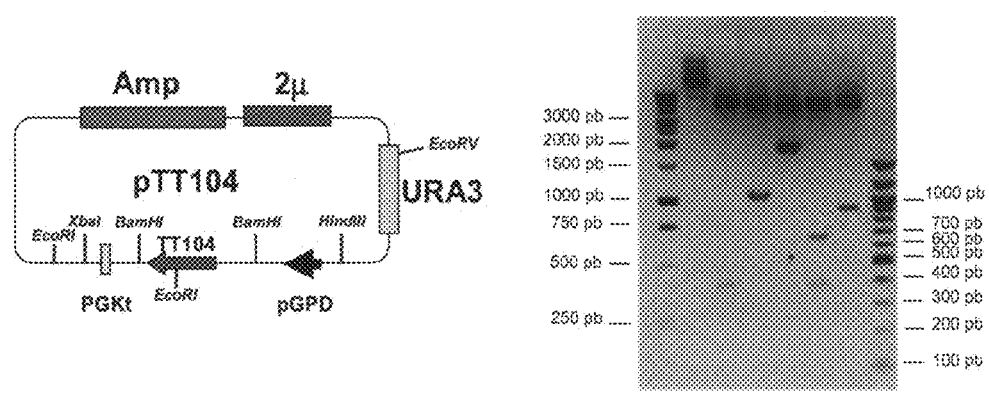
FIG. 29. Cloning strategy for the generation of pTT10304. A) The DNA fragment obtained from the PCR reaction was digested with BamHI and cloned into the pTT10301 plasmid, previously digested with BamHI and dephosphorylated. The resulting plasmid pTT10304 was grown in *E. coli* and purified with the commercial DNA purification JETstar kit (Genomed Gmbh). B) Restriction analysis of the generated pTT10304 vector.

The DNA fragment amplified by PCR was digested with BamHI, to remove the ends, ethanol precipitated, and cloned into pTT10301 vector previously digested with BamHI. After endonuclease restriction analysis of several clones, the plasmid pTT10304 containing the recombinant TTF-his-tag gene in the right orientation with respect to the GDP promoter (PGDP) was selected (FIG. 29).

Inventors further confirmed that the DNA sequence of the rTF-his-tag cloned into pTT10301 was 100% identical to the previously published sequence (Gene Bank #BC011029) and that it contains the expected 18 extra nucleotides at the 3' end (FIG. 25). DH5α cells carrying the pTT10304 plasmid were grown overnight at 37° C. in LBA medium and used to prepare glycerol stocks.

4.2. Expression of rTTF-his-tag by Recombinant Yeast

To generate recombinant yeasts expressing recombinant human truncated TF-his-tag (rTTF-his-tag), the expression vector pTT10304 was used to transform T73 ura3⁻ yeast cells as described in Example 1 (Section 1.4). Recombinant yeast clones (named as yTT10304) were selected by their ability of growing in media lacking uracil.

For rTTF-his-tag expression, clarified yeast extracts (CYE) obtained from yTT10304 following the procedure previously described in Example 1 (Section 1.5), having pro-coagulant activity, named CYE-TTF (i.e., clarified yeast extract (CYE) containing microvesiculated truncated tissue factor (TTF)), were prepared and analyzed for activity as described in EXAMPLE 1.

Example 5

Generation of the N-glycosylation Mutant TF Plasmid Expression Vector

Figure 30:
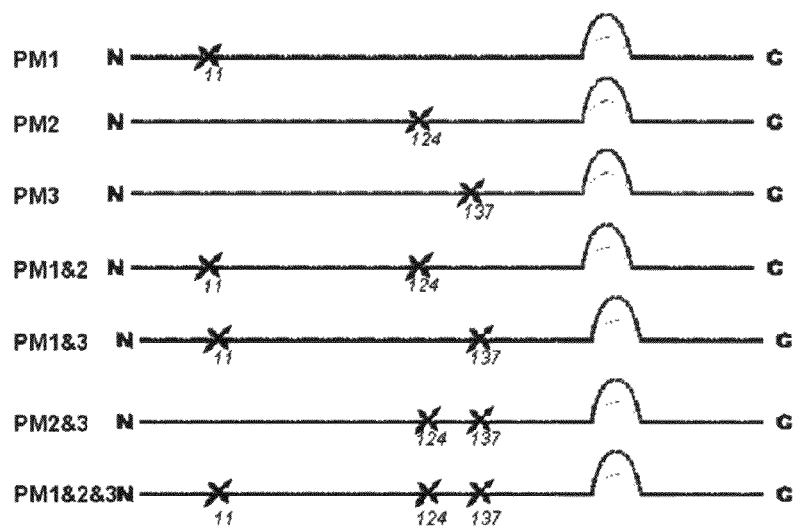
FIG. 30 shows a schematic representation of the position of the point mutations in glycosylation sites in human TF.

TF shows three different residues where N-glycosylation takes place, namely, N11, N124, and N137. Single mutants compromising these residues (N11A, N124A and N137A)

and all the possible combinations thereof constructed using standard procedures (FIG. 30).

Oligonucleotide-Directed Mutagenesis

A standard PCR reaction using the oligonucleotides listed in table 3 has been used to generate the different mutants (Current Protocols in Molecular Biology, chapter 15$^{th}$). Plasmid pTT10302 has been used as DNA template, and Pfu has been used as polymerase since it shows a very high fidelity and low error rate.

TABLE 3

Sequence of the oligonucleotides used to generate the glycosylation mutants in TF.

| Name (SEQ ID NO) | Aminoacid location-change | Direction | Oligo Sequence 5'-3' |
|---|---|---|---|
| TT-7071 (6) | 11-Asn to Ala | Forward | TGACACCGTCGTATACGTAATTGAACCTTTAGT |
| TT7075 (7) | 11-Asn to Ala | Reverse | ACTGTGGCAGCATATCGATTAACTTGGAAATCA |
| TT-7072 (8) | 124-Asn to Ala | Forward | ATCTTCTACGGTCACTGCCACTTTTGTTCCCAC |
| TT-7076 (9) | 124-Asn to Ala | Reverse | GTGGGAACAAAAGTGGCAGTGACCGTAGAAGAT |
| TPM1 (10) | 137-Asn to Ala | Forward | ACTTTAGTCAGTTGGGCAAACACTTTCCTAAGC |
| TPM2 (11) | 137-Asn to Ala | Reverse | GCTTAGGAAAGTGTTTGCCCTTCTGACTAAAGT |

Ala means Alanine, and Asn means Asparagine.

Results

Points Mutations in TF Affecting Glycosylation Sites

Figure 31:
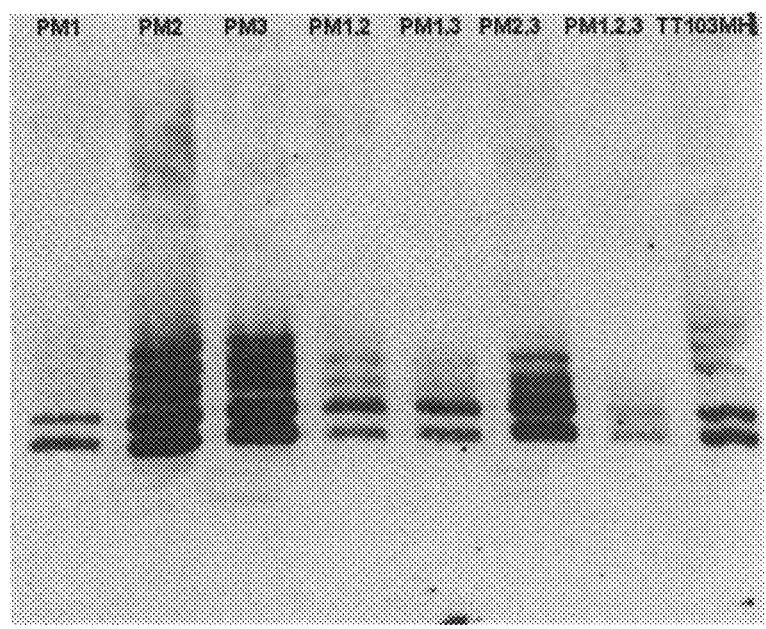
FIG. 31 shows a western blot probed with anti-TF1 antibody. PM1 refers to Ala-Asn change at position 11, PM2 refers to Ala-Asn change at position 124, and PM3 refers to Asn-Ala change at position 137. PM1,2; 1,3; and 1,2,3 refers to combinations of them. TT103 MH is the wild type TF.

FIG. 31 shows an antiTF western blot comparing the profile of the different mutants in glycosylation sites with the wild type. As shown, the profile is different in all of them, and when treated with glycosylases, all the bands become one, which means that the profile observed is due to the different glycosylation state.

The coagulation activity of these mutants has been determined, and the data is summarized in table 4. All the data has been normalized to the wild type, whose activity and expression has been considered as 100. Both single mutations in 11 (PM1) and 124 (PM2) showed an increase in activity, although surprisingly, the most remarkable effect was observed when the residue 124 was mutated, since its activity and expression was significantly increased (6 and 2 fold respectively). The activity of those double mutants and triple mutant where PM2 is involved were also increased.

TABLE 4

Relative activity and expression of the different mutants in glycosylation sites when compared to the wild type 6HT-TF.

| | Relative activity PM/6H-TF*100 | Relative expresion PM/6H-TF*100 |
|---|---|---|
| WT | 100 | 100 |
| PM1 | 190 | 48 |
| PM2 | 602 | 194 |
| PM3 | 64 | 67 |
| PM1&2 | 206 | 52 |
| PM1&3 | 0 | 15 |
| PM2&3 | 114 | 108 |
| PM1&2&3 | 294 | 12 |

PM = Point mutation

Example 6

Evaluation of the Procoagulant Activity of Microvesiculated Tissue Factor (mTF)

For simplicity, in this Example, "microvesiculated tissue factor", "microvesiculated TF" or "mTF" refers, in general, to tissue factor, modified tissue factor (by substitution, elimination, addition or swapping of one or more aminoacids), fusion protein comprising tissue factor, or truncated tissue factor lacking part or all of the union domain to FVIIa, all of them being total or partially glycosylated and associated to yeast derived microvesicles (i.e., being integrated in the lipid layer of the microvesicles) unless otherwise stated.

For the purpose of evaluating the procoagulant activity of microvesiculated tissue factor provided by the instant invention, a series of in vitro and in vivo assays were performed, specifically:

1. In vitro assays demonstrating that microvesiculated TF causes fibrin clot formation and blood coagulation in both healthy and patient conditions
   - 1.1 Coagulation assays in plasma from healthy subjects.
   - 1.2 Comparison of the pro-coagulant effect of vesicles purified by gel-filtration and relipidated TF.
   - 1.3 Coagulation assays in plasmas deficient in FVIII, in FIX or in FXI.
   - 1.4 Coagulation assays in Thrombocytopenic plasmas.
   - 1.5 Coagulation assays in plasma from FVIII, FIX and FXI deficient plasma in the presence of an anti-FVII antibody.
   - 1.6 Coagulation assays in non-anticoagulated whole blood from healthy subjects.
   - 1.7 Coagulation assays in non-anticoagulated whole blood from Hemophilic patients (coagulation assays in non-anticoagulated whole blood).
2. In vivo assays demonstrating that microvesiculated TF is an agent useful for topical antihemorrhagic treatment in severe hemorrhage models (by applying it directly on the previously sectioned blood vessel)
   - 2.1 Assay in a severe hemorrhage animal model by proximal section of rat tails.
   - 2.2 Assay in a severe hemorrhage animal model previously treated with heparin.

3. In vivo assays demonstrating that microvesiculated TF is an agent useful for topical antihemorrhagic treatment in lethal hemorrhage models (by applying directly on the blood vessel previously sectioned)
  3.1 Assay in a lethal hemorrhage animal model by proximal section of FVIII deficient mice tails.

I. Materials and Methods

Materials

As microvesiculated tissue factor (mTF) source three different compounds were used:
  (i) Clarified yeast extracts containing microvesiculated TF (CYE-TF), obtained according to Example 1;
  (ii) purified microvesiculated TF-hexa histidine tag fusion protein (6HT-TF) obtained according to Example 2; and
  (iii) Clarified yeast extract containing microvesiculated truncated tissue factor (CYE-TTF) obtained according to Example 3;

Commercial Coagulation Factor FVIII-, FIX- and FXI-deficient plasmas were purchased from Dade Behring Marburg GmbH.

Commercial monoclonal anti-human FVII antibody (clone HVII-1) was purchased from Sigma Aldrich.

Commercial hemophilic mouses (Allele: $F8^{tm1Kaz}$; common name MFVIII-16; mutated by Haig H Kazazian; Reference: Bi L; Lawler A M; Antonarakis S E; High K A; Gearhart J D; Kazazian H H Jr. 1995. Targeted disruption of the mouse factor VIII gene produces a model of haemophilia A, Nat. Genet. 10:119-21) were purchased to Jackson Laboratory.

Commercial rTF was from American Diagnostica.

Plasma samples from five healthy donors was obtained from the Blood Bank of Vall d'Hebrón Hospital, Department "Banc de Sang i Teixits" (Pg,Vall d'Hebrón, 119-129, 08035 Barcelona). Plasma samples were checked for hepatitis B virus (HBV), hepatitis C virus (HCV), HIV and TPHA and all were negative. The five plasma samples were pooled and frozen at −20 C in 1.5 ml vials until their use.

Methods
Relipidation of rTF

Commercial rTF (American Diagnostica) was relipidated following the standard procedure described by Morrissey (Neuenschwander et al., J. Biol. Chem. (1993) 268, pages 21489-92 in which rTF is incorporated into phospholipid liposomes. The amount of rTF present in the samples was quantitated by the IMUBIND Tissue Factor ELISA Kit from American Diagnostica Inc. (No. 845) and following vendor specifications.

In Vitro Assays

In order to determine if a microvesiculated truncated tissue factor lacks part or the entire union (binding) domain to FVII, and to know if it is still active, firstly, a binding assay of the microvesiculated truncated tissue factor to FVIIa is carried out in order to determine whether binding of microvesiculated truncated tissue factor to FVIIa can be detected or not, and, secondly, the coagulation assay in plasma can be used to determine if the microvesiculated truncated tissue factor is still active as a procoagulant.

Binding Assay of Microvesiculated Truncated Tissue Factor to FVIIa

To determine the interaction between either purified microvesiculated TF-hexa histidine tagged fusion protein (6HT-TF), clarified yeast extracts containing microvesiculated TF (CYE-TF) or clarified yeast extracts containing microvesiculated truncated TF (CYE-TTF) and the Coagulation Factor VIIa (FVIIa) the authors of the invention followed a modified version of the method described in the International Publication WO 00/04148. By these means, binding of 6H-TF, CYE-TF or CYE-TTF to biotinylated FVIIa was assayed as an ELISA test. For this, biotinylated FVIIa (BEGR-7a) was prepared as described previously (Kelley et al., 1995 Biochem. 34:10383-10392). Then, 96 well microtiter plates were coated with BEGR-7a using streptavidin as a capture agent. Wells were washed twice with 0.05% Tween 20 in distilled water and blocked with PBS containing 1% non-fat dry milk (blocking solution) during 2 h. After that, ten fold dilutions of 6HT-TF, CYE-TF or CYE-TTF, starting at a concentration of 10 µg/ml, prepared in TNC buffer (20 mM Tris, pH 7.5, 100 mM NaCl, 5 mM $CaCl_2$), and containing a fixed amount of either streptavidin conjugated BEGR-7a or streptavidin alone, were added to the wells. After 2 h incubation at R/T, wells were washed again with 0.05% Tween 20 to eliminate unbound material. To detect the TF-FVIIa complex in the different TF-containing solutions a specific anti-TF rabbit polyclonal antisera was used. For this, a 1:500 dilution of the anti-TF sera dilution was added to the wells and incubated 2 h at 37° C. Plates were washed five times before the detection antibody was added. Peroxidase-conjugated goat anti-rabbit immunoglobulin G (IgG) antibody (Southern Biotechnology Associated) was diluted 1:1000 in blocking solution and incubated for 1 h at 37° C. The plates were washed again five times and hydrogen peroxide and ortophenylenediamine (OPD) 0.05% were used to develop the reaction. After 10 to 15 min of incubation at R/T, the reaction was stopped by the addition of $H_2SO_4$ (2N) and absorbance was measured at 492 nm on a Multiskan Plus plate reader (labsystem).

Coagulation Assays in Plasma

Spontaneous procoagulant activity (unstimulated) in plasma was measured by means of a two-step coagulation assay in a 4-channel coagulometer (Start 4, Diagnostica Stago). Briefly, 50 µl of platelet-poor plasma were added to the already tempered cuvettes and 50 µl of the sample (mTF, or distilled water as control) were added. This mixture was left to incubate for 60 seconds at 37° C. and 50 µl of 25 mM calcium chloride were immediately added and the coagulation time was determined in seconds in the coagulometer, verified by formation of the clot. Platelet-poor plasmas were obtained by centrifugation and number of platelets was determined by Coulter.

The procoagulant effect of mTF on coagulation factors deficient plasmas (FVIII, FIX or FXI) corresponding to Haemophilia A, B or C, respectively, was investigated by using commercial plasmas (Dade Behring Marburg GmbH) depleted by means of immunoaffinity techniques. In each case, the final content of said coagulation factors was less than 1%.

The procoagulant effect in a thrombocytopenic like condition was investigated in plasma depleted from platelet with a sequential centrifugation process.

Coagulation Assays in Whole Blood

Procoagulant activity in non-anticoagulated whole blood was determined by means of a coagulation method. The different agents (mTF) to be studied were added in 0.2 ml final volume to 0.8 ml of non-anticoagulated whole blood and coagulation time was measured with a chronometer from the beginning of the extraction until a stable and consolidated blood clot appeared. The effect of the different agents was evaluated by means of their shortening or lengthening of blood coagulation times.

Whole blood samples were obtained from patients or healthy volunteers.

In vivo Assays
Severe Hemorrhage Model by Rat Tail Proximal Section

Sprage-Dawley male rats weighing 300-600 grams were randomly distributed in 2 treatment groups:
  a control group, made up of at least 3 animals which received topical treatment with physiological saline solution, and a second group, also made up of at least 3 animals, which received topical treatment with mTF.

All the compounds came into topical contact with the proximal section of the animal's tail to hemostastically act in a volume of 1 ml/min dispensed directly on the wound surface with the rat in a face-up position. Formation of the stable and consolidated clot was evidenced by means of confirmation of no further bleeding.

Severe Hemorrhage Model by Rat Tail Proximal Section in Animals Treated with Anticoagulant Drugs a) 6HT-TF Treated Animals Sprage-Dawley male rats weighing 300-600 grams were randomly distributed in 2 treatment groups:

a control group, made up of 14 animals which received topical treatment with physiological saline solution, and a second group made of 5 animals which received 200 U/kg of heparin intravenously (i.v.) 15 minutes before to start tail transection procedure. This group was treated after 15 minutes with mTF (6HT-TF) 1494 ng/ml. mTF came into topical contact with the proximal section of the animal's tail to hemostastically act dispensed drop by drop by a plastic eppendorf pipette.

Formation of the stable and consolidated clot was evidenced by means of confirmation of no further bleeding.

b) CYE-TF Treated Animals

27 Sprage-Dawley male rats weighing 300-600 grams were randomly distributed in 5 treatment groups:

a control group, made up of 14 animals which received topical treatment with physiological saline solution;

two groups received 200 U/kg of heparin i.v. 15 minutes before to start tail transection procedure (to be treated with CYE-TF (n=3), and to be treated with physiological saline solution (n=5)), and other two groups received orally 0.1 mg/kg/day of warfarin during three days before to start tail transection procedure (to be treated with CYE-TF (n=3) and to be treated with physiologically saline solution (n=2)).

Therefore, there was a control treated group for each anticoagulation treatment. CYE-TF came into topical contact with the proximal section of the animal's tail to hemostastically act dispensed by a plastic eppendorf pipette. Formation of the stable and consolidated clot was evidenced by means of confirmation of no further bleeding.

Lethal Hemorrhage Model by Mice Tail Proximal Section Using Factor VIII Deficient Mice The purpose of this assay was to assess the effects of topic administration of mTF in a lethal hemorrhage model (tail vein transection) using Factor VIII—deficient mice (Hemophilia A) obtained by gene targeted mutation.

Mice that were homozygous for the targeted, X chromosome-linked mutant allele, were viable and fertile. Homozygous females and carrier males had less than 1% of normal Factor VIII activity and exhibited prolonged clotting times. These mice recapitulated key features of Haemophilia A and provided an excellent model for use in exploring alternative therapy strategies.

There were 5 treatment groups, with 3 to 5 mice per group, as follows:

| Group | Mice | Treatment | Dose |
|---|---|---|---|
| Group A: | Control mice | Vehicle | 0 ng/ml |
| Group B: | Hemophilic male mice | Vehicle | 0 ng/ml |
| Group C: | Hemophilic male mice | mTF | 1,494 ng/ml |
| Group D: | Hemophilic female mice | Vehicle | 0 ng/ml |
| Group E: | Hemophilic female mice | mTF | 1,494 ng/ml |

The mTF stock protein concentration was 1,494 ng/ml biologically active material. Only one dose was used directly from the stock container and no dilution was performed. Test article doses were calculated based on biologically active protein concentration using a two step coagulation assay. mTF and vehicle were administered topically on the site of the mice tail's hemorrhage drop by drop with a rate of 0.25 ml/minute for a maximum of 20 minutes (5 ml).

II. Results

1. In Vitro Assays Demonstrating that Microvesiculated TF Causes Blood Coagulation in Both Healthy and Patient Conditions Several in vitro assays were performed for the purpose of evaluating mTF capacity to cause fibrin clot in healthy and hemophilic subjects at different concentrations. As previously mentioned, "coagulation time" refers to the time the clot takes to consolidate in a non-anticoagulated blood sample.

1.1 Microvesiculated TF is Able to Coagulate Plasma from Healthy Subjects (Coagulation Assays in Plasma)

Direct assay for mTF procoagulant activity in healthy plasma at different concentrations demonstrated that mTF is able to decrease very significantly the coagulation time in healthy plasma conditions, in a clear dose-response way. Even at very low mTF concentrations (2 ng/ml) the coagulation time of healthy plasma is reduced almost in 3 fold times. At higher concentrations (100 ng/ml) it is reduced in more than 5 fold times. Table 5 shows the results in three independent experiments for purified microvesiculated TF-hexa histidine tag fusion protein (6HT-TF), Table 6 for clarified yeast extracts containing microvesiculated TF (CYE-TF), and Table 7 for clarified yeast extract containing microvesiculated truncated TF (CYE-TTF).

TABLE 5

Purified microvesiculated TF-hexa histidine tag fusion protein (6HT-TF) decreases coagulation time in healthy plasma in a dose-response way

| 6HT-TF (ng/ml) | Coagulation time (seconds) |
|---|---|
| 0.00 | 168.60 ± 6.06 |
| 2.00 | 63.27 ± 2.17 |
| 5.00 | 55.56 ± 0.76 |
| 20.00 | 45.47 ± 0.92 |
| 50.00 | 37.50 ± 0.75 |
| 100.00 | 31.10 ± 0.12 |

Mean ± SEM (n = 3)

TABLE 6

Clarified yeast extracts containing microvesiculated TF (CYE-TF) decreases coagulation time in healthy plasma in a dose-response way

| CYE-TF (ng/ml) | Coagulation time (seconds) |
|---|---|
| 0.00 | 320.4 ± 81.3 |
| 0.43 | 67.35 ± 4.6 |
| 4.30 | 37.6 ± 1.9 |
| 43.00 | 23.1 ± 1.09 |
| 209 | 18.08 ± 0.26 |

Mean ± SEM (n = 4)

TABLE 7

Clarified yeast extracts containing microvesiculated truncated TF (CYE-TTF) decreases coagulation time in healthy plasma

| CYE-TTF (ng/ml) | Coagulation time (seconds) |
|---|---|
| 0.00 | 233.4 ± 2.65 |
| 20.00 | 85.6 ± 1.1 |

Mean ± SEM (n = 2)

1.2 Microvesiculated TF is Able to Coagulate Plasma with Improved Efficiency when Compared to rTF Relipidated Following Standard Procedures.

1.2.1. Pro-Coagulant Activity of mTF Compared to Commercial rTF Relipidated Following Standard Procedures.

Commercial rTF (American Diagnostica) was relipidated following the standard procedure described by Morrissey (Neuenschwander et al., J. Biol. Chem. (1993) 268, pages 21489-92 in which rTF is incorporated into phospholipid liposomes. Plasma samples from five healthy donors was obtained from the Blood Bank of Vall d'Hebron Hospital, Department "Banc de Sang i Teixits" (Pg,Vall d'Hebron, 119-129, 08035 Barcelona). Plasma samples were checked for hepatitis B virus (HBV), hepatitis C virus (HCV), HIV and TPHA and all were negative. The five plasma samples were pooled and frozen at −20 C in 1.5 ml vials until their use. The amount of rTF present in the samples was quantitated by the IMUBIND Tissue Factor ELISA Kit from American Diagnostica Inc. (No. 845) and following vendor specifications.

Figure 32:
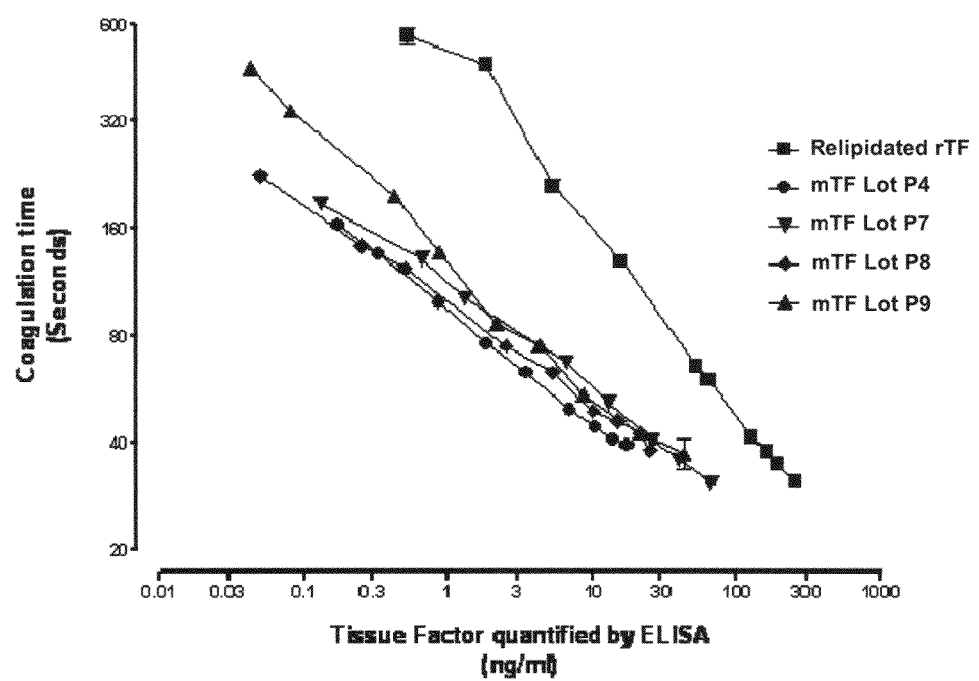
FIG. 32. Dose-response curves of the procoagulant activity of TT-103 and relipidated rTF.—The procoagulant activity was measured in a coagulometer using pooled normal human plasma and different concentrations of either TT-103 from different pools or relipidated rTF.

First, it was analyzed the possible differences in activity between rTF incorporated into yeast microvesicles or when it inserted into synthetic liposomes. For these experiments four different lots of mTF (Lots P4, P7, P8 and P) and one lot of in vitro relipidated rTF, all of them with known concentrations of rTF as determined by ELISA, were tested for coagulant activity. Thus, serial dilutions of either mTF (from the four different lots) or the relipidated commercial rTF were tested for activity in a standard coagulation test. The result showed that over the whole range of concentrations tested, and independently of the pool tested, the procoagulant activity in mTF samples was always higher (between one or two orders of magnitude) than that of the corresponding dilutions of relipidated rTF (FIG. 32).

1.2.2. Pro-Coagulant Activity of the rTF Inserted into Yeast-Derived Microvesicles (mTF) Compared to the Same rTF Inserted into Synthetic Liposomes.

Figure 33:
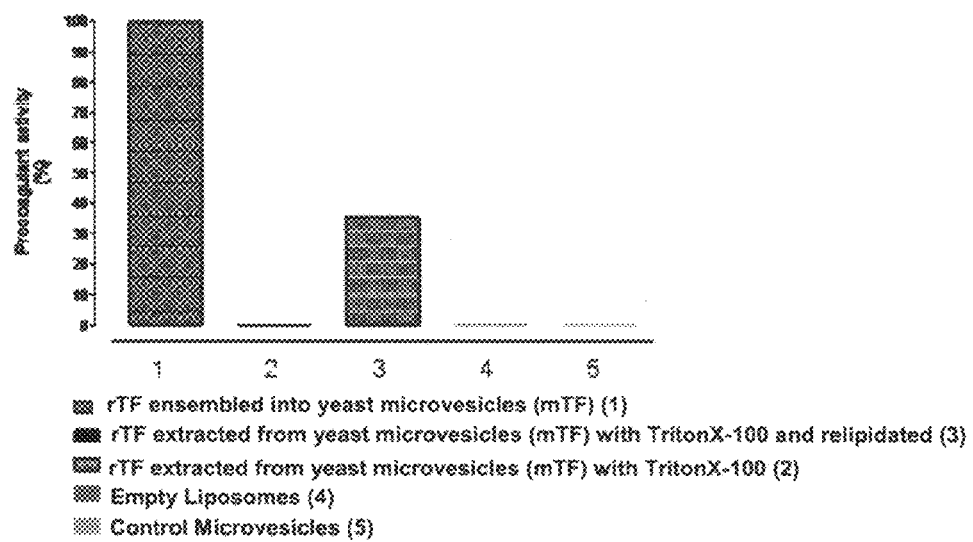
FIG. 33 shows the procoagulant activities in vitro of untreated TT-103 (1), TT-103 being submitted to Triton X-100 treatment (2), TT-103 being submitted to Triton X-100 treatment after dyalisis, allowing relipidation of rTF (3), empty liposomes (4) and microvesicles from non-expressing rTF recombinant yeast (5). The amount of rTF determined by ELISA was the same (120 ng/mL) in samples 1, 2 and 3.

Efforts to relipidate rTF extracted from mTF microvesicles have shown that the rTF activity is greatly reduced when compared to the original yeast microvesicles containing rTF (FIG. 33). There appears to be a conformational requirement for optimal tissue factor activity.

1.2.3. Pro-Coagulant Activity of mTF in Heparinized Plasma

Figure 34:
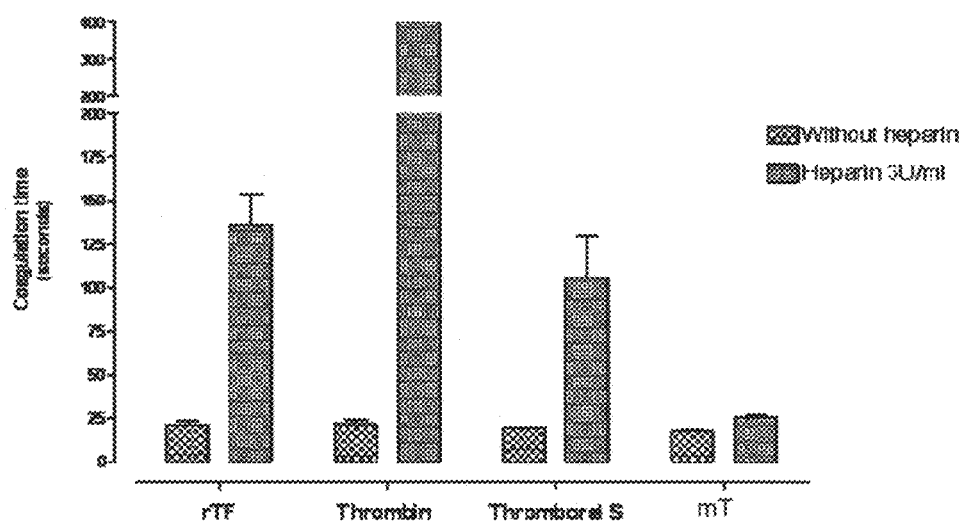
FIG. 34 shows the pro-coagulant activity of TT-103 in heparinized plasma (TT-103) compared to relipidated rTF, thrombin and Thromborel S.

Additionally, the activity present in reconstituted preparations was negligible in certain in vivo models (heparinized animals) of hemorrhage (FIG. 34).

Taken together, the results shown in 1.2 indicate that the unique combination of tissue factor and yeast membranes present in the mTF or 6H-TF microvesicles according to the invention display an array of haemostatic activities that cannot be achieved by the conventional in vitro insertion of rTF into synthetic liposomes.

1.3. Microvesiculated TF is Able to Coagulate Plasma from FVIII FIX and FXI-Deficient Patients (Coagulation Assays in Plasma)

Direct assay for mTF procoagulant activity in coagulation factor FVIII (Hemophilia A), FIX (Hemophilia B), and FXI (Hemophilia C) deficient plasmas obtained by immunodepletion at different concentrations demonstrated that mTF is able to decrease very significantly the coagulation time in hemophilic conditions, in a clear dose-response way. Even at very low mTF concentrations (2 ng/ml) it succeeded in provoking coagulation of plasmas depleted of FVIII, FIX or FXI. At higher concentrations (100 ng/ml), mTF reduces the coagulation time in depleted plasmas at the same level than in healthy plasmas. Table 8 shows the results in 3 independent experiments for purified microvesiculated TF-hexa histidine tag fusion protein (6HT-TF), and Table 9 shows the results for clarified yeast extracts containing microvesiculated TF (CYE-TF).

TABLE 8

Purified microvesiculated TF-hexa histidine tag fusion protein (6HT-TF) decreases coagulation time in coagulation factor FVIII (Hemophilia A), FIX (Hemophilia B), and FXI (Hemophilia C) deficient plasmas in a dose-response way

| 6HT-TF (ng/ml) | FVIII (Hemophilia A) Coagulation time (seconds) | FIX (Hemophilia B) Coagulation time (seconds) | FXI (Hemophilia C) Coagulation time (seconds) |
|---|---|---|---|
| 0.00 | 600 ± 0.0 | 600 ± 0.0 | 600 ± 0.0 |
| 2.00 | 87.43 ± 3.01 | 78.37 ± 0.82 | 66.43 ± 2.17 |
| 5.00 | 57.43 ± 1.68 | 52.20 ± 0.69 | 51.67 ± 0.64 |
| 20.00 | 48.57 ± 1.23 | 41.70 ± 1.18 | 46.07 ± 1.70 |
| 50.00 | 39.80 ± 0.67 | 34.40 ± 0.42 | 38.93 ± 1.23 |
| 100.00 | 32.77 ± 0.38 | 29.17 ± 0.43 | 32.50 ± 0.85 |

Mean ± SEM (n = 3)

TABLE 9

Clarified yeast extracts containing microvesiculated TF decreases coagulation time in coagulation factor FVIII (Hemophilia A), FIX (Hemophilia B), and FXI (Hemophilia C) deficient plasmas in a dose-response way

| CYE-TF (ng/ml) | FVIII (Hemophilia A) Coagulation time (seconds) | FIX (Hemophilia B) Coagulation time (seconds) | FXI (Hemophilia C) Coagulation time (seconds) |
|---|---|---|---|
| 0.00 | >600 | >600 | <600 |
| 0.043 | 127.9 ± 0 | 126.7 ± 1.2 | — |
| 0.43 | 63.25 ± 5 | 64.15 ± 5 | 130.2 ± 0 |
| 4.3 | 34.65 ± 2.65 | 35.47 ± 2.57 | 36.9 ± 4.0 |
| 43.0 | 20.15 ± 1.05 | 20.6 ± 1.4 | 20.85 ± 1.15 |

Mean ± SEM (n = 2)

1.4. Microvesiculated TF is Able to Coagulate Plasma from Acquired Platelet Deficiency (Coagulation Assays in Thrombocytopenic Plasma)

Direct assay for mTF procoagulant activity in plasma from acquired platelet deficiency demonstrated that mTF is able to decrease very significantly the coagulation time in Thrombocytopenic plasmas with different platelet counts. Even at very low platelet counts (<1,000/µl) the coagulation time is drastically reduced by clarified yeast extracts containing microvesiculated TF (CYE-TF), as shown in Table 10.

TABLE 10

Clarified yeast extracts containing microvesiculated TF (CYE-TF) decreases coagulation time in thrombocytopenic plasmas

| Platelet count | Without mTF Coagulation time (seconds) | With CYE-TF (60 ng/ml) Coagulation time (seconds) |
|---|---|---|
| 350,000/µl | 226.3 | 21.9 |
| 150,000/µl | 232.6 | 22.8 |
| 50,000/µl | 253.9 | 22.4 |
| 9,000/µl | 321.2 | 21.3 |
| <1,000/µl | >400 | 21.3 |

Mean ± SEM (n = 1)

1.5. Microvesiculated TF is Able to Coagulate Plasma from FVIII, FIX and FXI Deficient Plasma in the Presence of an Anti-FVII Antibody (Coagulation Assays in Plasma)

The effect of microvesiculated TF on plasma coagulation was investigated by means of coagulation assays using FVIII, FIX and FXI deficient plasmas (FVIII DP, FIX DP and FXI DP) from healthy volunteers in the presence of a monoclonal antibody against FVII. The results clearly show that clarified yeast extracts containing microvesiculated TF (CYE-TF) is able to produce plasma coagulation, even extraordinarily reducing coagulation time even in the absence of FVIII, FIX or FXI and in the presence of a monoclonal antibody against FVII, as shown in Table 11. The coagulation in the absence of FX, and in the presence of FVII antibodies means that, surprisingly, mTF is not acting through intrinsic nor through extrinsic coagulation pathways.

TABLE 11

Clarified yeast extracts containing microvesiculated TF (CYE-TF) coagulates FVIII, FIX and FXI deficient plasmas in the presence of anti-FVII antibodies

| | Without mTF Coagulation time (seconds) | With CYE-TF (70 ng/ml) Coagulation time (seconds) |
|---|---|---|
| FVIII DP | 308.17 ± 5.41 | 29.6 ± 4.85 |
| FIIIV DP + anti FVII | >395 | 45.9 ± 0.86 |
| FIX DP | 347.4 ± 23.03 | 26.77 ± 3.97 |
| FIX DP + anti FVII | >400 | 41.67 ± 0.55 |
| FXI DP | 331 ± 5.43 | 32.9 ± 5.8 |
| FXI DP + anti FVII | >400 | 49.17 ± 1.2 |
| Normal Plasma | 126.28 ± 85 | 28.15 ± 0.05 |
| Normal Plasma + anti FVII | 216.8 ± 0 | 42.55 ± 2.05 |

Mean ± SEM (n = 4)

1.6 Microvesiculated TF is Able to Coagulate Blood from Healthy Subjects (Coagulation Assays in Non-Anticoagulated Whole Blood)

Direct assay for mTF procoagulant activity in whole blood from healthy subjects at different concentrations demonstrated that mTF is able to decrease very significantly the coagulation time in a clear dose-response way. Even at very low mTF concentrations (1 ng/ml) it succeeded in reducing the coagulation time of whole blood from healthy subjects. At higher concentrations (100 ng/ml), mTF reduces the coagulation time in depleted plasmas in more than 8 fold times. Table 12 shows the results in three independent experiments for purified microvesiculated TF-hexa histidine tag fusion protein (6HT-TF), and Table 13 shows the results for clarified yeast extracts containing microvesiculated TF (CYE-TF).

TABLE 12

Purified microvesiculated TF-hexa histidine tag fusion protein decreases coagulation time in whole blood from healthy patients in a dose-response way

| 6HT-TF (ng/ml) | Coagulation Time (minutes) |
|---|---|
| 0.00 | 4.23 ± 0.54 |
| 1.00 | 2.03 ± 0.14 |
| 10.00 | 1.17 ± 0.12 |
| 100.00 | 0.33 ± 0.03 |

Mean ± SEM (n = 3)

TABLE 13

Clarified yeast extracts containing microvesiculated TF (CYE-TF) decreases coagulation time in whole blood from healthy patients in a dose-response way

| CYE-TF (ng/ml) | Coagulation Time (seconds) |
|---|---|
| 0.00 | 264.7 ± 33.4 |
| 0.043 | 235.0 ± 37.5 |
| 0.43 | 168.3 ± 14.2 |
| 4.30 | 76.6 ± 12.1 |
| 43.0 | 43.3 ± 8.8 |
| 208 | 23.0 ± 3.0 |

Mean ± SEM (n = 3)

1.7 Microvesiculated TF is Able to Coagulate Blood from Hemophilic Patients (Coagulation Assays in Non-Anticoagulated Whole Blood)

Direct assay for mTF procoagulant activity in whole blood from Hemophilic patients at different concentrations demonstrated that mTF is able to decrease very significantly the coagulation time in a clear dose-response way. Even at low mTF concentrations (2-5 ng/ml) it succeeded in normalizing the coagulation time of whole blood from hemophilic patients. At higher concentrations (20 ng/ml), mTF reduces the coagulation time in hemophilic whole blood to less than a minute. Table 14 shows the results in three independent experiments for purified microvesiculated TF-hexa histidine tag fusion protein (6HT-TF), and Table 15 shows the results for clarified yeast extracts containing microvesiculated TF (CYE-TF).

TABLE 14

Purified microvesiculated TF-hexa histidine tag fusion
protein (6HT-TF) decreases coagulation time in whole blood
from Hemophilic A and B patients in a dose-response way

| 6HT-TF (ng/ml) | FVIII (Hemophilia A) Coagulation Time (minutes) | FXI (Hemophilia B) Coagulation Time (minutes) |
|---|---|---|
| 0.00 | 17.17 ± 1.56 | 19.27 ± 0.84 |
| 1.00 | 8.50 ± 0.47 | 11.23 ± 0.65 |
| 10.00 | 3.93 ± 0.30 | 6.40 ± 0.32 |
| 100.00 | 0.80 ± 0.12 | 0.77 ± 0.15 |

Mean ± SEM (n = 3)

TABLE 15

Clarified yeast extracts containing microvesiculated TF
(CYE-TF) decreases coagulation time in whole blood from
Hemophilic A and B patients in a dose-response way

| CYE-TF (ng/ml) | FVIII (Hemophilia A) Coagulation Time (minutes) | FXI (Hemophilia B) Coagulation Time (minutes) |
|---|---|---|
| 0.00 | 15.3 ± 1.2 | 18.4 ± 2.1 |
| 1.00 | 9.8 ± 1.3 | 11.2 ± 0.1 |
| 10.00 | 5.7 ± 0.7 | 5.8 ± 0.3 |
| 100.00 | 1.4 ± 0.2 | 1.5 ± 0.1 |

Mean ± SEM (Hemophilia A, n = 3; Hemophilia B, n = 2)

2. In Vivo Assays Demonstrating that
Microvesiculated TF is an Agent Useful for Topical
Antihemorrhagic Treatment in Severe Hemorrhage
Models (by Applying Directly on the Blood Vessel
Previously Sectioned)

Several in vivo assays were performed for the purpose of evaluating mTF capacity to cause fibrin clot in healthy and hemophilic subjects at different concentrations.

2.1 Microvesiculated TF is Useful as a Topical Hemostatic Agent in a Severe Hemorrhage Animal Model by Proximal Section of Rat Tails In vivo studies using a severe haemorrhage model in rat by total tail transection showed a significant reduction in bleeding time: from 18.16±1.61 to 8.36±0.82 minutes when animals were treated with 6HT-TF at 1494 ng/ml up to 1.7 µg of total protein concentration; from 18.16±5.98 to 9.33±1.05 minutes when animals were treated with CYE-TF at 200 ng/mL/min.

2.2 Microvesiculated TF is Useful as a Topical Hemostatic Agent in a Severe Hemorrhage Animal Model Previously Treated with Heparin In vivo studies using a severe haemorrhage model in anticoagulant (i.e. heparin 200 IU) pre-treated rat by total tail section showed a very significant antibleeding effect. Rats not treated with 6HT-TF bled to death after 90 minutes, where rats treated with 6HT-TF at 1494 ng/ml stop bleeding in 15.46±1.20 minutes and showed a 100% of survivability. On the other hand, the use of CYE-TF also showed similar antibleeding effect. Rats pre-treated with heparin bled to death after 90 minutes, while rats treated with CYE-TF stop bleeding in 14.2±2.4 (n=5) minutes and also showed a 100% of survivability. Rats pre-treated with warfarin reduced their coagulation time from 41.6±16.45 to 5.8±0.64 (n=3) minutes when treated with CYE-TF (200 ng/ml).

3. In Vivo Assays Demonstrating that
Microvesiculated TF is an Agent Useful for Topical
Antihemorrhagic Treatment in Lethal Hemorrhage
Models (by Applying Directly on the Blood Vessel
Previously Sectioned)

3.1 Microvesiculated TF is Useful as a Topical Hemostatic Agent in a Lethal Hemorrhage Animal Model by Proximal Section of FVIII Deficient Mice Tails In a lethal hemorrhage model in hemophilic mice (FVIII deficient mice), topic administration of 6HT-TF resulted in a dramatic reduction of bleeding time (from 31.4±4.74 to 5.14±0.69 minutes in hemophilic male and from 43.33±13.48 to 5.0±2.0 minutes in female mice) comparable with the bleeding time obtained in normal, non hemophilic mice (5.0±0.65 minutes). This bleeding time reduction was associated with no mortality in the group treated with 6HT-TF while all vehicles-treated hemophilic mice bled to death. Table 16 shows the results in five/three independent experiments for purified microvesiculated TF-hexa histidine tag fusion protein (6HT-TF).

TABLE 16

Purified microvesiculated TF-hexa histidine tag fusion protein (6HT-TF) decreases bleeding
time in a lethal hemorrhage model by proximal section of FVIII deficient mice tails

| | Treatment | Animal Weight (g) Mean + SEM | 6HT-TF (ng/mouse) Mean + SEM | Bleeding time (min) Mean + SEM | N | Mortality % | Mean (min) |
|---|---|---|---|---|---|---|---|
| Control male mice | Vehicle | 23.56 ± 0.74 | 0 +/− 0 | 5 ± 0.65 | 5 | 0 | — |
| Hemophilic male mice | Vehicle | 20.94 ± 0.35 | 0 +/− 0 | 31.4 ± 4.74 | 5 | 100 | 44.8 ± 8.43 |
| Hemophilic male mice | 6HT-TF | 21.04 ± 0.49 | 1807 +/− 291 | 5.14 ± 0.69 | 5 | 0 | — |
| Hemophilic female mice | Vehicle | 19.7 ± 1 | 0 +/− 0 | 43.33 ± 13.48 | 3 | 100 | 50 ± 16.04 |
| Hemophilic female mice | 6HT-TF | 19.43 ± 0.29 | 1618 +/− 498 | 5 ± 2 | 3 | 0 | — |

Mean ± SEM (Control and Hemophilic males, n = 5; Hemophilic females, n = 3)

Overall results show the potent haemostatic potential of mTF in healthy subjects and even in haemophilic patients, this demonstrated by in vitro (plasma and whole blood from haemophilic patients) as well as in vivo models using Haemophilia A gene defective mouse model. Additionally, mTF is able to coagulate plasmas with both the intrinsic and extrinsic pathways blocked.

The invention claimed is:

1. A topical composition comprising a pharmaceutically acceptable vehicle and tissue factor (TF)-bearing yeast derived microvesicles, said TF-bearing yeast derived microvesicles comprising (i) a yeast membrane, and (ii) a tissue factor (TF) protein or a variant thereof having pro-coagulant activity, wherein a portion of said tissue factor (TF) protein or variant thereof having pro-coagulant activity is integrated in said yeast membrane, and wherein said TF variant thereof having pro-coagulant activity is a mature tissue factor protein having at least one modification selected from the group consisting of: the inclusion of a tag bound to the N-terminal or C-terminal domain; the elimination of the signal peptide; the modification of a N-glycosylation site to make it non-functional; the elimination of all or part of the domain responsible for binding to FVIIa; and the introduction of a mutation in the domain responsible for binding to FVIIa which results in a substantially reduced affinity for FVIIa.

2. The topical composition according to claim 1, wherein said TF protein, or a variant thereof having pro-coagulant activity, is glycosylated.

3. The topical composition according to claim 1 that is a pharmaceutical composition comprising pharmaceutically acceptable vehicles, carriers or excipients.

4. The topical composition according to claim 1, wherein said TF protein, or a variant thereof having pro-coagulant activity, is human TF.

5. The topical composition according to claim 1, wherein said TF protein, or a variant thereof having pro-coagulant activity comprises a tag and said tag is a histidine tag (His-tag).

6. The topical composition according to claim 1, wherein said TF variant having pro-coagulant activity is the mature TF protein without the signal peptide.

7. The topical composition according to claim 1, wherein said TF variant having pro-coagulant activity comprises the interaction domain to Factor X (aa 174-251, SEQ ID NO: 13), the transmembrane region (aa 252-274, SEQ ID NO: 14), and the cytoplasmic tail (aa 275-295, SEQ ID NO: 15) of human TF protein, and lacks, partially or completely, the domain responsible for binding to FVIIa.

8. The topical composition according to claim 1, wherein said TF variant having pro-coagulant activity comprises the interaction domain to Factor X (aa 174-251, SEQ ID NO: 13), the transmembrane region (aa 252-274, SEQ ID NO: 14), and the cytoplasmic tail (aa 275-295, SEQ ID NO: 15) of the human TF protein and a histidine tag.

9. The topical composition according to claim 1, wherein said TF variant having pro-coagulant activity is human mature rTF protein containing at least one non-functional N-glycosylation site or sites corresponding to the N-glycosylation sites NLT at positions 11-13, NVT at positions 124-126, or NNT at positions 137-139 in the mature human rTF (SEQ ID NO: 17).

10. The topical composition according to claim 9 wherein said TF variant having pro-coagulant activity has one or more Asn-to-Ala mutations at the Asn residues in positions corresponding to positions 11, 124 or 137 in the mature human rTF (SEQ ID NO: 17).

11. The topical composition according to claim 1, wherein the N-terminal domain of said TF protein or variant thereof having pro-coagulant activity faces the exoplasmic side of said yeast membrane.

12. The topical composition according to claim 1, wherein the N-terminal domain of said TF protein or variant thereof having pro-coagulant activity faces the endoplasmic side of said yeast membrane.

13. The topical composition according to claim 1, wherein said TF-bearing yeast derived microvesicles have a size between 0.2 and 0.1 μm.

14. The topical composition according to claim 1, wherein said TF variant having pro-coagulant activity is human mature TF protein containing a histidine tag and a non-functional N-glycosylation site corresponding to Asn124Ala mutation.

15. A method for the treatment of haemorrhages comprising topically administering a composition according to claim 1 to a subject in need thereof.

16. A method for treating a disease which requires promoting cellular migration and/or angiogenesis, said method comprising topically administering a pharmaceutical composition according to claim 1 to a subject in need thereof.

17. A process for the manufacture of a topical composition according to claim 1 which comprises:
   a) subjecting a culture of recombinant yeast cells which express TF protein or a variant thereof having pro-coagulant activity as defined in claim 1 to fermentation under conditions which allow the expression of said TF protein or variant thereof;
   b) pelleting the product resulting from the fermentation of step a), to render a fermentation product;
   c) subjecting said fermentation product from step b) to homogenization in the absence of detergents, to render a fermentation homogenate; and
   d) subjecting said fermentation homogenate from step c) to separation, to render a pellet and a clarified yeast extract (CYE) containing said TF-bearing yeast derived microvesicle;
   e) collecting said clarified yeast extract (CYE) containing said TF-bearing yeast derived microvesicle; and
   f) if desired, isolating or purifying said TF-bearing yeast derived microvesicles having pro-coagulant activity.

18. The process according to claim 17, wherein said purifying is carried out by using one or more purification methods selected from the group consisting of size partitioning, tag purification, and immunoaffinity chromatography.

19. The process according to claim 17, wherein said purifying is size partitioning performed by tangential flow filtration and/or using membrane filters that retain microvesicles having a diameter of 0.1 to 0.2 μm and/or size exclusion chromatography.

* * * * *

UNITED STATES PATENT AND TRADEMARK OFFICE
CERTIFICATE OF CORRECTION

PATENT NO. : 8,759,294 B2  
APPLICATION NO. : 12/521492  
DATED : June 24, 2014  
INVENTOR(S) : Pedreño Egea et al.

Page 1 of 1

It is certified that error appears in the above-identified patent and that said Letters Patent is hereby corrected as shown below:

Title Page, Item (75) Inventors, change "Francisco Javier Pedrño Egea" to -- Francisco Javier Pedreño Egea --

In the Claims,

Column 69, Line 19: change "f) if desired, isolating or purifying said TF-bearing yeast" to -- f) purifying said TF-bearing yeast --

Signed and Sealed this  
Thirteenth Day of January, 2015

Michelle K. Lee  
*Deputy Director of the United States Patent and Trademark Office*

SEQUENCE LISTING

<160> NUMBER OF SEQ ID NOS: 17

<210> SEQ ID NO 1
<211> LENGTH: 295
<212> TYPE: PRT
<213> ORGANISM: Homo sapiens

<400> SEQUENCE: 1

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
        275                 280                 285

Asn Ser Pro Leu Asn Val Ser
    290                 295

<210> SEQ ID NO 2
<211> LENGTH: 6
<212> TYPE: PRT
<213> ORGANISM: Artificial Sequence
<220> FEATURE:
<223> OTHER INFORMATION: Amino acid sequence useful for isolating or
      purifying a fusion protein

<400> SEQUENCE: 2

Ala His Gly His Arg Pro
1               5

<210> SEQ ID NO 3
<211> LENGTH: 14
<212> TYPE: PRT
<213> ORGANISM: Artificial Sequence
<220> FEATURE:
<223> OTHER INFORMATION: Amino acid sequence useful for isolating or
      purifying a fusion protein

<400> SEQUENCE: 3

Pro Ile His Asp His Asp His Pro His Leu Val Ile His Ser
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Amino acid sequence useful for isolating or
      purifying a fusion protein
<220> FEATURE:
<221> NAME/KEY: MISC_FEATURE
<222> LOCATION: (5)..(6)
<223> OTHER INFORMATION: Xaa can be any naturally occurring amino acid

<400> SEQUENCE: 4

Gly Met Thr Cys Xaa Xaa Cys
1               5

<210> SEQ ID NO 5
<211> LENGTH: 888
<212> TYPE: DNA
<213> ORGANISM: Homo sapiens

<400> SEQUENCE: 5

```
atggagaccc ctgcctggcc ccgggtcccg cgccccgaga ccgccgtcgc tcggacgctc      60
ctgctcggct gggtcttcgc ccaggtggcc ggcgcttcag gcactacaaa tactgtggca     120
gcatataatt taacttggaa atcaactaat ttcaagacaa ttttggagtg ggaacccaaa     180
cccgtcaatc aagtctacac tgttcaaata agcactaagt caggagattg gaaaagcaaa     240
tgcttttaca caacagacac agagtgtgac ctcaccgacg agattgtgaa ggatgtgaag     300
cagacgtact tggcacgggt cttctcctac ccggcaggga atgtggagag caccggttct     360
gctggggagc tctgtatga gaactcccca gagttcacac cttacctgga acaaacctc      420
ggacagccaa caattcagag ttttgaacag gtgggaacaa aagtgaatgt gaccgtagaa     480
gatgaacgga ctttagtcag aaggaacaac actttcctaa gcctccggga tgttttggc     540
aaggacttaa tttatacact ttattattgg aaatcttcaa gttcaggaaa gaaaacagcc     600
aaaacaaaca ctaatgagtt tttgattgat gtggataaag gagaaaacta ctgtttcagt     660
gttcaagcag tgattccctc ccgaacagtt aaccggaaga gtacagacag cccggtagag     720
tgtatgggcc aggagaaagg ggaattcaga gaaatattct acatcattgg agctgtggta     780
tttgtggtca tcatccttgt catcatcctg gctatatctc tacacaagtg tagaaaggca     840
ggagtggggc agagctggaa ggagaactcc ccactgaatg tttcataa                   888
```

```
<210> SEQ ID NO 6
<211> LENGTH: 33
<212> TYPE: DNA
<213> ORGANISM: Artificial Sequence
<220> FEATURE:
<223> OTHER INFORMATION: Primer TT-7071 used to generate the
      glycosylation mutants in TF

<400> SEQUENCE: 6
tgacaccgtc gtatacgtaa ttgaaccttt agt                                33

<210> SEQ ID NO 7
<211> LENGTH: 33
<212> TYPE: DNA
<213> ORGANISM: Artificial Sequence
<220> FEATURE:
<223> OTHER INFORMATION: Primer TT7075 used to generate the
      glycosylation mutants in TF

<400> SEQUENCE: 7
actgtggcag catatcgatt aacttggaaa tca                                33

<210> SEQ ID NO 8
<211> LENGTH: 33
<212> TYPE: DNA
<213> ORGANISM: Artificial Sequence
<220> FEATURE:
<223> OTHER INFORMATION: Primer TT-7072 used to generate the
      glycosylation mutants in TF

<400> SEQUENCE: 8
atcttctacg gtcactgcca cttttgttcc cac                                33

<210> SEQ ID NO 9
<211> LENGTH: 33
<212> TYPE: DNA
<213> ORGANISM: Artificial Sequence
<220> FEATURE:
<223> OTHER INFORMATION: Primer TT-7076 used to generate the
      glyspsylation mutants in TF

<400> SEQUENCE: 9
gtgggaacaa aagtggcagt gaccgtagaa gat                                33

<210> SEQ ID NO 10
<211> LENGTH: 33
<212> TYPE: DNA
<213> ORGANISM: Artificial Sequence
<220> FEATURE:
<223> OTHER INFORMATION: Primer TPM1 used to generate the glysosylation
      mutants in TF

<400> SEQUENCE: 10
actttagtca gttgggcaaa cactttccta agc                                33

<210> SEQ ID NO 11
<211> LENGTH: 33
<212> TYPE: DNA
<213> ORGANISM: Artificial Sequence
<220> FEATURE:
<223> OTHER INFORMATION: Primer TPM2 used to generate the glysosylation
      mutants in TF

<400> SEQUENCE: 11
gcttaggaaa gtgtttgccc ttctgactaa agt                                33
```

<210> SEQ ID NO 12
<211> LENGTH: 960
<212> TYPE: DNA
<213> ORGANISM: Homo sapiens

<400> SEQUENCE: 12

```
cccacgggcg ccacggaacc cgctcgatct cgccgccaac tggtagacat ggagacccct      60
gcctggcccc gggtcccgcg ccccgagacc gccgtcgctc ggacgctcct gctcggctgg     120
gtcttcgccc aggtggccgg cgcttcaggc actacaaata ctgtggcagc atataattta     180
acttggaaat caactaattt caagacaatt ttggagtggg aacccaaacc cgtcaatcaa     240
gtctacactg ttcaaataag cactaagtca ggagattgga aaagcaaatg cttttacaca     300
acagacacag agtgtgacct caccgacgag attgtgaagg atgtgaagca gacgtacttg     360
gcacgggtct ctcctacccc ggcagggaat gtggagagca ccggttctgc tgggagcct      420
ctgtatgaga actccccaga gttcacacct tacctggaga caaacctcgg acagccaaca     480
attcagagtt ttgaacaggt gggaacaaaa gtgaatgtga ccgtagaaga tgaacggact     540
ttagtcagaa ggaacaacac tttcctaagc ctccgggatg ttttttggcaa ggacttaatt     600
tatacacttt attattggaa atcttcaagt tcaggaaaga aaacagccaa acaaacact      660
aatgagtttt tgattgatgt ggataaagga gaaaactact gtttcagtgt tcaagcagtg     720
attccctccc gaacagttaa ccggaagagt acagacagcc cggtagagtg tatgggccag     780
gagaaagggg aattcagaga aatattctac atcattggag ctgtggtatt tgtggtcatc     840
atccttgtca tcatcctggc tatatctcta cacaagtgta gaaaggcagg agtggggcag     900
agctggaagg agaactcccc actgaatgtt tcataaagga agcactgttg gagctactgc     960
```

<210> SEQ ID NO 13
<211> LENGTH: 78
<212> TYPE: PRT
<213> ORGANISM: Homo sapiens

<400> SEQUENCE: 13

```
Ser Leu Arg Asp Val Phe Gly Lys Asp Leu Ile Tyr Thr Leu Tyr Tyr
1               5                   10                  15

Trp Lys Ser Ser Ser Gly Lys Lys Thr Ala Lys Thr Asn Thr Asn
            20                  25                  30

Glu Phe Leu Ile Asp Val Asp Lys Gly Glu Asn Tyr Cys Phe Ser Val
        35                  40                  45

Gln Ala Val Ile Pro Ser Arg Thr Val Asn Arg Lys Ser Thr Asp Ser
    50                  55                  60

Pro Val Glu Cys Met Gly Gln Glu Lys Gly Glu Phe Arg Glu
65                  70                  75
```

<210> SEQ ID NO 14
<211> LENGTH: 23
<212> TYPE: PRT
<213> ORGANISM: Homo sapiens

<400> SEQUENCE: 14

```
Ile Phe Tyr Ile Ile Gly Ala Val Val Phe Val Val Ile Ile Leu Val
1               5                   10                  15

Ile Ile Leu Ala Ile Ser Leu
            20
```

<210> SEQ ID NO 15
<211> LENGTH: 21
<212> TYPE: PRT
<213> ORGANISM: Homo sapiens

<400> SEQUENCE: 15

```
His Lys Cys Arg Lys Ala Gly Val Gly Gln Ser Trp Lys Glu Asn Ser
1               5                   10                  15

Pro Leu Asn Val Ser
            20
```

<210> SEQ ID NO 16
<211> LENGTH: 141
<212> TYPE: PRT
<213> ORGANISM: Homo sapiens

<400> SEQUENCE: 16

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu
    130                 135                 140
```

<210> SEQ ID NO 17
<211> LENGTH: 263
<212> TYPE: PRT
<213> ORGANISM: Homo sapiens

<400> SEQUENCE: 17

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125
```

-continued

```
Asp Glu Arg Thr Leu Val Arg Arg Asn Asn Thr Phe Leu Ser Leu Arg
    130                 135             140

Asp Val Phe Gly Lys Asp Leu Ile Tyr Thr Leu Tyr Tyr Trp Lys Ser
145             150                 155                 160

Ser Ser Ser Gly Lys Lys Thr Ala Lys Thr Asn Thr Asn Glu Phe Leu
            165                 170                 175

Ile Asp Val Asp Lys Gly Glu Asn Tyr Cys Phe Ser Val Gln Ala Val
            180                 185             190

Ile Pro Ser Arg Thr Val Asn Arg Lys Ser Thr Asp Ser Pro Val Glu
        195                 200             205

Cys Met Gly Gln Glu Lys Gly Glu Phe Arg Glu Ile Phe Tyr Ile Ile
    210                 215             220

Gly Ala Val Val Phe Val Val Ile Ile Leu Val Ile Ile Leu Ala Ile
225             230                 235                 240

Ser Leu His Lys Cys Arg Lys Ala Gly Val Gly Gln Ser Trp Lys Glu
            245                 250             255

Asn Ser Pro Leu Asn Val Ser
            260
```